US008606595B2

(12) United States Patent
Udani

(10) Patent No.: US 8,606,595 B2
(45) Date of Patent: Dec. 10, 2013

(54) METHODS AND SYSTEMS FOR ASSURING COMPLIANCE

(76) Inventor: Sanjay Udani, Northridge, CA (US)

( * ) Notice: Subject to any disclaimer, the term of this patent is extended or adjusted under 35 U.S.C. 154(b) by 91 days.

(21) Appl. No.: 13/163,591

(22) Filed: Jun. 17, 2011

(65) Prior Publication Data

US 2012/0323589 A1 Dec. 20, 2012

(51) Int. Cl.
*G06Q 10/00* (2012.01)
(52) U.S. Cl.
USPC .................................. 705/2; 705/3
(58) Field of Classification Search
USPC ............................................................ 705/2
See application file for complete search history.

(56) References Cited

U.S. PATENT DOCUMENTS

| | | | |
|---|---|---|---|
| 5,850,211 A | 12/1998 | Tognazzini | |
| 5,867,821 A | 2/1999 | Ballantyne | |
| 6,149,440 A | 11/2000 | Clark et al. | |
| 6,171,112 B1 | 1/2001 | Clark et al. | |
| 6,195,640 B1 | 2/2001 | Mullaly et al. | |
| 6,196,970 B1 | 3/2001 | Brown | |
| 6,496,827 B2 | 12/2002 | Kozam et al. | |
| 6,553,494 B1 | 4/2003 | Glass | |
| 6,687,190 B2 | 2/2004 | Momich et al. | |
| 6,820,235 B1 | 11/2004 | Bleicher et al. | |
| 6,879,970 B2 | 4/2005 | Shiffman et al. | |
| 7,054,823 B1 | 5/2006 | Briegs et al. | |
| 7,089,247 B2 | 8/2006 | Kloos et al. | |
| 7,415,447 B2 | 8/2008 | Shiffman et al. | |
| 7,636,668 B1 | 12/2009 | Alves et al. | |
| 7,693,729 B2 | 4/2010 | Yankelevitz et al. | |
| 7,783,072 B2 | 8/2010 | Work et al. | |
| 7,801,747 B2 | 9/2010 | Califano et al. | |
| 7,860,287 B2 | 12/2010 | Zahlmann et al. | |
| 7,873,589 B2 | 1/2011 | Shiffman et al. | |
| 7,899,685 B2 | 3/2011 | Wallach et al. | |
| 7,941,534 B2 | 5/2011 | De La Huerga | |
| 2002/0007287 A1 | 1/2002 | Straube et al. | |
| 2002/0029194 A1 | 3/2002 | Lewis et al. | |
| 2002/0091651 A1 | 7/2002 | Petrogiannis et al. | |
| 2002/0143563 A1 | 10/2002 | Hufford et al. | |
| 2002/0156640 A1 | 10/2002 | Hufford et al. | |
| 2002/0194131 A1 | 12/2002 | Dick | |
| 2003/0033168 A1 | 2/2003 | Califano et al. | |
| 2003/0036683 A1 | 2/2003 | Kehr et al. | |
| 2003/0163488 A1 | 8/2003 | Kloos et al. | |
| 2004/0006553 A1 | 1/2004 | De Vires et al. | |
| 2004/0010418 A1 | 1/2004 | Buonocore et al. | |

(Continued)

FOREIGN PATENT DOCUMENTS

KR 10-2009-0097902 9/2009
KR 10-2009-0120831 11/2009

(Continued)

OTHER PUBLICATIONS

PCT International Search Report for PCT/US2009/068601 filed on Dec. 17, 2009 in the name of Sanjay Udani.

(Continued)

*Primary Examiner* — Hiep V Nguyen
(74) *Attorney, Agent, or Firm* — Steinfl & Bruno, LLP

(57) ABSTRACT

Systems and methods for collecting information, verifying authenticity of such information, processing, maintaining, and managing such information are described. The system can be a standalone unit or can comprise a combination of various units configured to function together.

31 Claims, 32 Drawing Sheets

(56) References Cited

U.S. PATENT DOCUMENTS

| | | |
|---|---|---|
| 2004/0078216 A1 | 4/2004 | Toto |
| 2004/0093240 A1 | 5/2004 | Shah |
| 2004/0172447 A1 | 9/2004 | Miller |
| 2004/0249664 A1 | 12/2004 | Broverman et al. |
| 2005/0086082 A1 | 4/2005 | Braunstein et al. |
| 2005/0149869 A1 | 7/2005 | Kehr et al. |
| 2005/0240305 A1 | 10/2005 | Bogash et al. |
| 2006/0184493 A1 | 8/2006 | Shiffman et al. |
| 2006/0188444 A1 | 8/2006 | Irie et al. |
| 2006/0282292 A1 | 12/2006 | Brink et al. |
| 2006/0293919 A1 | 12/2006 | Morlet et al. |
| 2006/0294108 A1 | 12/2006 | Adelson et al. |
| 2007/0016443 A1 | 1/2007 | Wachman et al. |
| 2007/0030339 A1 | 2/2007 | Findlay et al. |
| 2007/0038472 A1 | 2/2007 | Finken et al. |
| 2007/0123772 A1 | 5/2007 | Euliano et al. |
| 2007/0157079 A1 | 7/2007 | Baker |
| 2007/0269557 A1* | 11/2007 | Culver et al. .................. 426/72 |
| 2008/0009766 A1 | 1/2008 | Holmes et al. |
| 2008/0021741 A1 | 1/2008 | Holla et al. |
| 2008/0021834 A1 | 1/2008 | Holla et al. |
| 2008/0045806 A1* | 2/2008 | Keppler ........................ 600/300 |
| 2008/0052259 A1 | 2/2008 | Shiffman et al. |
| 2008/0065418 A1 | 3/2008 | Byrom et al. |
| 2008/0114616 A1 | 5/2008 | Ferguson |
| 2008/0133267 A1 | 6/2008 | Maltezos et al. |
| 2008/0198012 A1* | 8/2008 | Kamen ....................... 340/572.1 |
| 2008/0256128 A1 | 10/2008 | Pierce et al. |
| 2008/0270181 A1 | 10/2008 | Rosenberg |
| 2008/0270420 A1 | 10/2008 | Rosenberg |
| 2009/0024415 A1* | 1/2009 | Alpert et al. ...................... 705/3 |
| 2009/0164245 A1 | 6/2009 | Toleti et al. |
| 2010/0039618 A1 | 2/2010 | De Lemos |
| 2010/0146385 A1 | 6/2010 | Goulandris |
| 2010/0268544 A1 | 10/2010 | Nitahara et al. |
| 2010/0324380 A1 | 12/2010 | Perkins et al. |
| 2011/0004852 A1 | 1/2011 | Baugh |
| 2011/0106557 A1 | 5/2011 | Gazula |
| 2011/0125528 A1 | 5/2011 | Padate et al. |
| 2011/0251855 A1 | 10/2011 | Lorsch |
| 2012/0001923 A1 | 1/2012 | Weinzimmer et al. |
| 2012/0304054 A1 | 11/2012 | Orf et al. |
| 2013/0110547 A1 | 5/2013 | Englund et al. |

FOREIGN PATENT DOCUMENTS

| | | |
|---|---|---|
| WO | 2006/100646 | 9/2006 |
| WO | 2008/134235 | 6/2008 |
| WO | 2008/134235 | 11/2008 |
| WO | 2009/008968 | 1/2009 |
| WO | 2010/071802 | 6/2010 |

OTHER PUBLICATIONS

PCT Written Opinion mailed on Aug. 17, 2010 for PCT Application PCT/2009/068601 filed on Dec. 17, 2009 in the name of Sanjay Udani.

PCT Written Opinion mailed on Nov. 30, 2012 for PCT Application PCT/2012/042544 filed on Jun. 14, 2012 in the name of Sanjay Udani.

PCT Written Opinion mailed on Nov. 29, 2012 for PCT Application PCT/2012/042545 filed on Jun. 14, 2012 in the name of Sanjay Udani.

Non-Final Office Action mailed on Nov. 16, 2012 for U.S. Appl. No. 13/163,569, filed Jun. 17, 2011 in the name of Sanjay Udani.

Non-Final Office Action mailed on Mar. 27, 2013 for U.S. Appl. No. 13/163,608, filed Jun. 17, 2011 in the name of Sanjay Udani.

Non-Final Office Action mailed on Mar. 19, 2013 for U.S. Appl. No. 13/163,616, filed Jun. 17, 2011 in the name of Sanjay Udani.

U.S. Dept. of Health & Human Svs., Draft Guidelines—Guidance for Industry Electronic Source Documentation in Clinical Investigations, Dec. 2010, pp. 1-18.

International Council on Harminization, Guidance for Industry E6 Good Clinical Practices: Consolidated Guidance, Apr. 1996, pp. 1-63.

Clinical Research & Clinical Trials. *National Institute of Health*, retrieved from http://www.nichd.nih.gov/health/clinicalresearch/ on Jan. 7, 2013.

Wellness Council of America. Wellness Council of America. *Wellness Council of America* retrieved from www.welcoa.org on Jan. 7, 2013.

World Health Organization, Adherence to Long-term Therapies—Evidence for Action, 2003, pp. 1-16.

PCT International Search Report mailed on Nov. 29, 2012 for PCT Application PCT/US2012/042545 filed on Jun. 14, 2012 in the name of Sanjay Udani.

PCT International Search Report mailed on Nov. 30, 2012 for PCT Application PCT/US2012/042544 filed on Jun. 14, 2012 in the name of Sanjay Udani.

PCT International Search Report mailed on Feb. 28, 2013 for PCT Application PCT/US2012/042548 filed on Jun. 14, 2012 in the name of Sanjay Udani.

PCT International Search Report mailed on Feb. 22, 2013 for PCT Application PCT/US2012/042543 filed on Jun. 14, 2012 in the name of Sanjay Udani.

PCT Written Opinion mailed on Feb. 22, 2013 for PCT Application PCT/US2012/042543 filed on Jun. 14, 2012 in the name of Sanjay Udani.

PCT Written Opinion mailed on Feb. 28, 2013 for PCT Application PCT/US2012/042548 filed on Jun. 14, 2012 in the name of Sanjay Udani.

Final Office Action mailed on Jun. 17, 2013 for U.S. Appl. No. 13/163,569, filed Jun. 17, 2011 in the name of Sanjay Udani.

Notice of Allowance mailed on Jul. 26, 2013 for U.S. Appl. No. 13/163,56, filed Jun. 17, 2011 in the name of Sanjay Udani.

Informed Consent retrieved from http://web.archive.org/web/20100625061118/http:irb.uconn.edu/irb_sop/IRBSOP_informed_consent.html on Jun. 4, 2012, pp. 9.

\* cited by examiner

IF THE AGREEMENT SIGNER SELECTS THE WRONG ANSWER THEN SPECIFIC PARTS OF THE TEXT ARE HIGHLIGHTED TO SHOW WHERE THE ANSWER IS.

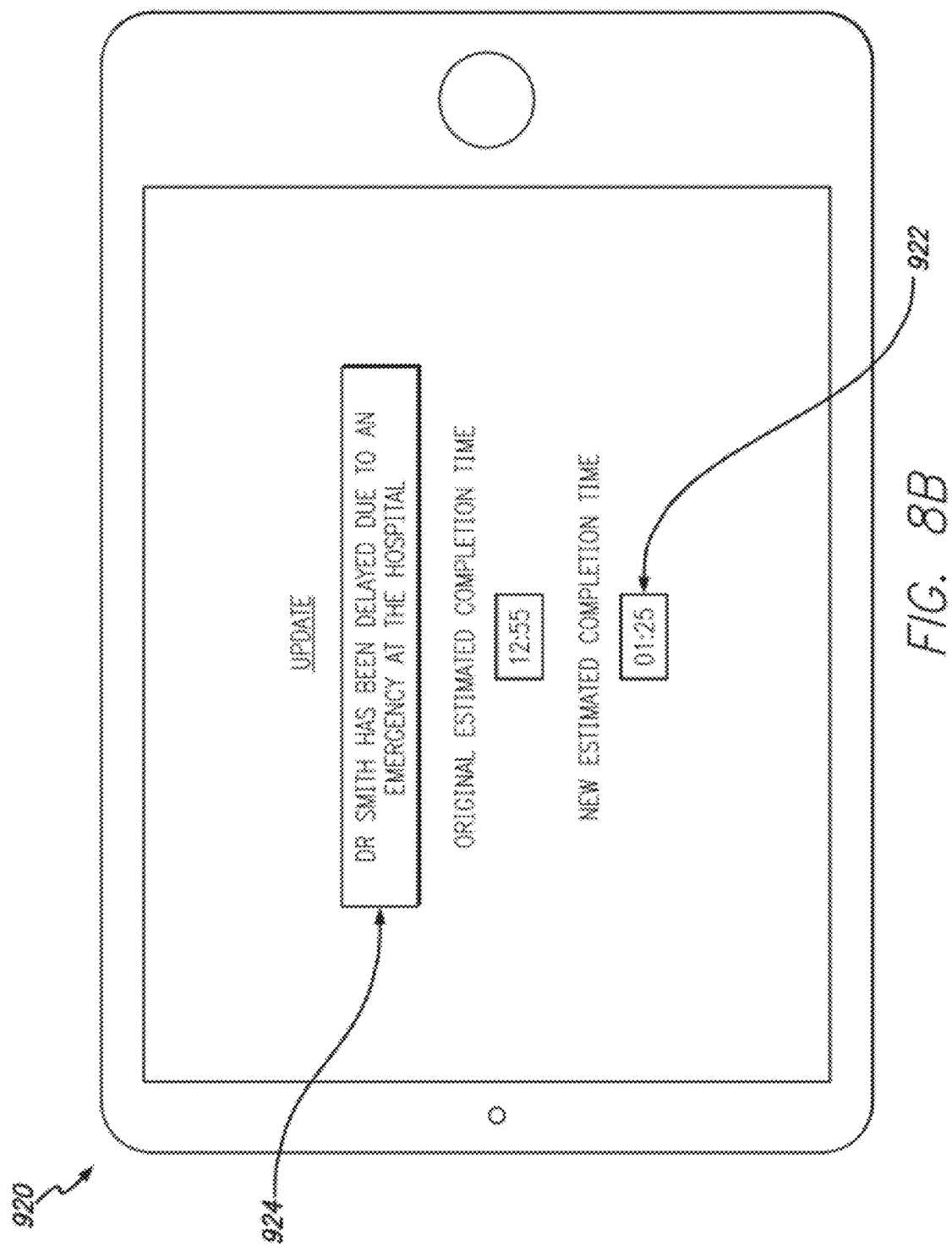

METHODS AND SYSTEMS FOR ASSURING COMPLIANCE

CROSS REFERENCE TO RELATED APPLICATIONS

The present application is related to U.S. patent application Ser. No. 13/140,015 entitled "System for Performing Clinical Trials," filed on Jun. 15, 2011, which is the national stage entry of and claims priority to Patent Cooperation Treaty Application No. PCT/US2009/068601 entitled "System for Performing Clinical Trials," filed on Dec. 17, 2009, which, in turn, claims priority to U.S. Provisional Application No. 61/138,477 filed on Dec. 17, 2008, entitled "Method and Device for Performing Clinical Trials," the disclosures of which are all incorporated herein by reference in their entirety.

The present application is also related to U.S. patent application Ser. No. 13/163,569 entitled "Methods and Systems for Recording Verifiable Documentation", filed on even date herewith; U.S. patent application Ser. No. 13/163,608 entitled "Methods and Systems for Electronic Medical Protocol", filed on even date herewith; and U.S. patent application Ser. No. 13/163,616 entitled "Methods and Systems for Electronic Medical Source", filed on even date herewith, the disclosures of which are all incorporated herein by reference in their entirety.

FIELD

The present disclosure relates to collecting, verifying, and processing information. In particular, it relates to methods and systems for assuring compliance.

BACKGROUND

Clinical trials are some of the most expensive and difficult projects to perform. The average cost of pharmaceutical drug development is estimated to be between $80 million and $800 million depending on complexity and therapeutic area. Despite all of the advances in clinical trial technology, most clinical trial protocols are designed by committees and groups of highly paid people and take months to design. Once the protocol is approved by an appropriate regulatory body, it must be run at study centers all over the world. Each doctor and clinical research coordinator must then interpret the protocol to determine exactly what is required of them and their patients. They must then identify patients who might be appropriate for the study, obtain their consent, and then collect data on those patients over a period of months or years. The difficulty in performing such tasks and the inherent variability in these tasks being performed by hundreds or thousands of people in dozens of countries can lead to poor quality data, fraud, delays, and higher costs.

From a perspective of patients who have volunteered and/or were selected to be part of the study, the whole study process can be intimidating and confusing. It is not uncommon for the patients to be required to read and sign a 25 page legal document, thereby agreeing to certain terms and conditions of the study without actually understanding what they are signing. Once the patients are signed up for the study, they may be required to consume a pill at certain intervals and/or may be required to perform certain tasks at home such as answering questions and/or measuring their own body temperature, to name a few. If the patients fail to follow their instructions, the results from the study become inaccurate.

From a research coordinator's perspective, many hours are spent seeing the patients, asking the patients appropriate questions, performing certain procedures (e.g., drawing blood), dispending pills, instructing the patients. Such activities are then generally followed by processing paperwork. Results obtained from such tasks have to be logged and ultimately entered into a database system for further analysis. Each of these processes can be extremely time consuming.

On the other hand, a clinical research monitor oversees the research study project and can typically find that the research coordinators, doctors, patients, and nurses have not fully complied with the guidance specified in the protocol. Sometimes, lack of full compliance is intentional whereas other times it is unintentional. Non-compliance can result from data entry error, forgery, or lack of understanding, all of which can result in non-usable information for the research study, thereby costing more money to complete the study.

A sponsor spends a lot of money to perform such research studies and is always looking for ways to reduce their costs. One method of lowering such costs is to minimize redundancy and errors (or non-compliance) so that the studies can be performed in a shorter amount of time and without having to redo studies.

SUMMARY

According to a first aspect, a method of executing agreements is described, the method comprising: providing an electronic device with a display, wherein the electronic device is loaded with a software application and/or remotely accessing the software application; selecting a desired agreement on the electronic device to be executed by a party to the agreement; recording information identifying the party to the agreement with the electronic device; displaying the agreement on the display of the electronic device; documenting the party while the party reviews the displayed agreement; verifying that the party comprehends contents, requirements, nature of the agreement, and/or terms of the agreement; agreeing to the contents, requirements, nature of the agreement and/or terms of the agreement by signing the agreement; and documenting the party executing the agreement, whereby the recording authenticates the party executing the agreement.

According to a second aspect, a method of executing agreements is described, the method comprising: providing an electronic device with a display, and loaded with a software application and/or remotely accessing the software application; recording information identifying a party to the agreement with the electronic device and a camera; recording the party with the camera while the party verbally discusses the agreement; agreeing to the contents, requirements, nature of the agreement and/or terms of the agreement by signing for the agreement; and recording the party executing the agreement, whereby the recording authenticates the party executing the agreement, wherein the signing is selected from the group consisting of: a digital signature, electronic signature, biometric signature, and recorded verbal agreement.

According to a third aspect, a device for executing agreements between parties is described, the device comprising: an electronic device with a display, the electronic device loaded with a software application and/or remotely accessing the software application on a remote server, the display adapted to display the agreement; a documenting device configured to be controlled by the software application; and memory connected with the electronic device, the memory adapted to store information identifying a party, wherein the electronic device is adapted to record the party with the documenting device while the party reviews the agreement and store recorded information on the memory, wherein the electronic device is adapted to verify that the party comprehends contents, requirements, nature of the agreement, and/or terms of the agreement, wherein the electronic device is adapted to authenticate the party agreeing to the agreement, and wherein the electronic device is adapted to send information stored in the memory to a server separate from the electronic device.

According to a fourth aspect, a system for executing agreements between parties is described, the system comprising: the device according to the third aspect, the system comprising: a database library accessible by the electronic device, the database library further comprising a plurality of agreements configured to be selected by a user to be loaded on the electronic device.

According to a fifth aspect, a method of confirming identity and attendance is described, the method comprising: providing an electronic device and a documenting device, the electronic device being loaded with a software application and/or remotely accessing the software application; authenticating identity of a subject by recording an initial set of biometric identity characteristics; comparing the initially recorded biometric identity characteristics with new biometric characteristics captured by the electronic device; providing a library of biometric identity characteristics stored in a database, the biometric identity characteristics associated with personnel belonging to a group; and comparing the biometric identity characteristics of the subject with the biometric identity characteristics stored in the database, wherein the comparing determines if the subject belongs to the group.

According to a sixth aspect, a device for confirming identity and attendance is described, the device comprising: an electronic device loaded with a software application and/or remotely accessing the software application on a remote server; and a documenting device adapted to be operated with the electronic device, wherein the electronic device is adapted to compare biometric characteristics of a subject obtained from the documenting device, and wherein the electronic device is adapted to verify the subject has signed required documents based on identity information obtained from the documenting device.

According to a seventh aspect, a method for assembling a protocol is described, the method comprising: selecting at least one protocol module from an electronic library; selecting at least one protocol element from an electronic library; and creating at least one document for execution of the electronic protocol, wherein each document comprises one or more sets of structured information and instructions, and wherein each set of structured information and instructions required for performance of the electronic protocol is selected from the group consisting of results, data, forms, content, guidance, directions, standards, and requirements, thus assembling the protocol.

According to an eighth aspect, a library system for protocol information is described, the system comprising at least one protocol, wherein the protocol comprises at least one protocol module, wherein the protocol module comprises at least one protocol element, and wherein the protocol element comprises a set of structured information and instructions for performance of the protocol.

According to a ninth aspect, an electronic device for assembling a protocol is described, the device comprising: a network connection adapted for accessing an library of protocols, protocol modules, and protocol elements; a display adapted for displaying a catalogue of the electronic library; an interface device adapted for selecting at least one protocol, protocol module, or protocol element from the electronic library; and a software application loaded on the electronic device or accessed by the electronic device and adapted for creating at least one document for the execution of an electronic protocol, wherein each document comprises one or more sets of structured information and instructions, and wherein each set of structured information and instructions required for performance of the protocol is selected from the group consisting of results, data, forms, content, guidance, directions, standards, and requirements, thus assembling the protocol.

According to a tenth aspect, a method for collecting medical data is described, the method comprising: a) providing an electronic device loaded with a software application and/or remotely accessing the software application; b) providing a display for showing output from the electronic device, wherein the display is suitable for accepting input from the electronic device; c) displaying a first step to be performed by a doctor with a subject during a visit, wherein the first step is a question to be asked to the subject or procedure to be performed on the subject; d) displaying additional instructions for the first step; e) displaying an input to be provided by the doctor based on the first step performed; f) accepting the input based on the first step performed; and g) iterating c) through f) for at least a second step, thus collecting the medical data.

According to an eleventh aspect, a system for collecting medical data is described, the system comprising: a) an electronic device loaded with a software application and/or remotely accessing the software application for collection of medical data; b) a display adapted for showing output from the electronic device, wherein the display is adapted for accepting input from the electronic device; and c) a network connection adapted for connecting the electronic device to a server for accessing an application or data and for sending information accepted by the electronic device stored on a memory of the electronic device to the server.

According to a twelfth aspect, an electronic device is described, the device comprising a display adapted for showing output from the electronic device, wherein the display is configured to display a progress bar showing steps to be performed during a visit or service and an indicator symbol to differentiate between steps of the visit already performed from steps of the visit to be performed.

According to a thirteenth aspect, a method of measuring and enforcing compliance is described, the method comprising: providing guidance; providing an electronic device loaded with a software application and/or accessing a remote application; providing an activity to be performed by a subject according to the guidance; validating identity of the subject performing the activity; verifying the identity of products used to perform the activity by the subject; recording the subject performing the activity with the electronic device; and comparing movements of the subject performing the activity with movements expected for a subject performing similar activities, thereby ensuring the subject is complying with the provided guidance.

According to a fourteenth aspect, a device for complying to guidance is described, the device comprising: an electronic device loaded with a software application and/or accessing a remote application; a validating device adapted to identify identity of a subject according to the guidance; a verifying device adapted to verify identity of a product; and a memory for use with the electronic device adapted to record the identity of the subject and the identity of the product, wherein the electronic device is adapted to send information stored in the memory to a server separate from the electronic device.

According to a fifteenth aspect, an electronic device is described, the device comprising: a biometric characteristics capturing device; an application adapted to perform biometric recognition; and a database locally connected with the electronic device, wherein the biometric recognition is performed by comparing a set of biometric characteristics against a library of biometric characteristics, and wherein the library of biometric characteristics is located in the database.

According to a sixteenth aspect, a method of verifying dietary compliance is described, the method comprising: providing an electronic device loaded with a software application and/or accessing a remote application, the software application adapted to identify physical characteristics of food products; identifying the food products according to the physical characteristics of the food products, wherein the identifying is adapted to determine nutritional values of the food products; and analyzing the nutritional values of the food products, thereby verifying compliance or non-compliance of the food products according to dietary guidelines predetermined for a subject.

The details of one or more embodiments of the disclosure are set forth in the accompanying drawings and the description below. Other features, objects, and advantages will be apparent from the description and drawings, and from the claims.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

FIGS. 8A-8B show displays of an exemplary electronic progress unit of the present disclosure.

DETAILED DESCRIPTION

Definitions

Figure 1:
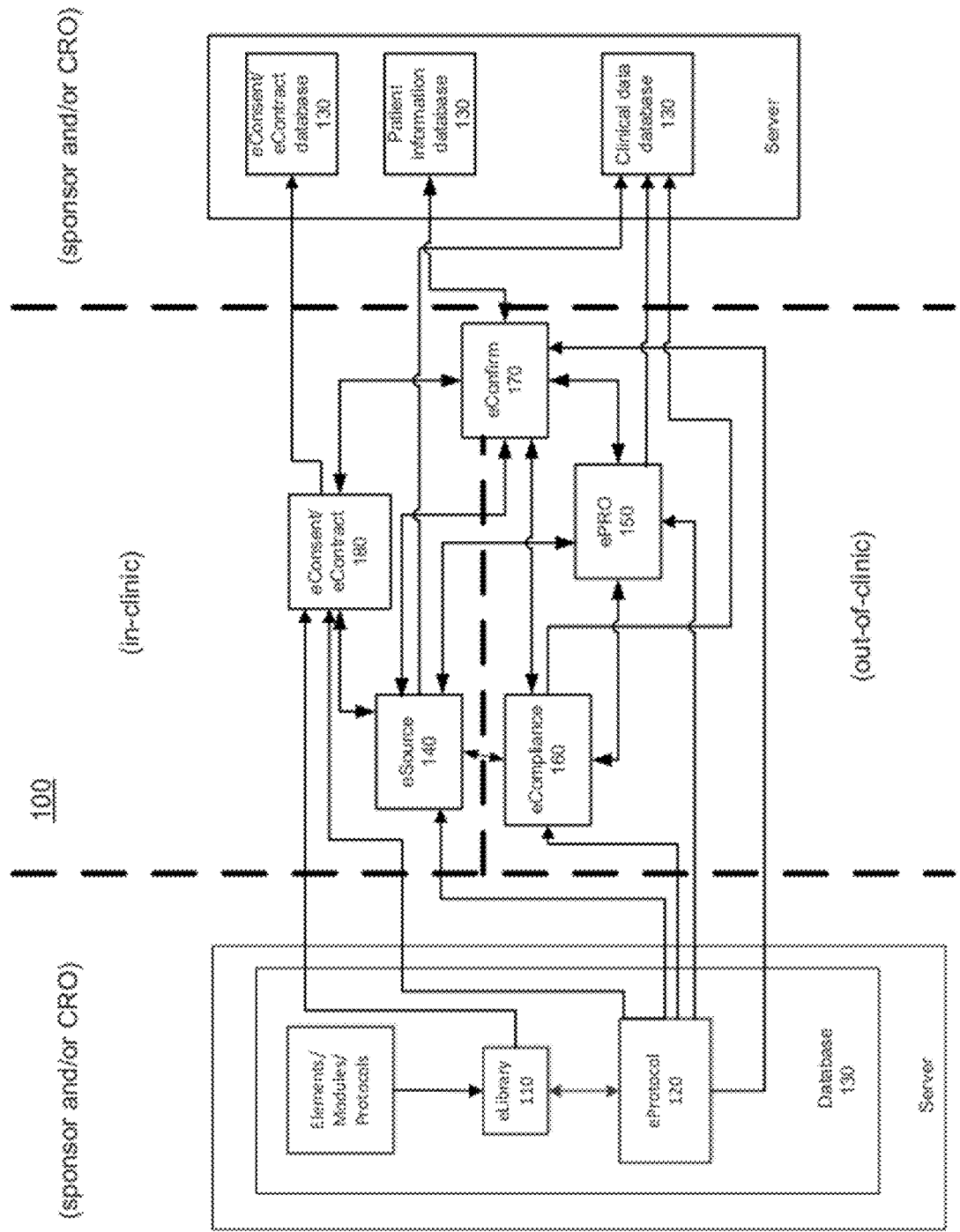
FIG. 1 shows an overview diagram of an exemplary system of an embodiment of the present disclosure.

For clarity purposes, the following terms are defined for use within the present disclosure.

The term "sponsor" is defined to mean a corporation, an entity, a person of governmental body, or an agency who sponsors a clinical trial and has an interest in the result.

The term "protocol" is defined to mean a document containing the objectives, design, methodology, statistical considerations, and organization of a protocol-defined medical care. Examples of protocol-defined medical care may include, but are not limited to, clinical trials, disease management, wellness management, medical order sets, medical care plans, medical pathways, and medical guidelines. A protocol specific to a clinical study is referred to as a clinical study protocol.

The term "source" is defined to mean an original recording of data related to protocol-defined medical care. For example, specifically for clinical trials, a source is defined by the FDA as all information in original records and certified copies of original records or clinical findings, observations, or other activities in a clinical trial necessary for reconstruction and evaluation of the trial. Source data may be contained in source documents (original records or certified copies).

The term "module" is defined to mean a collection of elements tied together in a logical way. Modules can be related to a specific type of protocol activity. For example, a vital signs module can comprise a blood pressure element, a heart rate element, a body temperature element, and a respiratory rate element. Modules can also be related to an agreement or transaction and can contain the text of the agreement along with associated data including translations of the text of the agreement, video content related to the agreement, and questions and answers about the agreement.

The term "element" is defined to mean a set of information describing a particular procedure or function for the protocol-defined medical care. Each element may contain, but is not limited to, the following information: results, data collection fields, best practice information, required resources and staffing, regulatory guidance, level of evidence for the recommendation, timing, predecessors, and dependencies. For example, the blood pressure element may contain, but is not limited to, information on the results (e.g., systolic and diastolic blood pressure measurement), data collection fields including ranges (e.g., the systolic blood pressure field should contain three digits and can range from 70 to 220), best practice performance standards (e.g., "The subject should be lying down for at least 5 minutes before obtaining the measurement. Use the dominant arm and place the blood pressure cuff half-way between the elbow and the shoulder"), required resources and staffing (e.g., mercury sphygmomanometer and nurse), regulatory guidance and requirements (e.g., Good Clinical Practice (GCP) guidelines for data collection), level of evidence for the recommendation (e.g., Level A—randomized, double-blind, placebo-controlled clinical trial has shown that supine (lying down) is better than sitting up for blood pressure measurement), timing/predecessors/dependencies (e.g., perform the blood pressure measurement only after the subject has been sitting quietly for five minutes and before the scheduled blood draw). Another example of an element can be a basic health questionnaire element that may comprise a list of questions for a doctor to ask a subject to assess the basic health of the subject.

The term "library" is defined to mean a collection of protocols, modules, and elements. A given collection may be organized and referenced and searchable. The library may organize the modules and elements in a way that related modules and elements are connected to each other and logically available when specific choices are made. For example, if the vital signs module is chosen, it may already contain the blood pressure and heart rate elements, and the vital signs module may be connected to and/or recommend the anthropomorphic measurement module (including weight, height, waist, and hip measurements).

The terms "study", "clinical trial", "clinical study", "medical research", "clinical research", and "clinical investigation" are used interchangeably and are defined herein to mean any clinical trial to collect data for health interventions, epidemiology, or outcomes. Clinical research as defined by the NIH includes patient oriented research (e.g., studies of mechanisms of human disease, studies of therapies of human disease, clinical trials, studies to develop new technology related to disease, etc.), epidemiological and behavioral studies (e.g., the distribution of disease, the factors that affect health, and how people make health related decisions), and outcomes and health services research (e.g., studies seeking to identify the most effective and efficient interventions, treatments, and services) [see reference (1)].

The terms "doctor", "investigator", "nurse", "nurse practitioner", "physician assistant", "clinical research coordinator", "research assistant", "research staff", "clinical practitioner", and "medical professional" are used interchangeably and are defined herein to mean any clinical practitioner who interacts with a patient for the purposes of performing a clinical visit and/or collecting medical or clinical data.

The terms "subject", "research subject", "clinical trial participant", "person with health condition", and "patient" are used interchangeably and are defined herein to mean any person who interacts with a clinical practitioner (e.g., medical professional) for the purpose of collecting medical or clinical data.

The term "protocol procedures" can include, but is not limited to, answering medical questions; performing a physical examination; dispensing and/or taking an investigational study product; filling out a diary, scale (e.g., survey question with a range of 1-10), or questionnaire; eating a specific study related food or beverage; measuring a body function such as temperature, blood pressure, and blood sugar; measuring an anthropomorphic measurement such as weight; performing a test such as an EKG or stress test; and collecting a specimen such as urine, saliva, stool, semen, or blood. Compliance with a protocol includes, but is not limited to, compliance with the required steps of the protocol, following the correct sequence or timing of procedures, collecting data in the correct manner, compliance with Good Clinical Practice (GCP), compliance with Standard Operating Procedures (SOPs), and compliance with best practice methods for performing the required procedures.

The term "medical procedure" is defined to mean a course of action intended to achieve a result in the care of persons with health problems. A medical procedure with the intent of determining, measuring, or diagnosing a patient condition or parameter is also called a medical test. Medical procedures can include, but are not limited to, analytic laboratories, surgeries, pathology procedures, dermatology procedures, gastroenterology procedures, cardiology procedures, obstetrics procedures, gynecology procedures, oncology procedures, orthopedics procedures, pediatrics procedures, internal medicine procedures, sleep medicine procedures, rehabilitation procedures, radiology procedures, and urology procedures.

The term "video" is defined to mean a 2D video, a 3D video, a hologram, a video recording, and/or a holographic recording. For example, it may include, but is not limited to, any recording of video, audio, or still image or combinations thereof made by a camera, holographic recording device, and/or microphone The terms "video", "video record", and "video recording" are used interchangeably and are defined herein to mean any video, holographic, audio, still image or combinations thereof of recordings made by a camera and/or a microphone.

The terms "recording device", "camera", "video camera", "still camera", "holographic recording device", and "microphone" are used interchangeably and are defined herein to mean any device that records sound and/or light and/or image.

The terms "connection", "network connection", and "network" are used interchangeably and defined herein to mean any wired or wireless network connection. Examples of network connections include, but are not limited to, Wi-Fi, BLUETOOTH®, WiMAX, MIT-2000, Satellite, ZIGBEE®, cellular network, infrared identification (RFID), local area network (LAN), wide area network (WAN), and remote or near-field communication between an electronic device and either another electronic device or the Internet.

The terms "data", "clinical data", "medical data", and "clinical trial data" are used interchangeably and are defined herein to mean data collected during a clinical trial.

The terms "contract", "disclosure", "terms of service", "consent form", and "waiver" are used interchangeably and are defined herein to mean an agreement between two parties.

The terms "contract provider" and "agreement provider" are used interchangeably and are defined herein to mean the party that creates and/or offers the agreement or contract.

The terms "contract signer" and "agreement signer" are used interchangeably and are defined herein to mean the party that agrees to the agreement or contract offered by the contract provider.

The term "document" is defined to mean either a paper document or an electronic document.

The terms "clinical research visit", "clinical visit", "medical visit", "scheduled visit", "unscheduled visit", "examination", "exam", "clinical activity", and "clinical encounter" are used interchangeably and are defined to mean any meeting or interaction between at least one medical professional and a subject or patient to collect clinical data.

The term "disease management" is defined to mean a system of coordinated health care interventions and communications for populations with conditions in which patient self-care efforts may be significant. For example, it may be concerned with common chronic illnesses and the reduction of future complications associated with those diseases (Wikipedia, "Disease Management (Health)", (accessed Jun. 10, 2011)). The term "disease management" is also defined to mean a medical care related to a protocol, pathway, or guideline.

The term "wellness management" is defined to mean a preventive medical care related to a protocol, pathway, or guideline. For example, wellness management may include, but is not limited to, corporate and workplace wellness management systems that may be designed to help employees maintain and improve their mental and physical health with the goal of reducing absenteeism and presenteeism [see reference (2)].

The term "medical guideline" is defined to mean a clinical guideline, clinical protocol, or clinical practice guideline and may be a document with the aim of guiding decisions and criteria regarding diagnosis, management, and treatment in specific areas of healthcare.

The term "clinical pathway" is defined to mean tools that may be used to manage the quality in healthcare concerning standardization of care processes. For example, a clinical pathway may include, but is not limited to care pathways, critical pathways, integrated care pathways, and care maps.

The term "order sets" is defined to mean standardized sets including, but not limited to, medical orders, clinical decision support rules, and/or quality measures The term "care plans" may include, but are not limited to, a plan of care, medical workflow, medical pathways, and medical guidelines.

The terms "setting", "medical setting", "clinical setting" and "clinical trial setting" are used interchangeably and are defined herein to include, but are not limited to, ambulatory care facilities such as medical offices, clinics, ambulatory surgery facilities, hemodialysis facilities, rehabilitation facilities, drug abuse treatment facilities, family planning centers, hospitals, home health agencies, hospices, clinical trials clinics, oncology clinics, pharmacies, adult day healthcare centers, assisted living facilities, nursing homes, residential health care facilities, disease management programs, wellness management programs, and others.

The terms "mHealth" and "mobile health" are used interchangeably and are defined herein to mean incorporation of mobile telecommunication, multimedia technology, and mobile communication devices for delivery of medical health services and clinical trials services. Examples of mobile health devices include, but are not limited to, sphygmomanometers, glucometers, pulse oximeters, thermometers, pedometers, electrocardiograms, biofeedback devices, actimeters, optical refractors, stethoscopes, pulmonary function test devices, urine analyzers, and exhaled gas analyzers. These devices may be used in or out of a medical setting and may communicate with each other or with the systems and units described within this document.

The term "progress bar" is defined to mean a component in a graphical user interface that may be used to convey progress of a task or sequence of events. More specifically for example, it may be a display of the sequence of expected steps that may occur based on the protocol-defined medical care or any other set of services or visit that can be medically related or non-medically related. The progress bar can also include a calculation of the amount of time and/or number of steps completed and the amount of time and/or number of steps remaining.

The terms "authentication", "validation", and "verification" may be used interchangeably and are defined herein to mean confirmation of the identity of an individual. Authentication may be used in combination with validation (the process of finding or testing the truth of something) and verification (confirmation that an individual who is requesting something over the system has in fact made that request).

The term "biometrics" is defined to mean methods for uniquely recognizing individual human beings based on one or more intrinsic physical or behavioral traits. For example, identification authentication may involve, but is not limited to, facial recognition, fingerprint recognition, retinal scans, voiceprint recognition, iris scans, typing biometrics, hand and finger geometry, signature verification, ear geometry, olfactory biometrics, and behavioral biometrics. The identification authentication may serve as a security protocol to provide data access only to authorized users.

The terms "institutional review board", "ethics review board", and "ethics committee" are used interchangeably and are defined herein to mean an ethical review body for a clinical trial.

The term "regulatory agencies" are defined to mean country-specific regulatory agencies with responsibility and authority for approval of new drugs. For example, regulatory agencies may include, but are not limited to, the United States Food and Drug Administration (US FDA), Health Canada, sFDA, TGA, etc.

The term "audit trail" is defined to mean a sequence of steps supported by proof, thereby documenting the real processing of a transaction flow. For example, the audit trail may include, but is not limited to, identity information as well as date and time stamp and location stamp (via GPS).

The terms "product", "study product", "study drug", "investigational new drug", "investigational study product", "investigational study drug", "investigational drug", "investigational product", "investigational medicinal product", "prescription drug", "over-the-counter drug", "dietary supplements", "herbal products", "medical foods", "functional foods", "foods", "medical devices", "prescription medication", "non-prescription medication", pills, "powders", "inhaled medications", "injectable medications", "clinical study drugs", "creams", "gels", and "cosmetics" are used interchangeably and are defined herein to mean any product, device, treatment or therapy used by any person or animal for the diagnosis of a disease or health-related condition, treatment of a disease or health-related condition, prevention of a disease or health-related condition, reduction of the risk of a disease or health-related condition, cure of a disease or health-related condition, to affect or maintain normal structure or function of the body, to maintain a health status, to promote wellness, for cosmetic purposes, or to be studied, evaluated, or tested in a clinical trial.

The terms "source", "source record", "electronic medical source", and "electronic medical record" are used interchangeably and are defined herein to mean any audio, video, hologram, text, input data, mHealth input, laboratory result input, or medical procedure input related to the performance of protocol-defined medical care. For example, the term "electronic source" is defined according to the FDA as meaning source documents and source data for which the original record and certified copies are initially captured electronically [see reference (3)].

The term "electronic record" is defined herein to mean any combination of text, graphics, data, audio, pictorial, or other information represented in digital form that is created, modified, maintained, archived, retrieved, or distributed by a computer system in accordance with 21 CFR 11.3(b)(6).

The term "eCRF" is defined herein to mean a vehicle used to assemble all the data from different electronic and paper-based systems and used to make possible the capture and organization of the (generally) diverse data in a manner that satisfies the study protocol and that enables the data to be systematically reviewed and analyzed by, for example, investigators, other authorized parties, and the FDA [see reference (3)].

The terms "eProtocol" and "electronic protocol unit" are used interchangeably and are defined to each mean a system for the creation of a protocol which relates to the designing, performing, and managing of a protocol-defined medical care such as clinical trials.

For clarity purposes, the terms "eSource" and "eSource unit" are used interchangeably with "electronic medical source" and describe the electronic medical source methods and systems of the present disclosure adapted for enhancing collection of data from medical or clinical research visits.

The term "eLibrary" or "electronic library unit" is defined to mean a system or unit for the collection of protocols, modules, and elements. A given collection may be organized and referenced and searchable. The eLibrary may organize the modules and elements in a way that related modules and elements are connected to each other and logically available when specific choices are made. For example, if the vital signs module is chosen, it may already contain the blood pressure and heart rate elements, and the vital signs module may be connected to and/or recommend the anthropomorphic measurement module (including weight, height, waist, and hip measurements). For example, the eLibrary may contain a store through which one may purchase elements, modules, or protocols.

The terms "eConsent", "eContract" and "electronic consent and contract unit" are used interchangeably and are defined herein to mean a system for ensuring that an agreement between two or more parties is properly understood and acknowledged and to ensure that the parties comprehend the terms of the agreement.

The term "eCompliance" or "electronic compliance unit" is defined herein to mean a system for electronically assuring compliance to guidance or requirements of a protocol or plan.

The term "ePRO" or "electronic patient reported outcomes unit is defined herein to mean a system for the electronically capture of self-reported outcomes such as diaries, scales, and/or questionnaires. The electronically captured self-reported outcomes may include video, audio, holography, text, and touch-screen input. The ePRO may include electronic devices connected to the eProtocol and eLibrary units and configured for the capture of outcomes.

The term "eInventory" is defined herein to mean a system for tracking the non-study product inventory for a clinical trial. The tracking includes, but is not limited to, tracking of the distribution, location, and status of inventory as required by the eProtocol, eSource, eCompliance, and eConsent systems. Examples of inventory may include, but are not limited to, medical supplies (e.g., blood draw needles), office supplies (e.g., printer ink), laboratory supplies (e.g., blood draw kits), study specimens (e.g., blood, urine, stool, saliva), documents (e.g., the latest version of the informed consent document or patient handouts), food (e.g., study specific meals), equipment (e.g., ECG machines), and tools (e.g., blood pressure cuffs).

The term "eStudy Product" is defined herein to mean a system for tracking the inventory of experimental study products for a clinical trial as required by the eProtocol, eSource, eCompliance, and eConsent systems.

The term "eSponsor" is defined herein to mean a system through which authorized representatives of the sponsor of the clinical trial can obtain access to real-time information on the progress of the clinical trial (including enrollment data) and can access blinded, but validated, data related to the clinical trial.

The term "eMonitor" is defined herein to mean a system through which an authorized study monitor can access study data, video, holography, and audio for review. Monitors can also perform Source Data Verification (SDV) by comparing the original video, audio, or holographic recordings to the entered study data or the voice to text transcription into study data.

The term "eRegulatory" is defined herein to mean a system through which documents and filings required for institutional review boards and regulatory agencies are completed, tracked, and sent according to the requirements of the regulatory authorities and according to the requirements of the eProtocol, eSource, eCompliance, and eConsent systems.

The term "eFinance" is defined herein to mean a system through which financial requirements, contracts, contract milestones, and payments related to the clinical study can be completed, tracked, and sent according to the requirements of the eProtocol, eSource, eCompliance, and eConsent systems as well as the requirements of the regulatory authorities.

The term "eRecruitment" is defined herein to mean a system through which the criteria and management of subject enrollment into the clinical study is managed according to the requirements of the eProtocol and eSource systems and according to the requirements of the regulatory authorities.

The term "eData" is defined herein to mean a system through which the data requirements, database structure and organization, and data access security for the database for the clinical study are managed according to the requirements of the eProtocol and eSource systems and according to the requirements of the regulatory authorities.

The term "eStatistics" is defined herein to mean a system through which the statistical plan and actual performance of statistical analysis is managed according to the requirements of the eProtocol and eSource systems and according to the requirements of protocol and the regulatory authorities.

The term "eInvestigator" is defined herein to mean a system through which doctors and their associated medical practices or research sites are recruited for participation in a clinical trial or other protocol-defined medical care activities. As the doctors and their sites complete the contracts, regulatory filings, startup activities, and enrollment of patients, their performance may be tracked and compared to benchmarks for the particular study or against historical data. An individual doctor's performance can be aggregated or analyzed individually for a single study or longitudinally across multiple studies.

The term "eLaboratory" is defined herein to mean a system for the management and tracking of biological specimens that are sent to analytical laboratories as well as the return of the results of the testing of these specimens according to the requirements of the eProtocol and eSource systems and according to the requirements of the regulatory authorities.

The term "eProcedure" is defined herein to mean a system for the management and tracking of medical procedures as well as the return of the results of these medical procedures according to the requirements of the eProtocol, eSource, and eCompliance systems and according to the requirements of the regulatory authorities.

The term "ePatient" is defined herein to mean a system for the management of the identity and identity characteristics for subjects (potential, actual, current, and past) of clinical trials. The system may also manage the enrollment of subjects in clinical trials and manage the dates of their enrollment and termination in the clinical trial. In doing so, the ePatient system, in conjunction with the eConfirm, eConsent, eSource, and eCompliance systems, can ensure that a subject does not concurrently participate in multiple clinical trials.

The term "eDocument" is defined herein to mean a system for the management of all documents required for the clinical trial according to the requirements of the eProtocol, eSource, eConsent, eInventory, and eCompliance systems and according to the requirements of the regulatory authorities.

The term "eSafety" is defined herein to mean a system for the management of safety reports, adverse events, events of clinical interest, and data safety monitoring boards for the clinical trial according to the requirements of the eProtocol, eSource, eConsent, and eCompliance systems and according to the requirements of the regulatory authorities.

The term "eCTMS (eClinical Trial Management System)" is defined herein to mean a system for the management of the schedules for patients enrolled in the clinical trial. eCTMS may set the parameters of the schedule in compliance with the requirements of the eProtocol and eSource systems. eCTMS can send reminders through the ePRO and eCompliance systems, and can verify attendance through the eConfirm system.

The term "eConfirm" and "electronic identity and attendance confirmation unit" are used interchangeably and are defined herein to mean a system for the management of fraud minimization. The system may manage fraud minimization by recording, logging, verifying and authenticating the identity, attendance, and/or activity of a person.

The term "eUnit" is defined herein to mean any of the systems or units describe above in this section of the present disclosure. Each eUnit may comprise software, firmware, middleware, and hardware adapted to perform the steps or functions of the systems, where the software may be loaded onto the hardware locally or be accessed via a network connection but running remotely on a server.

System Description

Referring now to FIG. 1, shown therein is a system (100) comprising an electronic library unit (110), an electronic protocol unit (120), a database (130), a server, an electronic medical source unit (140), an electronic patient reported outcomes (PRO) unit (150), an electronic compliance unit (160), an electronic identity and attendance confirmation unit (170), and an electronic consent and contract unit (180). The system also comprises of an electronic consent/contract database (130), a patient information database (130), and a clinical data database (130), each of which resides on one server or combination of servers. The electronic library unit (110) itself is comprised of modules, where each of these modules is, in turn, itself comprised of elements. The various electronic units can be used alone or in combination with one or more electronic units as a system as shown in FIG. 1. Each of these units (110, 120, 140, 150, 160, 170, 180) will be described in detail in various paragraphs throughout the present disclosure.

For example, the electronic consent and contract unit (180) can be used alone in a variety of settings. A mortgage loan office can carry an electronic device containing loan agreements and contracts to the client to execute such agreements. In such a case, the electronic consent and contract unit (180) is implemented independently.

In another example, the electronic consent and contract unit (180) can be utilized in combination with the electronic identity and attendance confirmation unit (170) such that if, by way of example and not of limitation, a subject is involved in a long term clinical study, an initial informed consent agreement may be executed using the electronic consent and contract unit (180). However, if during the course of the long term clinical trial, the clinical trial sponsor should require an amended informed consent agreement, the electronic identity and attendance confirmation unit (170) can first confirm that the clinical trial subject who showed up for his or her appointment that day is in fact the same person that started the study, and then the electronic identity and attendance confirmation unit (170) can interact with the electronic consent and contract unit (180) to determine that an amended informed consent agreement is available and required for this particular subject to sign. At this point the electronic consent and contract unit (180) would provide the amended informed consent agreement according to processes described in detail in various paragraphs throughout the present disclosure According to the exemplary system shown in FIG. 1, the electronic library unit (110) can be configured to operate with the electronic protocol unit (120) and/or the electronic consent and contract unit (180) directly. The electronic protocol unit (120) can be configured to operate with the electronic library system (110), the electronic medical source unit (140), the electronic consent and contract unit (180), the electronic compliance unit (160), the electronic patient reported outcomes unit (150), and the electronic identity and attendance confirmation unit (170).

Figure 4A:
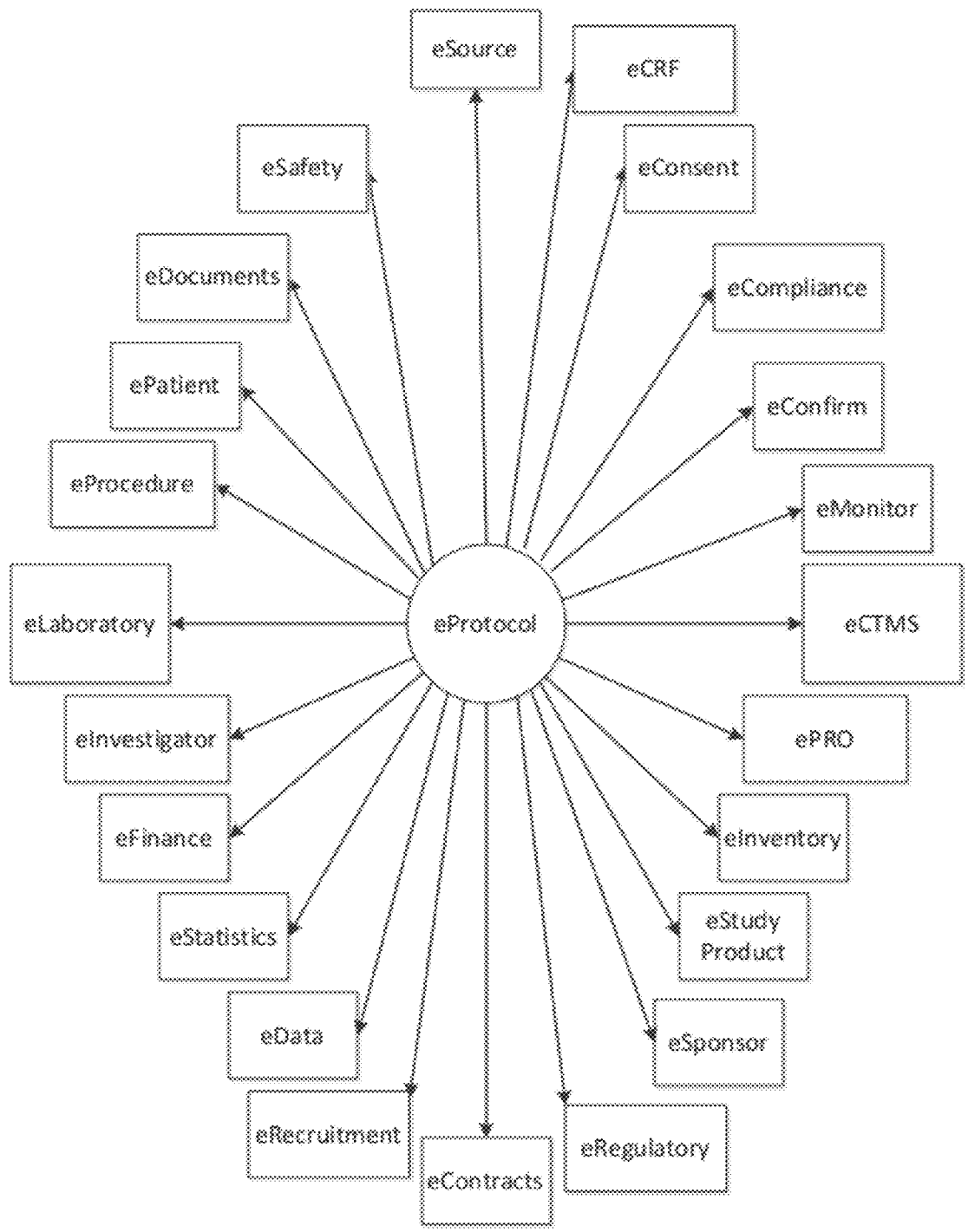
FIGS. 4A-4G show flow charts of an exemplary electronic protocol unit of the present disclosure.

As shown in FIG. 4A, the electronic medical source unit (140) can be configured to operate with the electronic compliance unit (160), the electronic patient reported outcomes unit (150), the electronic consent and contract unit (180), and the electronic identity and attendance confirmation unit (170). Furthermore, the electronic identity and attendance confirmation unit (170) can be configured to operate with the electronic consent and contract unit (180), the electronic medical source unit (140), the electronic compliance unit (160), and the electronic patient reported outcomes unit (150) and can also be configured to send information to and receive information from a server.

Further, the electronic patient reported outcomes unit (150) can be configured to operate with the electronic compliance unit (160). An example use of these combinations can be in a clinical trial setting. Furthermore, a database (130) can be configured to be a storage center such as a cloud or server (290 in FIG. 2) where data from the electronic units, or eUnits for example as shown in FIG. 1 (110, 120, 140, 150, 160, 170, 180) are uploaded and/or downloaded. For example, the electronic patient report outcomes unit (150) can store data internally in the electronic device when being used by the subject. However, the data stored in the electronic device can be uploaded, for example, by way of physical or wireless connections (e.g., Internet, BLUETOOTH®, cable) as desired and/or at predetermined time intervals.

While embodiments, examples, and/or aspects of the present disclosure have been described showing one or more systems comprising a plurality of elements, the person skilled in the art will understand that different combinations or sub-combinations of such elements (or even such elements taken by themselves) also fall within the purview of the present disclosure. For example, with continued reference to FIG. 1, a facial recognition element or application is described as part of the electronic compliance unit (160), but the facial recognition element or application can be used alone (need not be part of the electronic compliance unit (160)), or may be used with another unit such as the electronic consent unit (180). As another example, an electronic progress unit, to be described later in the present disclosure, that includes a progress bar and timer is described within the electronic medical source unit (140), but it may an application that may be used alone or with another unit such as the electronic consent unit (180).

Hardware and Software

It is noted that the methods and systems described in the present disclosure may be implemented in hardware, software, firmware, middleware, or combinations thereof. Features described as blocks, modules, applications, units, or components may be implemented together (e.g., in a single device such as a tablet computer) or separately (e.g., as separate connected devices such as a tablet computer and a camera). In the case of separately connected devices, the separate connected devices may be connected by wired and/or wireless connections via a network such as a local area network (LAN), Wi-Fi, BLUETOOTH®, WiMAX, MIT-2000, Satellite, cellular network, wide area network (WAN), or the Internet.

The software portion of the methods and systems of the present disclosure may comprise a computer-readable medium that comprises instructions that, when executed, perform, at least in part, the various described methods in the present disclosure. The computer-readable medium may comprise, for example, random access memory (RAM), non-volatile memory (NVM), a hard drive, or a cloud storage. The computer-readable medium that comprises instructions to be executed may be accessed locally or remotely via a connected network. The instructions may be executed by a processor (e.g., a microprocessor, a microcontroller, a digital signal processor (DSP), an application specific integrated circuit (ASIC), a standard logic integrated circuit, or a field programmable logic array (PLD, FPGA, etc.)). The processor may be local or accessed remotely via a connected network. The processor may be a single processor integrated in a device (e.g., a tablet computer or a server) or be a number of distributed processor (e.g., a cloud or a network of computers or one or more racks of blade servers).

Figure 2:
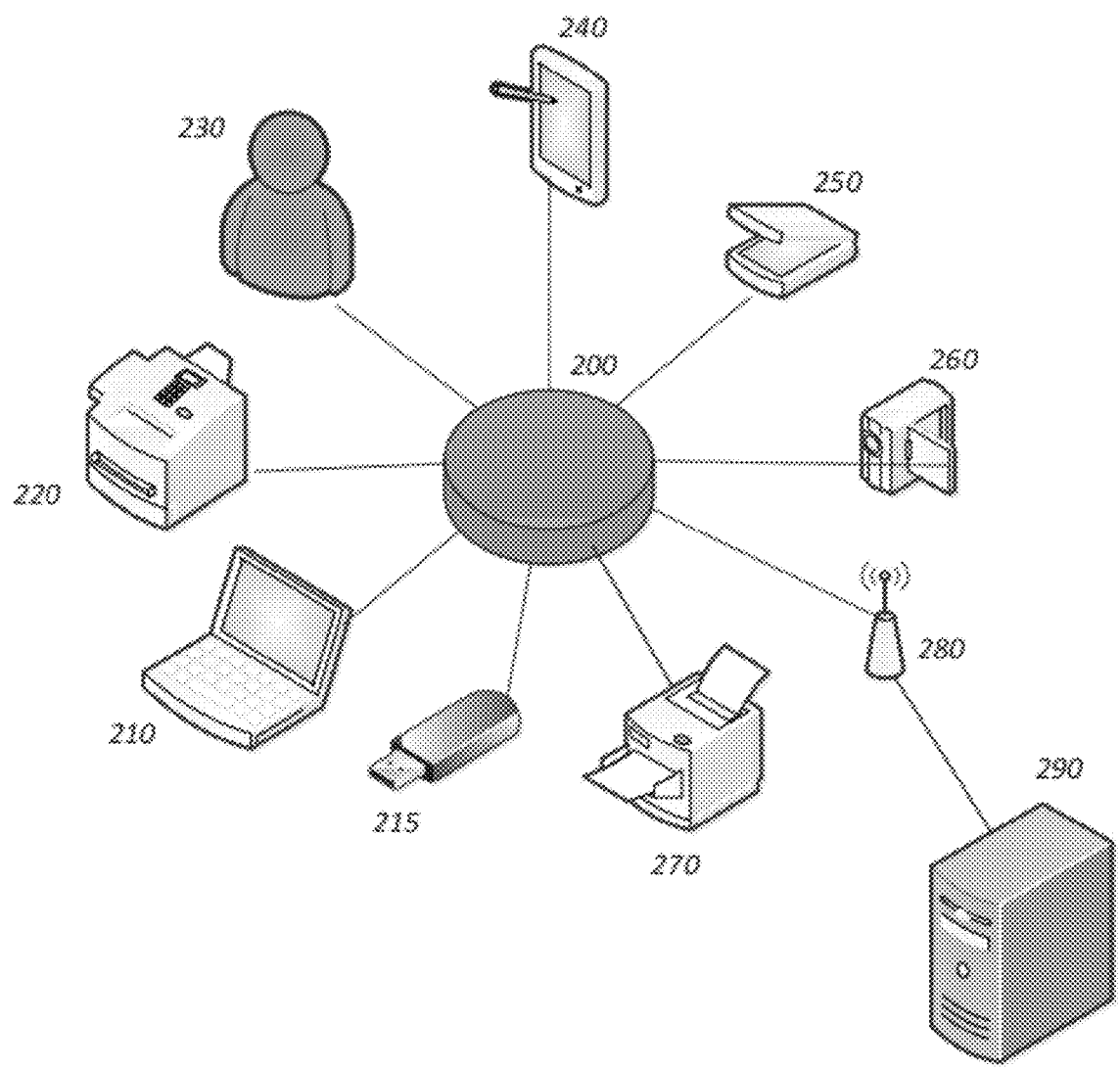
FIG. 2 shows a diagram of hardware components of an exemplary system of the present disclosure.

Referring now to FIG. 2, shown herein is an exemplary hardware system (200) in an embodiment of the present disclosure for execution of the various methods of the present disclosure. The exemplary hardware system (200) comprises a processor (210), which may form part of a computer, a computer-readable storage medium (215), a medical measurement device (220), a biometric device (230), a user interface device (240), an interface to receive data from medical assessments (250), a camera (video, audio, or holographic) (260), a network connection (280) for the system (200), a server or cloud (290) and, optionally, a printer (270). The hardware system (200) may comprise more than one of any of the foregoing components.

Each component (210, 215, 220, 230, 240, 250, 260, 270, 280, 290) may be a distinct device and may comprise additional hardware and/or software components. For example, the hardware system (200) may comprise a camera (260), and the camera (260) may comprise its own processor and wireless connection to the system (200). As another example, the user interface device (240) may comprise a touch screen equipped with internal accelerometers that respond to shaking and rotations of the touch screen.

One or more components may be combined into a single device that may form all or part of the hardware system (200). For example, the processor (210), the interface device (240), the camera (260), and the network connection (280) may be combined in one embodiment of the present system (200) in a common housing such as that of a tablet computer.

The processor (210) of the system (200) may serve to exercise common control of operations of the components associated with the system (200). The processor (210) can be either a conventional processor, in which case instructions for operation of the other components of the present system (200) are stored in memory or in other computer readable storage media (215), or alternatively the processor (210) can be a special purpose processor with instructions included in read-only memory or other hardware.

In one embodiment, the processor (210) is included in a computer, and a display device such as a computer screen can be associated with the computer. Alternatively or in addition, the processor can be placed in communication with an external computer or other device for inputting clinical trial information, which can be stored in memory in the system (200) and/or directly uploaded from the system (200) to a clinical trial database.

The hardware system (200) may also contain one or more computer-readable storage medium (215) for the storage of instructions or storage of a local database for the execution of the methods of the present disclosure. The computer-readable medium (215) may comprise, for example, random access memory (RAM), non-volatile memory (NVM), a hard drive, or a cloud storage.

The system (200) can be configured to collect data directly (via wired or wireless connection) from a variety of medical measurement devices (220). The measurement device (220) may be a mobile health (mHealth) device including but not limited to a sphygmomanometer, glucometer, pulse oximeter, thermometer, pedometer, electrocardiogram, biofeedback device, actimeter, optical refractor, stethoscope, pulmonary function test device, urine analyzer, and exhaled gas analyzer. Each of these mHealth devices may have its own processor and communication hardware to send measurement results to the system (200).

The medical devices (220) can be devices used in a clinic for making clinical study related measurements. For example, one medical device (220) may be a scale that transmits the weight of remaining test material brought back by a subject into the system (200). As another example, the medical device (220) can be an automated pill counter to be used to count the number of pills given to and received back from a subject.

Alternatively, or in addition to receiving data from the medical devices (220), the system (200) may be configured to collect data and/or reports directly or indirectly from laboratory and external medical facilities using an interface for medical assessments (250). The laboratory and external medical facilities include but are not limited to analytic laboratories, surgeries, pathology, dermatology, gastroenterology, cardiology, obstetrics, gynecology, oncology, orthopedics, pediatrics, internal medicine, sleep medicine, radiology, and urology. The medical assessments (250) may include analytical laboratory tests, specialist assessments, procedures, reports, and others.

In one embodiment, the Health Level 7 (HL7) standard for healthcare informatics interoperability can be utilized for secure data transfer between these laboratory and medical assessments (250) and the system (200). Collection of data or assessments from the external laboratories and medical facilities can be by direct data importation or indirectly by scanning in a paper report, which may involve optical character recognition or manual capture of data fields.

As yet another example, the medical assessments (250) can be from in-house lab instruments at the clinical trial site that can communicate results of measurements directly to the system (200). For example, an instrument for the medical assessments (250) may transmit glucose level in a urine sample of a subject to the system (200).

The hardware system (200) may comprise a biometric device (230), which can be one or more of a number of known devices that can accurately identify an individual based on one or more unique, intrinsic, generally physical trait, such as facial features and geometry, fingerprint scanning, retinal or iris scanning, keyboard typing patterns, hand and finger geometry, ear geometry, signature characteristics, olfactory biometrics, behavioral biometrics, or voiceprint recognition. The biometric device (230) may be a separate device or combined with existing video component, audio component or other components of the system (200).

The user interface device (240) of the hardware system (200) may be one or more of a monitor, computer screen, holographic screen, touch pad, keyboard, mouse, trackball, joystick, pointing stick, stylus, touch screen, light pen, eye tracking device, steering wheel, paddle, dancepad, laser pen, camera, microphone, voice-to-text, and text-to-voice conversion system, augmented reality device, screenless display, interactive display, and others for a user to interface with the system (200). The user interface device (240) may be a screen, a display, a screenless display, a touchscreen, or a interactive display. A screenless display may comprise a visual image display (e.g., hologram, virtual reality goggles, heads up display), virtual retina display (e.g., retinal projector), or synaptic interface.

An exemplary interface device (240) is a camera (260) that can provide still or moving pictures or holograms and be used to verify the identity of subjects, doctors, and study materials, and to provide general source recording of medical and clinical activities. The camera (260) may also comprise microphone for audio receiving and recording capabilities.

The hardware may, optionally, include a printer (270) for printing out documents on paper or on other media.

The network connection (280) of the system (200) can, in some embodiments, be a physical connection to a communications port, which places the hardware system (200) in electronic communication with a database (130), as previously described in relation with FIG. 1, housed in a server or cloud (290). In other embodiments, the network connection (280) may be a wireless transceiver such as a Wi-Fi or a BLUETOOTH® network device. The network connection (280) can be a local area network (LAN), Wi-Fi, BLUETOOTH®, WiMAX, MIT-2000, satellite, cellular network, wide area network (WAN), or the Internet.

With reference to FIG. 1, examples of databases (130) include an electronic library (eLibrary) database (130), an eConsent/eContract database (130), a patient information database (130), and a clinical data database (130). The network connection (280) can be adapted to download data and applications from the server (290 in FIG. 2) and to upload data, patient information, and/or signed agreements from the eUnits to the servers (290 in FIG. 2). Each eUnit may run applications locally on the system or remotely via a network on a server via a number of protocols as described more later in this section.

With reference back to FIG. 2, the processor (210) can send data collected by the system (200) to one or more servers or clouds (290) either through a direct connection or over a network. The server or cloud (290) can be utilized for storing additional information and long term storage of data and can be located and/or accessible locally or remotely. The server or cloud (290) may house one or more databases (130 in FIG. 1).

A number of the components of the system (200) may be combined into a single electronic device such as a computer, portable computer, tablet computer, smart phone, game console, e-book reader, holographic device, television screen, or video screen. The electronic device may comprise hardware for wireless communication, video capture, writing capture (e.g., a touch screen), memory for execution of applications, memory for storage of applications and data, display (e.g., a screen or a hologram), and input (e.g., a keypad or keyboard). The device may comprise hardware that performs more than one function, such as a touch screen that may serve as both display and input functions.

The electronic device, which comprises part of all of the system (200) may comprise hardware for wired or wireless communication, audio, video or holographic video capture, writing, or other input capture (e.g., a touch sensitive screen or other haptic feedback including but not limited to motion sensors or acoustic radiation pressure sensors for holographic interaction), memory for execution of applications, memory for storage of applications and data, display (e.g., a screen or a hologram), and input (e.g., a keypad or keyboard).

The electronic device may connect to various components within the system (200) via network connection such as Wi-Fi, near-field communication/proximity connectivity, BLUETOOTH®, ZIGBEE®, radio frequency identification (RFID), local area network (LAN), WiMAX, MIT-2000, Satellite, cellular network, wide area network (WAN), or the Internet.

In an embodiment of the present disclosure, the system (200) may comprise one or more electronic devices utilizing the ARM (Advanced RISC Machine) architecture. For example, the electronic device may be an IPAD®, IPHONE 4®, and IPOD TOUCH 4® utilizing the Apple 4® ARM.

The architecture of the electronic device may determine an operating system software to be utilized by the system. For example, the ARM architecture can be configured to run Apple Inc.'s iOS® (iPhone Operating System). The system (200) may be adapted to run on one or more versions of an operating system software such as the iOS® 4.3.3 and the iOS® 5.0.

The operating systems software may enable features that may be used as part of the systems and methods of the present disclosure. For example, the iOS® has a user interface that is based on a concept of direct manipulation by means of multi-touch gestures that may include swipe, tap, pinch, reverse pinch, and slide. The iOS® can also enable the electronic devices, such as the IPAD®, IPHONE®, and IPOD TOUCH®, which have internal accelerometers, to respond to shaking and rotations in 3D.

In addition, choice of the system architecture and operating system software may direct the instructions to perform the functions as described in the present disclosure to be written and compiled using one or more compatible compilers, development environments, and/or programming languages. For example, the instructions adapted to be used with the iOS® and the ARM architecture may be written and compiled using the iOS® SDK (software development kit), Xcode as the development environment for iOS® SDK, and Objective-C programming language as a platform for development.

In another embodiment of the present disclosure, the system (200) may run a set of instructions or an application on a remote server, and the application on the remote server may be accessed by utilizing an electronic device such as an IPAD® via a wireless or Wi-Fi network. The Wi-Fi network can, for example, be using the IEEE 802.11 b, g, or n standard to define speed, range, and security of the wireless network. The Wi-Fi enabled devices can connect to the Internet when within range of a wireless network or access point connected to the Internet. An access point or hotspot may typically have a range of around 20 meters indoors and longer outdoors with multiple overlapping access points. The electronic device may thus connect to the server, which itself is connected to a network with access to the Internet.

An exemplary connection to run an application of the present disclosure on a remote server accessed by an electronic device can begin by the electronic device sending a query for the availability of the server in the network. The electronic device and the server may each have device names that identify each in the network. Whenever the electronic device or server is in the network, the device name or names may be visible and discoverable. When the electronic device finds the server, then a request to connect can be made upon selection. The server, in response, can send confirmation of the establishment of a connection. Once the connection is established, electronic devices can download data from or upload data into the server, run applications from or on the server, or query information from the server depending on the nature of the request from the electronic devices. The connection established between the server and the electronic device may persist until the connection is lost or disconnected.

The electronic device of the present system may also access the server by utilizing the TCP/UDP (Transfer Control Protocol/User Datagram Protocol). The server may have a program adapted to process TCP/UDP requests from the electronic devices.

Requests from the electronic device may also be processed by a server utilizing HTTP (Hyper Text Transfer Protocol). For this setup, a web server may accept the HTTP requests from the electronic devices. The web server may act as a central node in the connection.

Connections may be made between electronic devices or components of the system, for example, via a Wi-Fi network as previously described. One electronic device may find another electronic device on the network by identifying the name of an electronic device and requesting connection. The connection established between devices may persist until the connection is lost or disconnected. Other methods of connecting electronic devices or components of the system, such as the camera to the tablet computer, may include BLUE-TOOTH® and 3G cellular network.

A medical device (220), such as a scale, pill counter, or an mHealth device may connect to another electronic device of the system, such as a tablet computer, through BLUETOOTH® or Wi-Fi connection capabilities. A Wi-Fi connection in this case may follow similar steps as those described in the previous paragraphs. For a BLUETOOTH® connection, the medical device (220) may have a device name for the BLUETOOTH® connection that is discoverable once the BLUETOOTH® capability is active. When the electronic device turns on its BLUETOOTH® connection, the device scans for active BLUETOOTH® devices that are within range to be visible or discoverable to the device. The electronic device may request connection to a visible medical device (220) and the medical device (220) may send a passcode for confirmation from the electronic device for connection confirmation. Once confirmed, the medical device (220) is connected to the electronic device until the connection is lost or disconnected.

Wi-Fi enabled medical devices (220) may also utilize the TCP/UDP protocol to connect to the electronic device. Utilization of the TCP/UDP protocol may include use of an API (Application Programming Interface) from the manufacturer of the medical device (220) for communication. BLUETOOTH® and Wi-Fi connections may differ in at least the range of connectivity. BLUETOOTH® connections typically have a range of less than 100 m while Wi-Fi can work as long as connection is available. In addition, BLUETOOTH® connections are generally only used for device connections and not typically used for Internet access.

Other possible methods of connectivity or network connection between two components or between a component and a server of the system of the present disclosure may include the THUNDERBOLT®, which is a wired connection that combines data, video, audio, and power.

Other wired or direct connection methods include use of USB 3.0 and USB 2.0. Other wireless methods include use of VoWi-Fi, which is a technology that combines Wi-Fi and VoIP (Voice-over IP) technology; 4G cellular network; and 3G cellular network.

The above paragraphs describe combination of components and functionalities involved in performance of medical or clinical visits and other interactions in connection with the present methods.

Example 1

People are often faced with reading an agreement (e.g., contracts, terms of service, consent form, medical agreement, clinical agreement, financial agreement, business agreement, government agreement, waiver, disclosure, etc.) and signing such agreement stating their understanding to the terms when executing an agreement or a transaction. However, it is a common problem that such people do not necessarily read their agreement and simply just sign their name where they are asked to sign. Even in cases where they in fact do read the agreement, it can be difficult to determine if they really comprehend what they have read.

By way of example and not of limitation, in certain medical settings (e.g., human clinical trials), the version of the contract (or consent form) can change from time to time due to changes in the clinical trial protocol associated with the human clinical trials. A subject in the clinical trials who has already signed a consent form may be required to sign a new informed consent document during the same study. It can become increasingly difficult for research staff to ensure that a proper version of the document is being used.

The embodiments of the present disclosure describe methods of ensuring a transaction agreement between two or more parties is properly understood and acknowledged. Furthermore, the methods described can provide proof that such parties actually comprehend the agreement.

The term "agreement" is defined herein to refer to, but is not limited to, disclosures, contracts, terms of service, consent forms, or waivers between two or more parties. Such terms are also used interchangeably herein in the present disclosure. The term "agreement provider" is defined herein to refer to the party that creates, selects, or provides the agreement while the term "agreement signer" is defined herein to refer to the party that agrees to the agreement. For example, the agreement provider can be a clinical trials doctor who can select an informed consent document (agreement) from a list of possible informed consent documents and the agreement signer can be a clinical trial subject who will provide his or her consent to participate in the clinical trial by signing the informed consent document.

In an embodiment of the present disclosure, an agreement provider can use an electronic device (e.g., computer, portable computer, tablet computer, smartphone, game console, e-book reader, holographic device, television screen, video screen) that can be configured to display the contract, observe the agreement signer viewing the contract, ensure the agreement signer comprehends the agreement, and electronically record and document the process in which the agreement signer (e.g., a clinical trials subject) goes through when agreeing to the agreement on the electronic device. The combination electronic device and contract is referred to herein as an "electronic consent and contract unit" and can also be referred to interchangeably herein in the present disclosure as an "eConsent/eContract unit". With reference to the eConsent/eContract unit in the present disclosure, the terms "agreement signer" can be used interchangeably with the term "subject" to describe specific exemplary implementations of the electronic consent and contract unit.

More in particular, the electronic device can be configured, by way of example and not of limitation, to display a written agreement or playback an audio, video, or holographic recording of the agreement (or summary of the agreement) on a display such that the agreement signer can read or playback the agreement at his or her own pace. For example, if the agreement comprises a plurality of pages of written documents, the signer can choose to scroll forward or backwards as desired. If the agreement comprises an audio, video, or holographic recording, the signer can choose to replay the playback and/or stop the playback as desired.

Figure 3A:
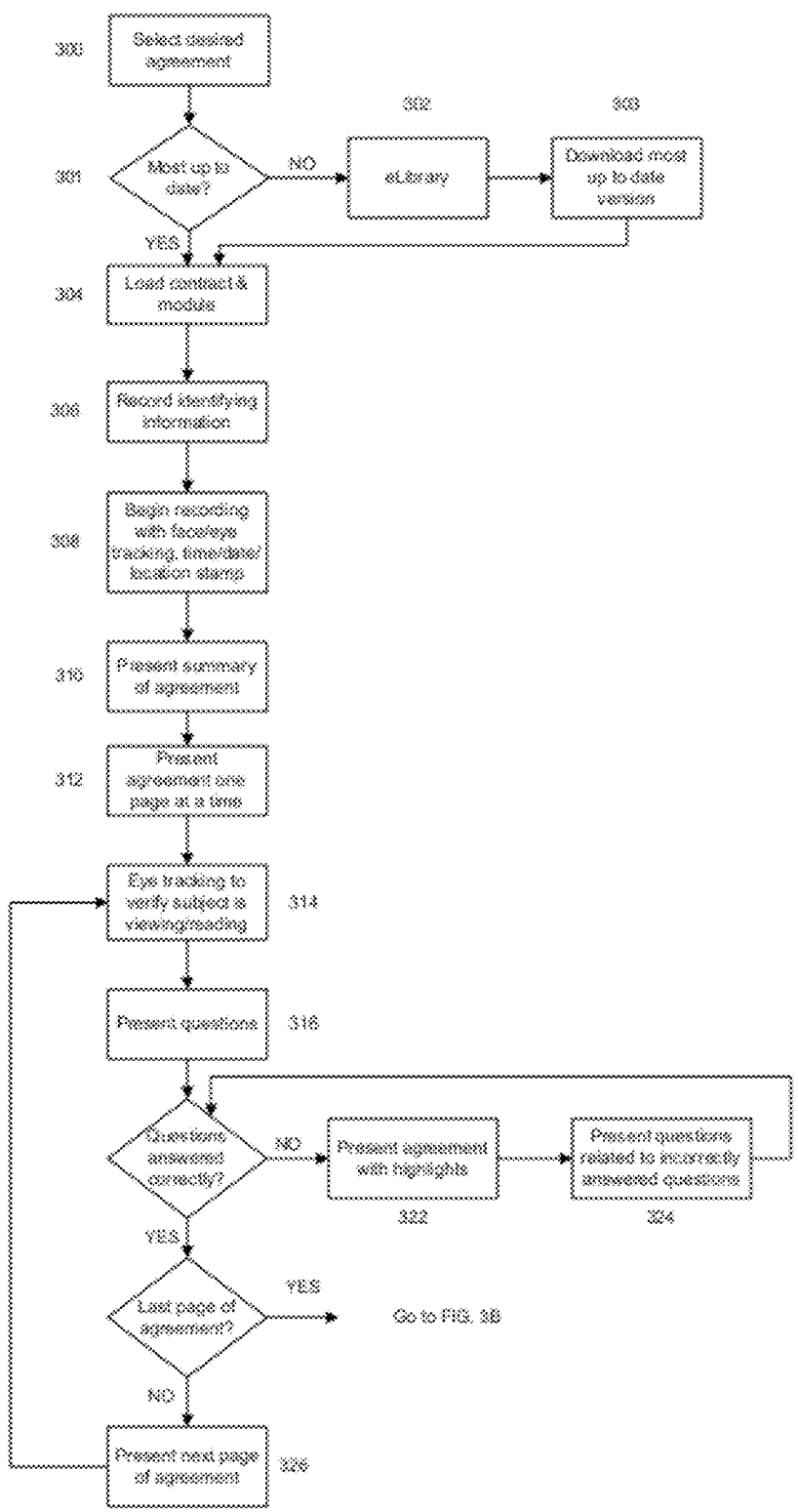
FIGS. 3A-3I show flow charts, diagrams, and displays of an exemplary electronic confirmation unit and an electronic consent/contract unit of the present disclosure.
Figure 3B:
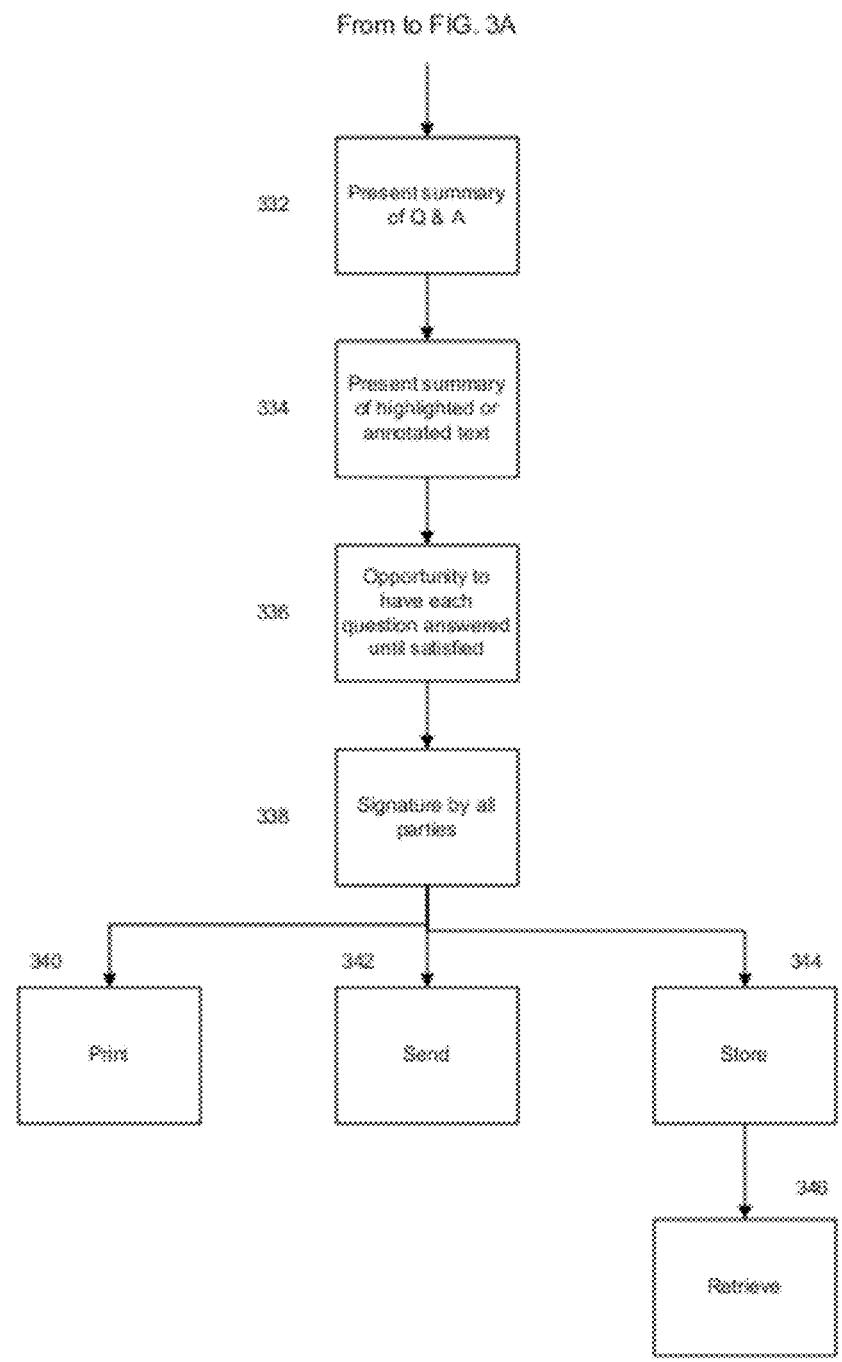
Figure 3C:
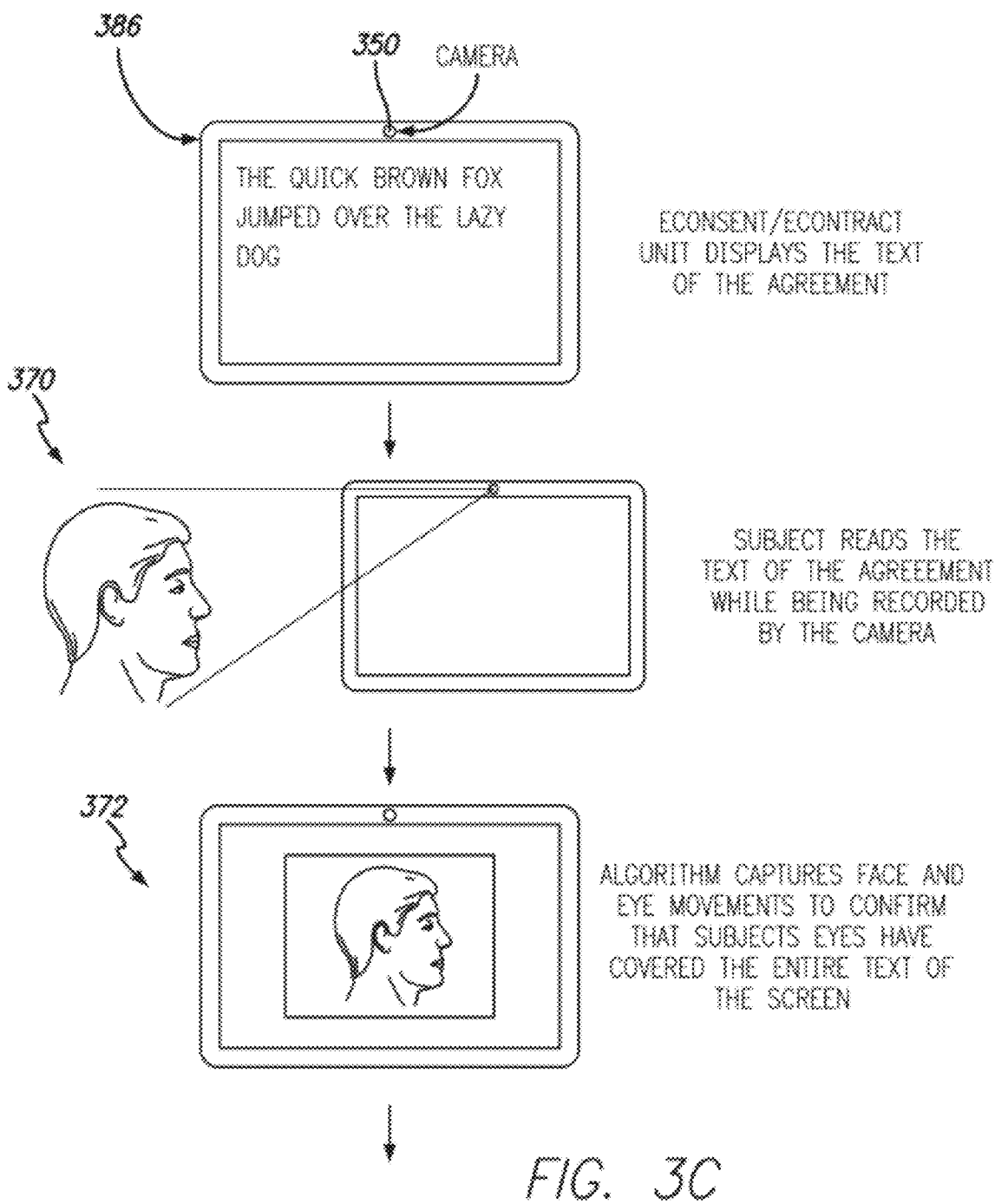
Figure 3D:
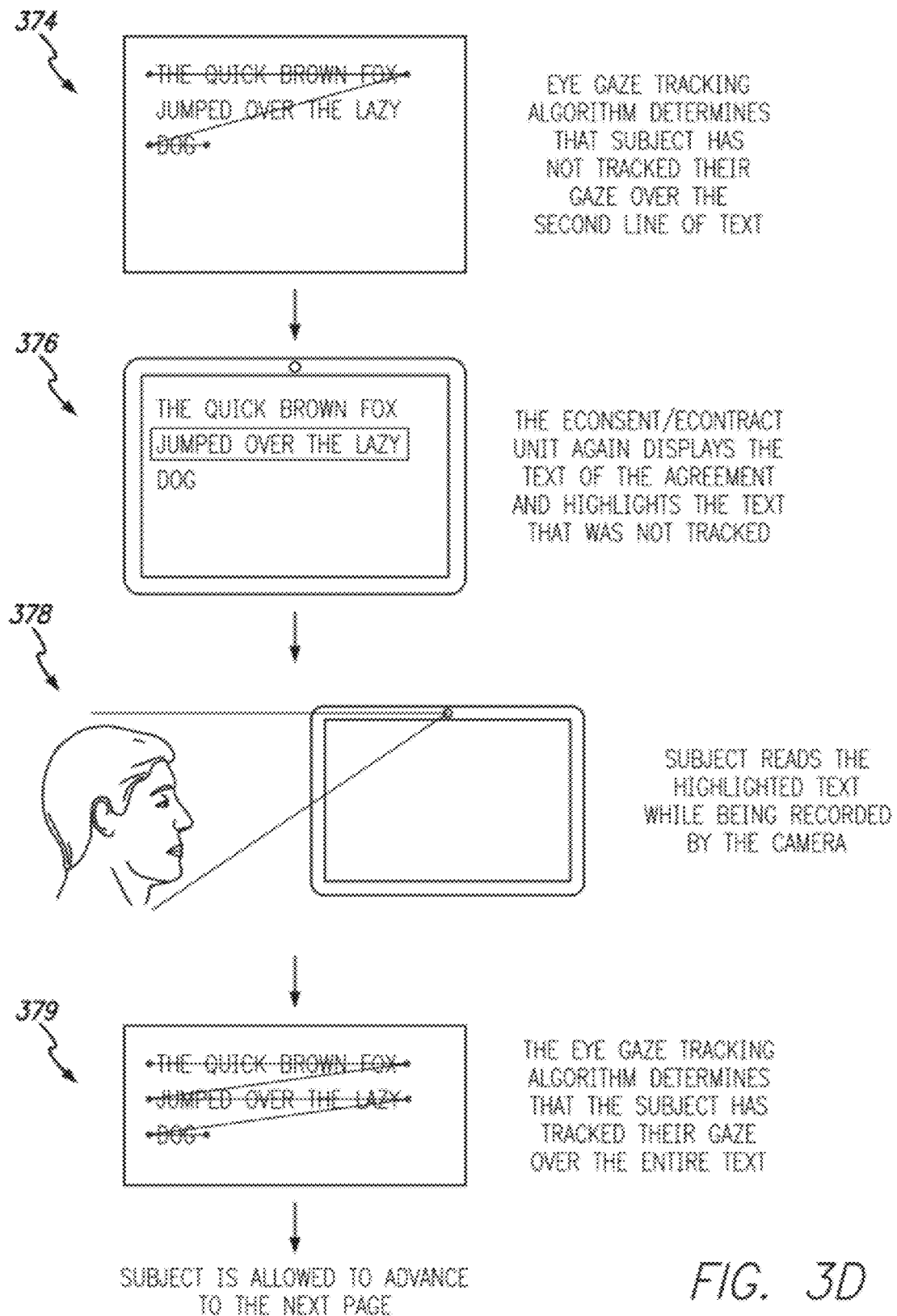

In an embodiment of the present disclosure as shown in FIGS. 3A-3B, the agreement provider can select a desired agreement (300) from a list of available agreements. The agreement provider can then load the desired agreement/module (including but not limited to the text of the agreement; multiple language translations of the text of the agreement; videos, audio recordings, games, questions, answers, and other associated data concerning the contract) onto the electronic device or use the electronic device to access the same content on a remote system.

Upon selection of the desired contract (300), the electronic device can be configured to determine if the contract and module are the most up-to-date version (301) by communicating with, for example, a master library (e.g., eLibrary Database Server (302)), as described in further detail in later paragraphs. The electronic device will compare the locally residing version of the contract and module against the eLibrary Database Server (302). If the locally residing version is the most up-to-date version, then that version of the contract and module can be loaded on the electronic device (304). If there is a more recent version of the contract on the eLibrary Database Server (302), then that more recent version of the contract can be downloaded to the electronic device (303) via wired or wireless methods including, but not limited to, Wi-Fi, BLUETOOTH®, WiMax, Satellite, MIT-2000, and millimeter wave. Once downloaded to the electronic device, the more recent version of the contract can be loaded on the electronic device (304).

Figure 3E:
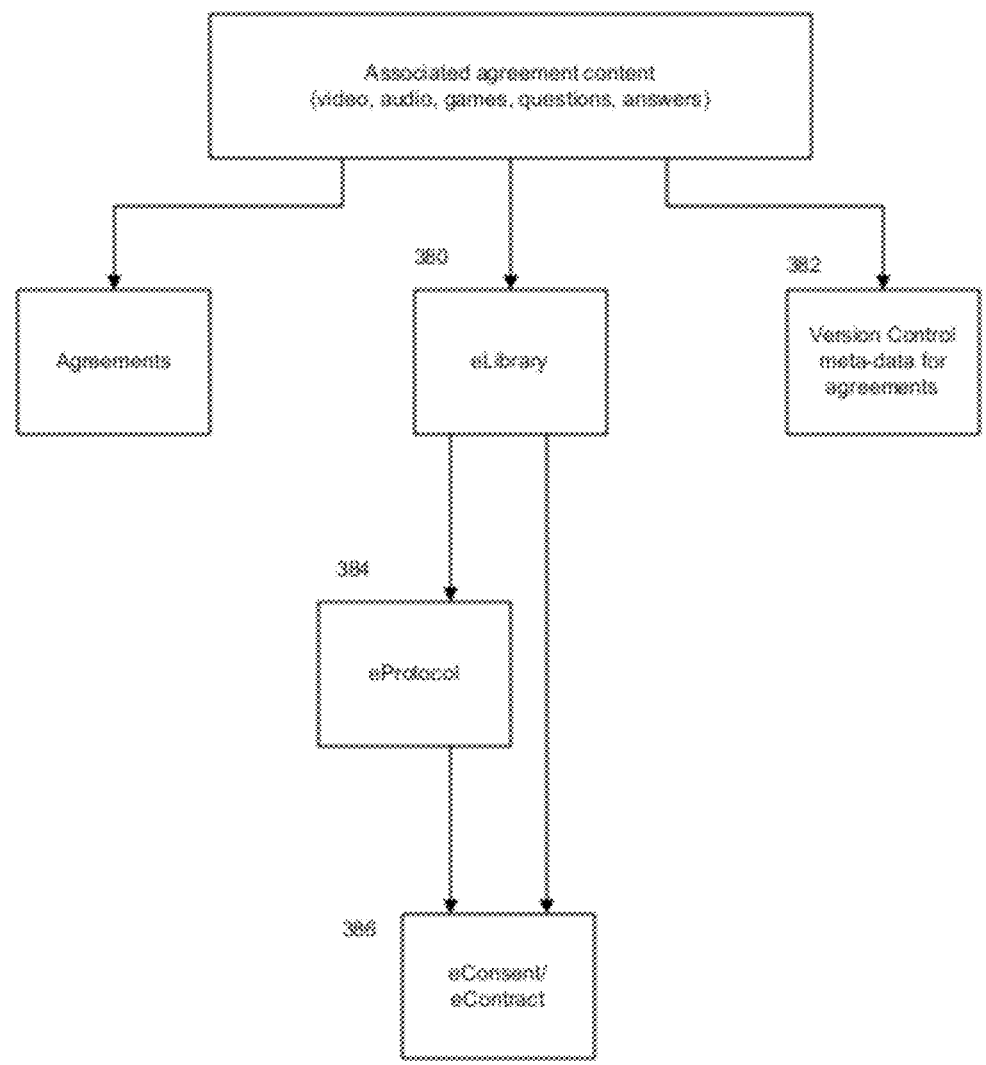
Figure 3F:
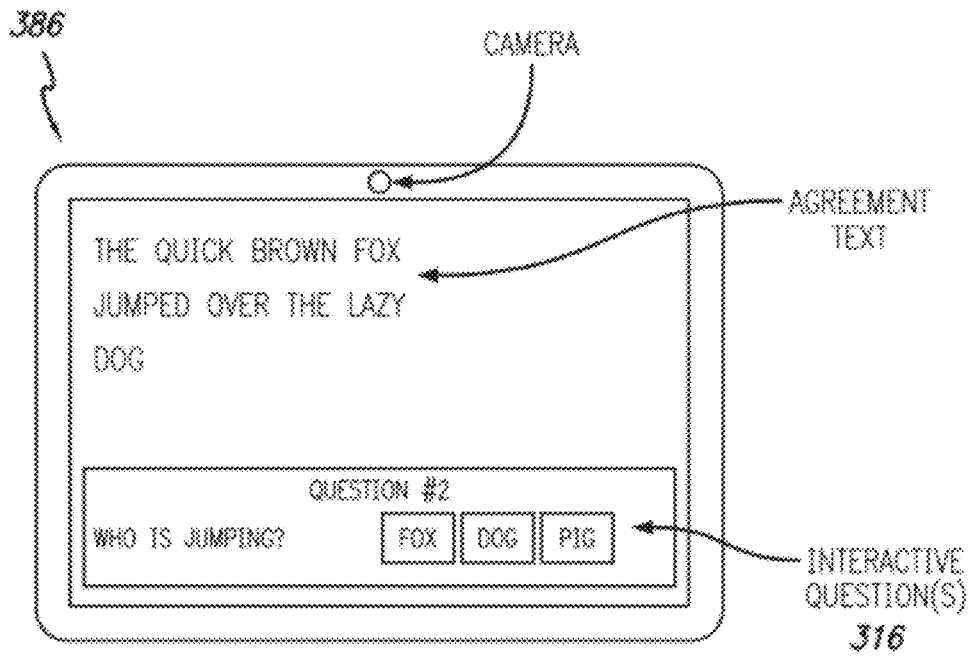
Figure 3G:
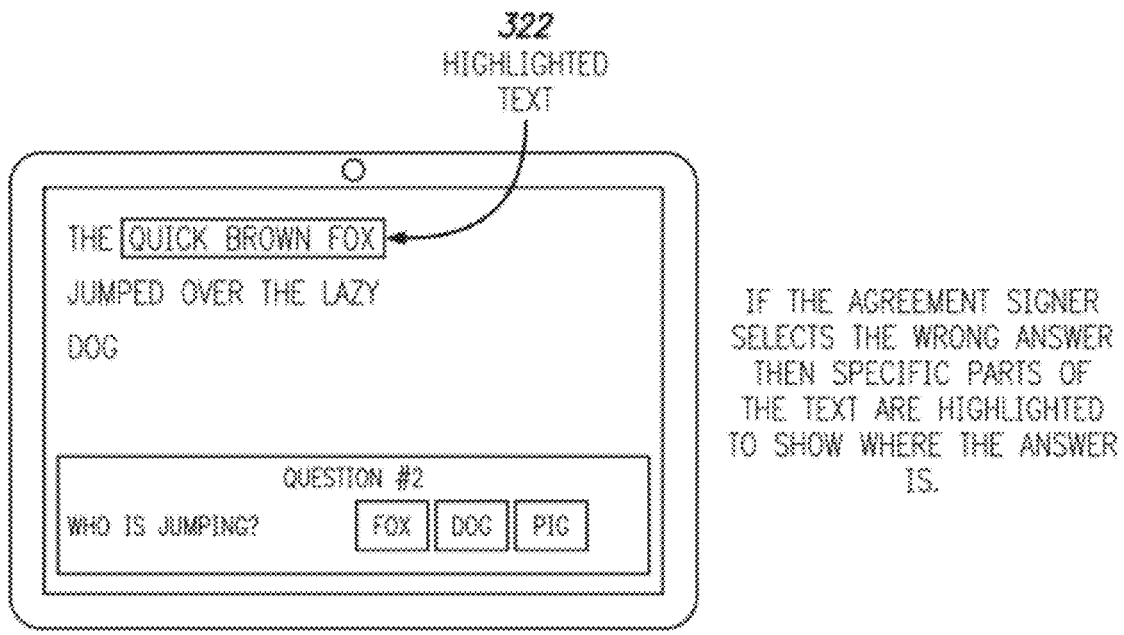

Agreement "elements" can include the text of the agreement; multiple language translations of the text of the agreements; associated videos, audio recordings, games, questions, answers, and other associated data concerning the contract. The multiple elements can be combined to make up an agreement "module". As shown in FIG. 3E, such elements and modules can be stored in the eLibrary unit (380), similar to that described in the following paragraphs for an electronic protocol unit (384). The modules comprised of several elements form the complete contents of the agreement, which can ultimately be loaded on the electronic device and executed with the eConsent/eContract unit (386). The modules can also have associated meta-data to indicate version numbers (also referred to herein as Version Control (382)) of the agreement that can be used, for example, to ensure the most recent version of the elements and/or modules are being used.

By way of example and not of limitation, the user can be a clinical trial doctor who can use the eConsent/eContract unit (386) to select an appropriate Informed Consent Document (ICD) for a volunteer subject desiring to participate in a clinical trial. Since a clinical trial can last from a few months to several years, and the Informed Consent Document can be frequently amended and/or revised numerous times during the period of the clinical trial, the clinical trial doctor has the responsibility to ensure that the correct and most up-to-date agreement of the consent form has been signed by the clinical trial subject. The Version Control meta-data (382) stored in the eLibrary (380) and associated with the Informed Consent Document can ensure that the clinical trial doctor is using the most current and approved version of the agreement document. Once the appropriate Informed Consent Document is selected, the agreement document and associated information can be either transmitted from the eLibrary (380) to the eProtocol unit (384) and then to the eConsent/eContract unit (386) or can be transmitted directly from the eLibrary (380) to the eConsent/eContract unit (386) in order to perform the Informed Consent Process and then have the Informed Consent Document signed by both the clinical trial doctor and the subject.

Referring back to FIGS. 3A-3B, the agreement signer will then record and authenticate his or her identifying information (306) including but not limited to name, social security number, driver's license number, passport number, other government identification documents, address, date of birth, video/audio/still images, and biometric authentication (e.g., face recognition, fingerprints, retina scan, voiceprint, iris scan, typing biometrics, hand and finger geometry, signature verification, ear geometry, olfactory biometrics, and behavioral biometrics). Identity cards (including but not limited to driver's license, passport, or other government identification documents) can also be recorded, swiped, or scanned to confirm or further confirm identity of the agreement signer.

As the signer is viewing the agreement as shown in FIGS. 3A-3E, a video recording device such as a video camera or a webcam (350) can be configured to visually record (308, 370) the signer viewing the agreement. Moreover, the video recording device (350) can be integrated to communicate with the electronic device and further arranged to track face, eye, and gaze movement (372) of the signer. The camera (350) can be integrated into the electronic device and/or can be separate from the electronic device and controlled by the electronic device. For example, the camera (350) can determine if the signer's face remains in view of the camera (350) and can automatically move to track the face of the signer to ensure that the face remains within the view of the camera (350).

By way of example and not of limitation, if the agreement is a written agreement, the electronic device (with a camera (350)) can determine if the signer has actually read the text on the page by following the movement of the signer's eye such that the eye movement corresponds with the wording, sentences (374), images, and/or video that are being read by the signer on the display.

As a consequence of eye and gaze tracking, the signer can be prevented from proceeding to the next page/section of the contract if the eye and gaze tracking algorithm on the eConsent/eContract unit (386) suspects that the signer did not actually read all of the text on a written agreement or did not watch an entire video. A message can be displayed, thereby prompting the signer to read the entire written agreement. Alternatively, the electronic device can also be configured to prevent the signer from advancing to the next page until the eye and gaze tracking confirms that the agreement signer has read the entire section.

In the case of a video or holographic agreement, the camera (350) can observe the eye movement to ensure the signer is at least watching the display that is showing the video agreement. The time, date, and location (e.g., GPS location) of the video recording of the signer can be captured and attached as meta-data to the recording itself.

Once the recording begins, a summary of the contract can be presented (310) in text, audio, video, slideshow, hologram, or game format. Following the summary presentation of the agreement, the eConsent/eContract unit (386) can be configured to present a single page or section (video, presentation slide, audio, hologram, or game) of the contract to the signer. The device can be further configured to enable the signer to increase or decrease the size of the page or section (e.g., zoom in, zoom out), select the signer's desired language for the page or section to be displayed, and/or have the text read aloud as audio. The page or section of the contract can be adapted to be viewed from beginning to end and can be scrolled back and forth as many times as the signer desires.

Figure 3H:
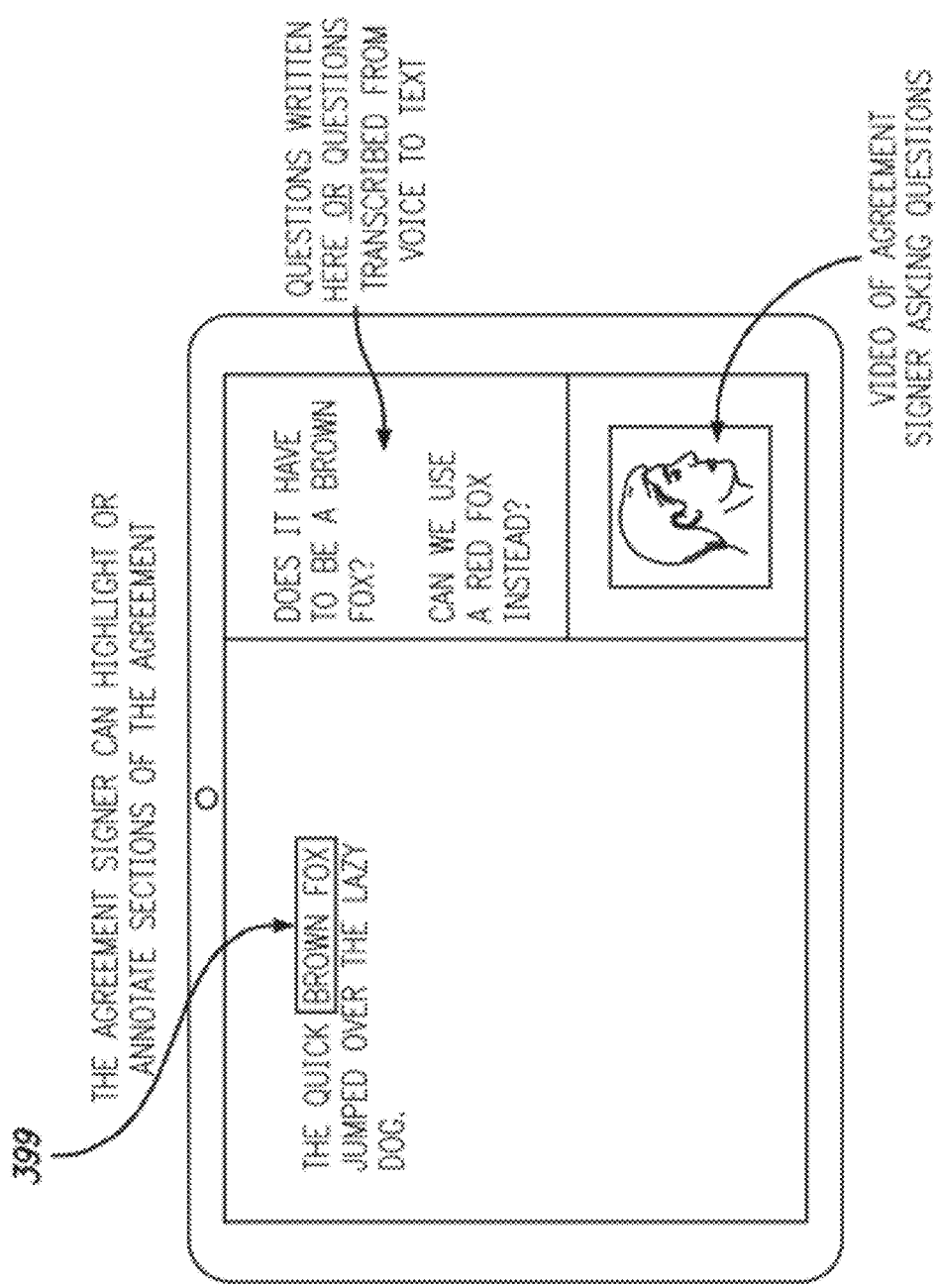
Figure 3I:
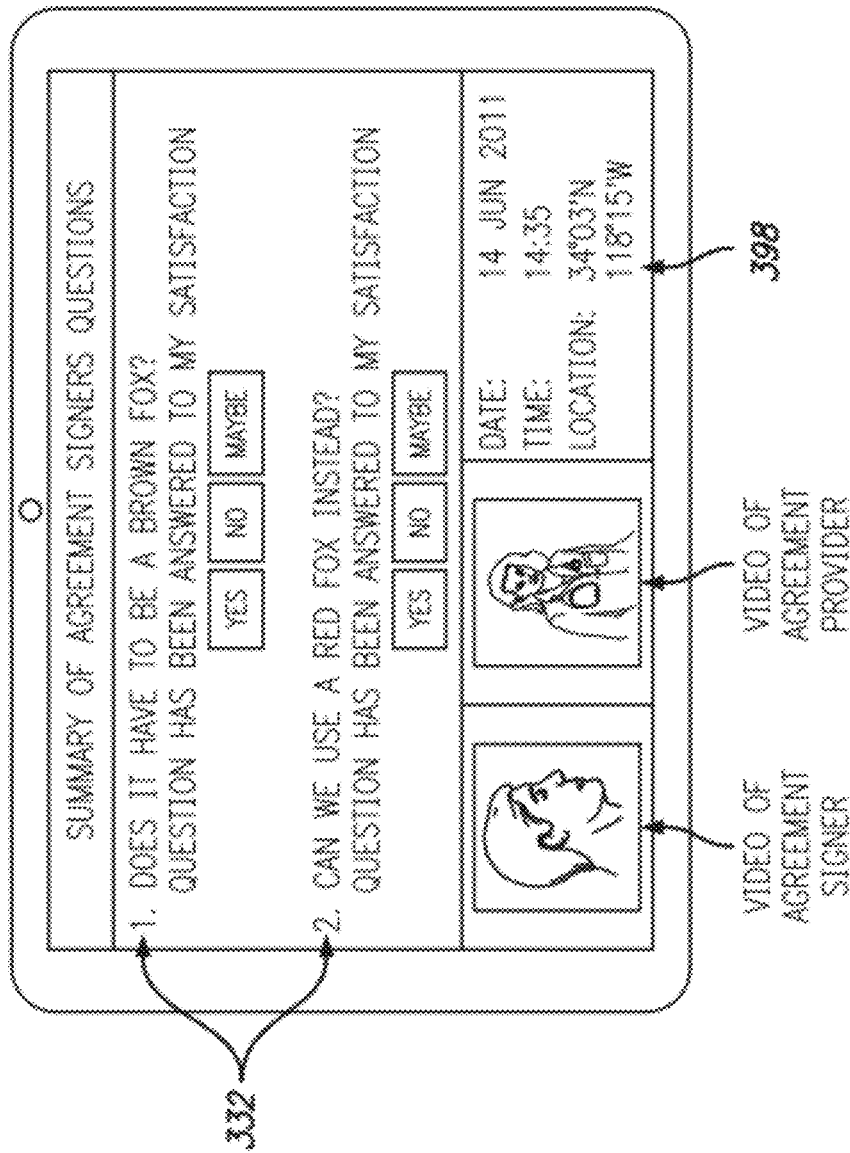

The sConsent/eContract unit (386) can be further configured such that the signer can highlight (399 in FIG. 3H) sections of the text of the presentation and take notes on the electronic device regarding, for example, any questions (334 in FIG. 3I) that he or she may have about the contract. Such notes can be written directly on the electronic device (e.g., using a stylus), spoken verbally and recorded by audio, video, or holographic recording, and/or can be annotated directly within the text or sections of the contract in question.

According to another example of the present disclosure, as the signer begins to read the agreement, a camera (350) embedded in the eConsent/eContract unit (386) (or an external camera controlled by the electronic device) tracks the signer's eye movement (314) to determine whether or not the subject is actually reading the text of the agreement. If the signer is suspected of not reading the text, then the signer can be prompted to read the text again. If the eye movement shows that the signer is reading the text, then the subject will be allowed to advance to the next page when ready. Once the signer advances to the next page, the camera (350) again tracks the signer's eye movement and determines whether or not the signer is reading the text.

According to another embodiment, when the signer finishes reading the text, the electronic device can be configured to ask a series of interactive questions (316) to test the signer's knowledge of the agreement. Such questions can be displayed on the eConsent/eContract unit (386) as text, presented as a video, presentation slide, audio, hologram, or game. The answers to such questions can be obtained by typing, clicking buttons, or speaking the answers (using voice recognition speech to text conversion to interpret the answer).

If the subject answers the interactive questions incorrectly, the electronic device can be configured to re-display specific sections of the text of the contract where the answers are located. Pertinent sections of the text can also be highlighted (322). The signer is then asked the same question(s) again (324). Guiding the subject to the location of the correct answer within the contract can help the signer understand and/or comprehend the contents of the agreement.

If the signer answers the questions correctly, the electronic device can be configured to present the signer with the next sequential page of the text or section of the contract (326). The question and answer sequence (316, 322, 324) can be repeated until the end of the contract is reached. Once the end of the contract is reached, the signer can be presented with a summary of the questions and correct answers (332) to further enforce his or her understanding of the contract.

According to another embodiment, in the case where the signer indicated he or she had questions concerning specific sections of the text or the contract, the electronic device can be configured to address those questions for the signer. For example, the electronic device can be configured to present a list of sections the text or the contract that were annotated by the signer with notes (334) while reading, viewing, or listening to the contract. The signer can then be provided with an opportunity to have each question answered and addressed by the contract provider (336). Such conversation between the subject and the contract provider can be recorded on video using a camera (350) embedded within or connected to the electronic device.

According to yet another embodiment, the electronic device can be configured to allow both the contract provider and the signer to electronically sign and authenticate their agreement to the contract (338). The electronic signature can be, for example, a digital signature directly on the electronic device using a stylus pen. The electronic signature can also be provided by use of a biometric identification process. The signed contract can be printed (340) on a printer, sent electronically (342) by email or other electronic messaging system, and/or stored (344) for later retrieval (346). Such signature can be considered a valid, legally binding, enforceable, and authenticated signature to the agreement.

According to yet another embodiment, the eConsent/eContract unit (386) can be configured to allow both the agreement provider and the signer to record verbal acknowledgement to a written agreement. For example, the agreement signer can proceed through all of the steps described above; however, instead of a digital or biometric signature, the eConsent/eContract unit (386) can be configured to record (using audio, video, and/or holography) the agreement signer and/or the agreement provider providing their verbal agreement to the terms and conditions of the agreement.

In another embodiment, the eConsent/eContract unit (386) can be configured to record a verbal agreement between the agreement provider and the signer by recording an electronic or digital signature to that agreement. For example, the eConsent/eContract unit (386) can be configured to record (using audio, video, and/or holography) the agreement provider describing the terms and conditions of the agreement, and then allow both the agreement provider and the agreement signer to electronically sign and authenticate their agreement to the contract.

In another embodiment, the eConsent/eContract unit (386) can be configured to record a verbal agreement between the agreement provider and the signer and to record verbal acknowledgement by both parties to the verbal agreement. For example, the eConsent/eContract unit (386) can be configured to record (using audio, video, and/or holography) the agreement provider describing the terms and conditions of the agreement, and then record the agreement signer and/or the agreement provider giving their verbal agreement to the terms and conditions of the agreement.

When the signed contract is stored (344), the following information and data can be stored together as well: an initial authentication of the signer (e.g., photographs of the signer, biometric identification); an audio, video, and/or holographic recording showing the signer reading/viewing the contract, time/date/location stamp (398 in FIG. 3I) of the amount of time the signer spent going through the entire contract as well as the amount of time the signer spent on each individual text or video sections of the contract; the eye and gaze tracking results documenting the signer's eye movement corresponding to the text or video on a per-page or per-section basis; the list of interactive questions asked and the answers given by the signer; the number of tries it took for the signer to correctly answer each question; and the highlighted text and annotated notes as well as the audio, video, and/or holographic recording of the contract provider answering such questions and concerns.

The contract and all of the described additional data can be stored on the electronic device and/or on local and/or remote databases via, for example, mass storage device, media storage, random access memory, read only memory, magnetic recording, magnetic storage, solid state drive, floppy disc, optical disc drive, internet, hard drive, server, recordable media, memory cards, CD, DVD, tape, tape library, RAID system, magnetic tape drive, magneto-optical disc drive, drum memory, punched tape, holographic memory, removable media, and non-removable media. Such stored data can thereby provide at least some proof and/or evidence that the signer has read, watched, and/or listened to the agreement and has a higher likelihood of understanding what he or she has contractually agreed to. The signed contract and all of the additional data can be retrieved by any authorized party (e.g., agreement provider, agreement signer) at any time and downloaded from an electronic device. Similar to the methods used to store such additional data, the authorized party can retrieve such additional data, for example, by way of the Internet, recordable media, and/or wireless or wired connection.

Although specific example embodiments of the electronic consent and contract unit (386) were described, other embodiments of the electronic consent and contract unit (386) are possible. For example, the electronic consent and contract unit (386) can be a contract between a medical practitioner or a medical institution and a patient for any medical procedure, medical treatment, blood transfusion, laboratory test, surgery, or pharmaceutical treatment. A medical practitioner can include, but is not be limited to, physicians, surgeons, nurse practitioners, physician assistants, chiropractors, or acupuncturists. A medical institution can include, but is not be limited to, a hospital, surgery center, or academic medical center. The contract can further be between a clinical trial investigator and a research subject or between a financial institution and a customer, by way of example and not of limitation, for signing mortgage documents or credit card agreements. A financial institution can include, but is not be limited to, a bank, credit card company, mortgage lender, and credit union. The contract can also be between a business and a customer for signing waivers, between a governmental body and a citizen, such as when an individual is signing a will or trust, and between any two parties when signing any contract or agreement.

Example 2

Currently, clinical trials such as those performed for drug approval at the U.S. Department of Health and Human Services Food and Drug Administration (FDA) can be very specialized as well as difficult and expensive to run. The requirements for protecting human subjects rights and complying with regulatory concerns while validating accuracy and integrity of results (and the process of obtaining these results) obtained from these studies constitute a high burden on all parties involved (including but not limited to the FDA, the sponsor of the clinical trial, the contract research organization who manages the clinical trial, the physician investigator and his or her staff, and the patients and volunteers who participate in the clinical trial).

One embodiment of the present disclosure describes an exemplary integrated system for protocol design that specifically targets the designing, performing, and managing of clinical trials. The integrated system can be utilized to create an electronic protocol that encompasses clinical trial aspects from the beginning of trial planning to the submission of the data and final analysis reports and from the top view of data summary to the detail view of each subject's specific intake of test material, including monitoring and verification, throughout a single clinical trial study and across multiple clinical studies. The electronic protocol can then be used to drive a clinical trial through its entire lifetime.

The integrated system for protocol design described in the present disclosure can be applicable to other programs with strict protocol requirements besides clinical trials. For example, disease management and wellness management generally require protocols, pathways, and guidelines to guide their implementation, high accuracy and integrity of results as well as protection of a subject's privacy and other rights. Many other industries besides the medical field also have programs that may be applicable to the integrated system for protocol design described in the present disclosure. For example, drug manufacturing and high tech manufacturing require high accuracy and integrity of results as well as protection of records and compliance to regulatory rules.

Figure 4B:
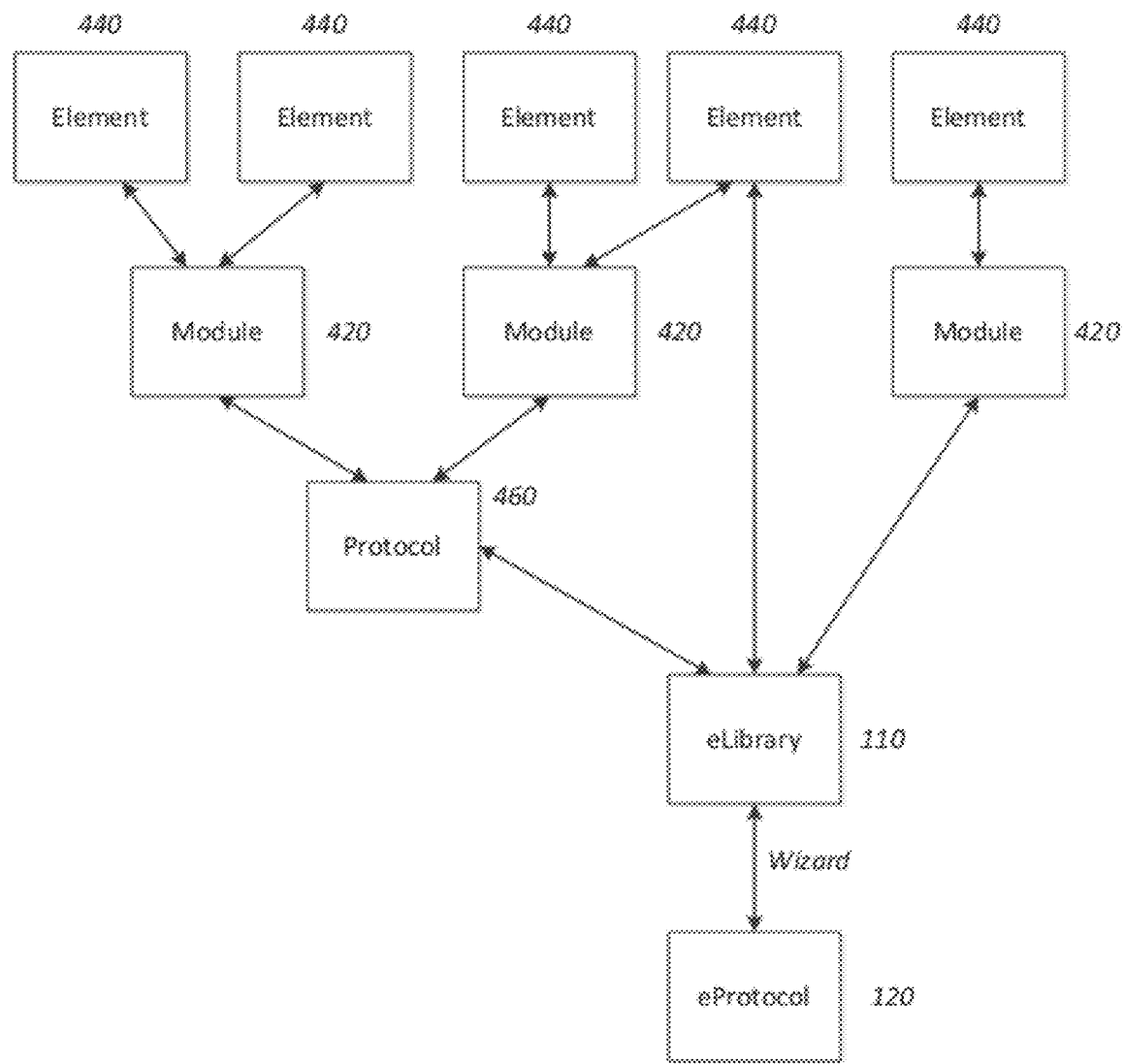

With reference to FIG. 4B, creating a protocol for a clinical study may comprise selecting relevant protocol modules (420), protocol elements (440) and protocols (460) from an electronic library (110). The protocols (460) from the electronic library (110) may be complete or incomplete protocols and may be from past studies or current studies within the system or from a third-party. The creating of a protocol my comprise selecting a protocol from the electronic library (110).

The creating of a protocol may also comprise selecting the relevant protocol elements (440) for each protocol module (420) and combining the protocol modules (420), protocol elements (440) and protocol (460) to design the experimental plan via a electronic protocol unit (120). The electronic protocol unit, or eProtocol (120), may comprise software, firmware, middleware and hardware system involved in creating a protocol for executing any programs and instructions involved in the performance of the clinical trial study, as well as information such as number of sites, subjects per site, duration of study, subject clinic visit schedule, subject exclusions, data to be collected, and others as shown in FIG. 4F.

Each protocol element (440) of FIG. 4B represents a specific procedure, method, or question that has been shown to be effective in collecting a key piece of information for the clinical study. Protocol elements (440) are selected and assembled to form a protocol module (420), which is a group or a classification of activities required for the clinical study. A protocol is designed by selecting and assembling a plurality of relevant modules. The assembly process may involve a resolution of conflicts between the elements to form modules and between the modules to form the electronic protocol unit (120).

Figure 4C:
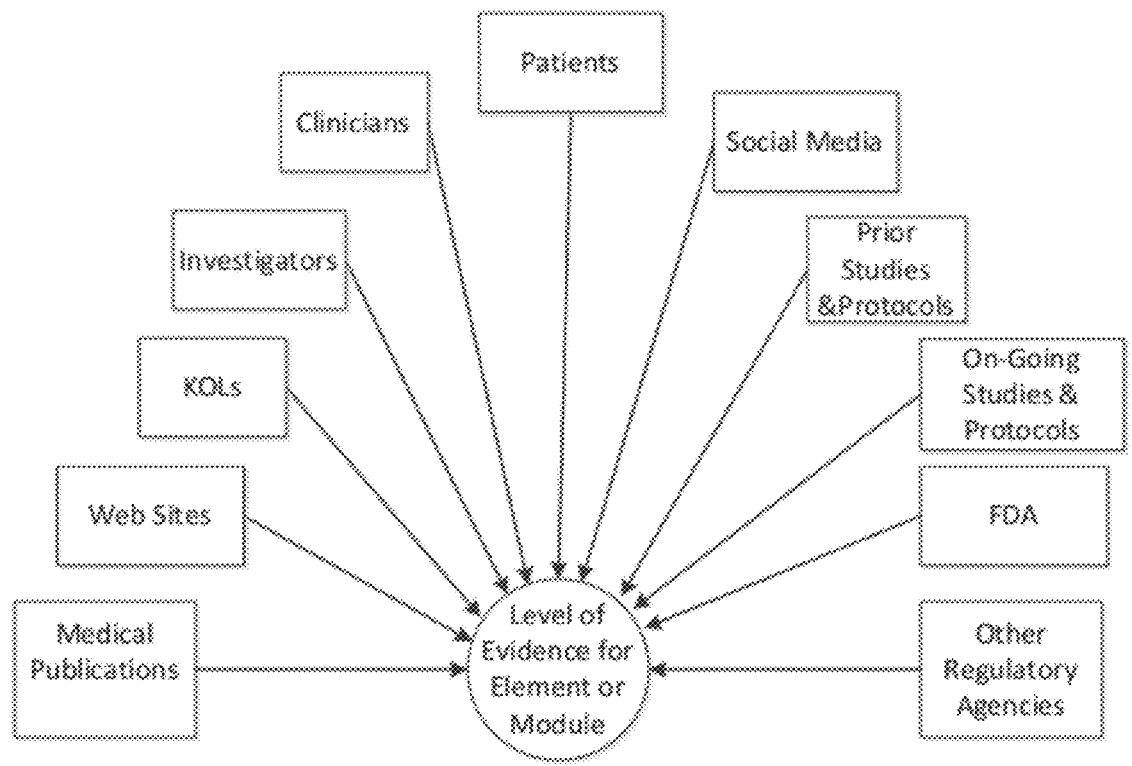
Figure 4D:
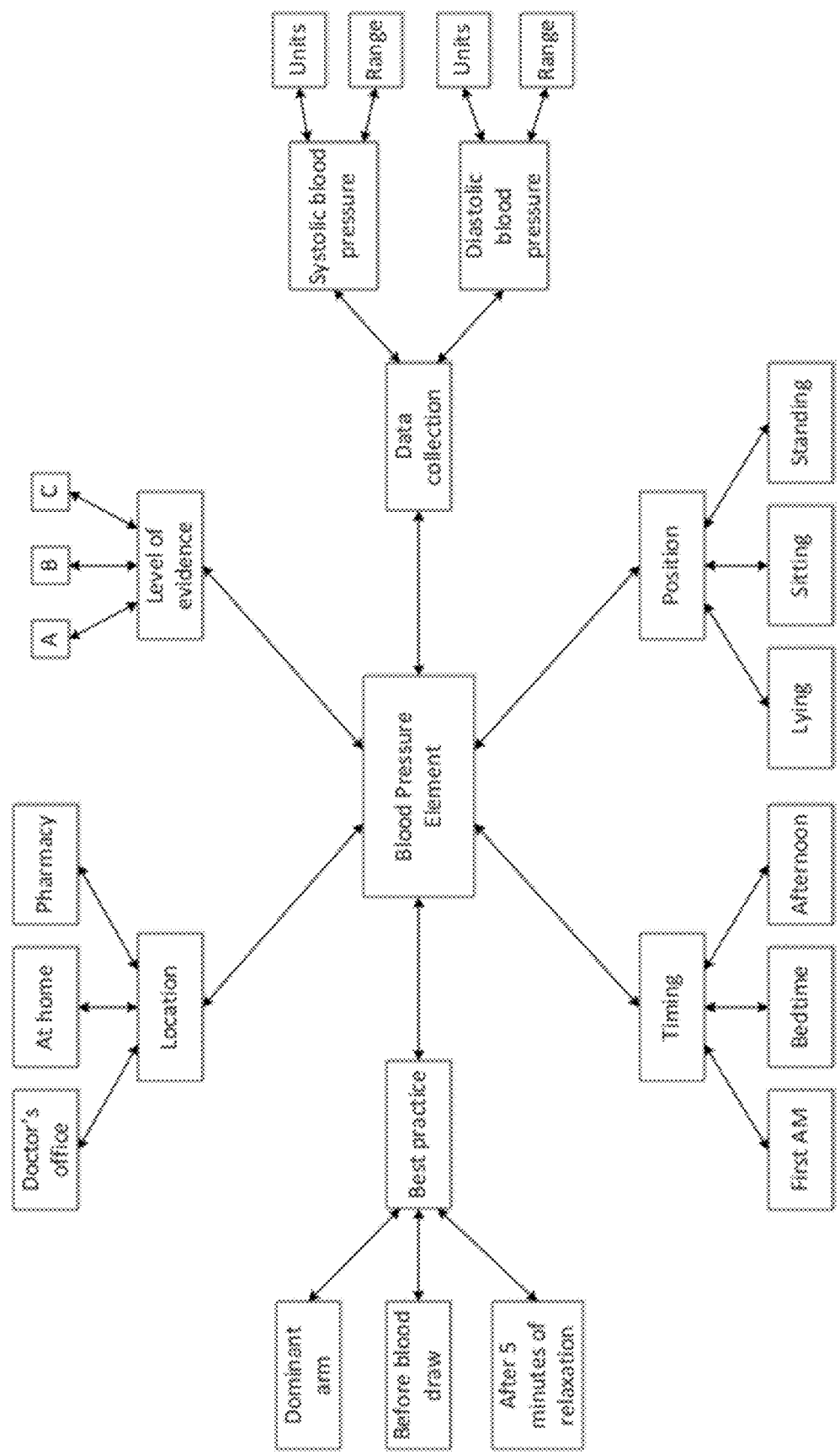
Figure 4E:
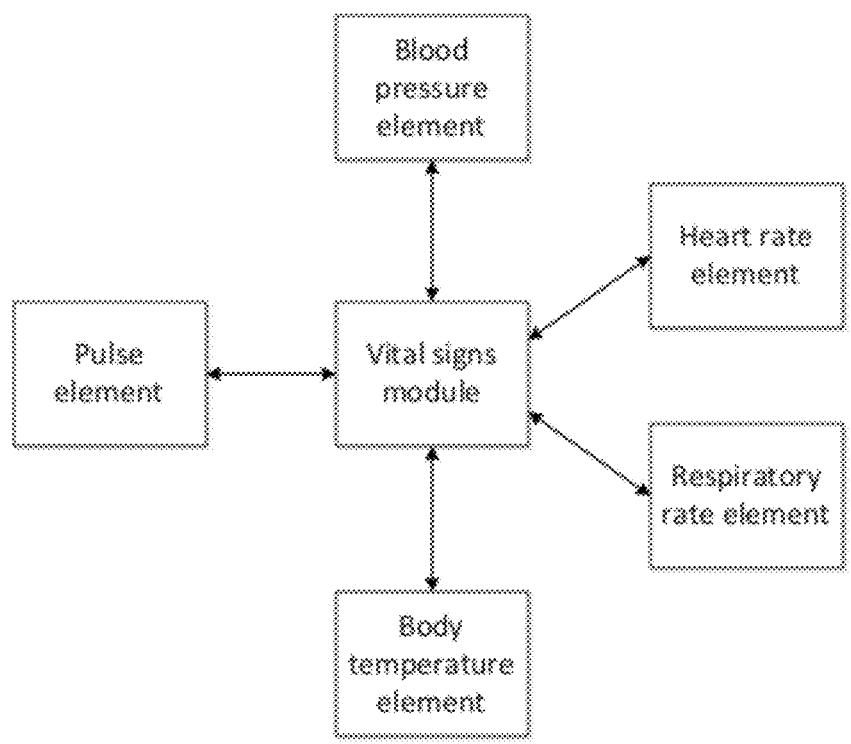
Figure 4F:
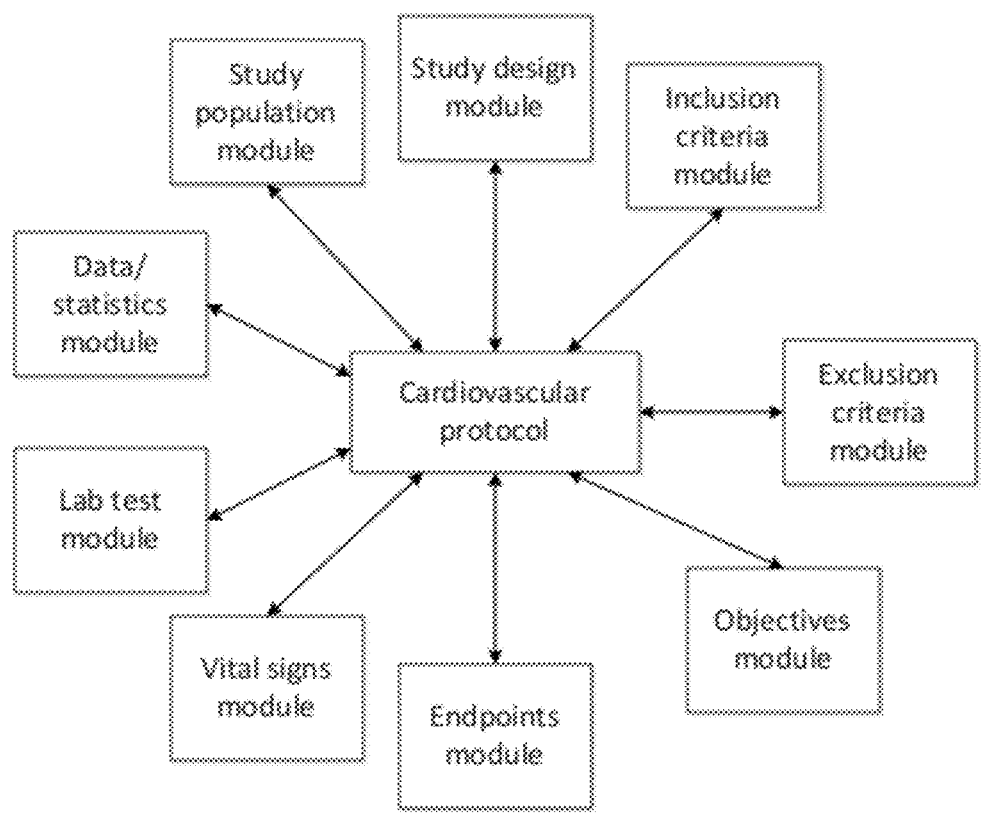

For example, in the design of the electronic protocol unit for cardiovascular studies as shown in FIG. 4F, a measurement of vital signs can be required at every clinical visit by the subjects as indicated in a vital signs module. Other modules required by the cardiovascular protocol may include the lab test module, the data/statistics module, the study population module, the study design module, the inclusion criteria module, the exclusion criteria module, the endpoints module, and the objectives module.

The vital signs module selected may be as shown in more detail in FIG. 4E. The vital signs module may comprise various elements such as a blood pressure element, heart rate element, body temperature element, pulse element, and respiratory rate element as shown in FIG. 4E. Within each element, various additional information regarding the execution of the elements can be present. For example, as shown in FIG. 4D, the blood pressure element may contain information regarding the location, best practice, timing, position, data collection units and ranges, and the level of evidence for the suggested information in the element.

Also, if an investigator is unsure if, for example, the recommended respiratory rate measurement method in the element is applicable to the clinical study, the investigator may elect to review the level of evidence as shown in FIG. 4C for a recommendation and compare the context of source of the recommendation or input, which may be the journal article or past study documents. The investigator may select an alternate respiratory rate element based on the review of the level of evidence.

Also, if an investigator is unsure if, for example, the recommended respiratory rate measurement method in the element is applicable to the clinical study, the investigator may elect to review the level of evidence as shown in FIG. 4C for a recommendation and compare the context of source of the recommendation or input, which may be the journal article or past study documents. The investigator may select an alternate respiratory rate element based on the review of the level of evidence.

Similarly, for the design of a diabetes study, selection of the vital signs module containing the blood pressure element, heart rate element, body temperature element, and respiratory rate element can be linked to a specific journal article showing these vital signs to be representative of the general impact of the disease on overall health level of the subject.

Selection of relevant protocol, modules and elements can be accomplished according to different methods. For example, a hierarchical library can be presented with the categories of protocols, modules, and elements offered. A search function can also be included. Choices of protocols, modules, and elements can be offered or removed based on protocols, modules, and elements already selected for the clinical study.

A wizard that presents questions to be answered may be offered to guide the selection of protocols, modules, and elements. The guidance from the wizard can be adjusted based on additional criteria input from the user such as cost, options, and time. For example, to see a wider selection of modules, the module selection can be offered in an order from the least restricting choices to the most restricting choices.

In addition, the system may highlight conflicts created by the combination of the selected protocol, modules, and elements and prompt a resolution of the conflicts. The wizard may suggest additional modules or elements based on the protocol, modules or elements already selected.

The question and answer interaction with the wizard may be delivered on an electronic device (e.g., computer, portable computer, tablet computer, smart phone, game console, e-book reader, holographic device, television screen, video screen) sent by mail or email or asked over the phone by a system that converts the questions to speech and then records and interprets the answers (converts speech to text).

The wizard may have capabilities to accept inputs from multiple users and/or multiple sessions. For example, a team of doctors and a sponsor's team members may form a protocol design team such that each member of the team may give input as to some or all aspects of the clinical study. One doctor may be an expert in the target disease treatment, and thus can be of good authority to give guidance regarding primary and secondary symptoms to monitor. A member of the drug company sponsor may be a specialist in the dosing. Another member of the team may be a clinical trial specialist who may give input regarding subject selection criteria. Yet another member of the team may be a statistician who may give input on the number of subjects needed in the clinical trial.

The integrated system for protocol design may have a team management feature to manage and authenticate the inputs from various members of the team. An authentication feature may verify the identity of each member of the protocol design team when giving input and may record the date, time, and actual input for audit purposes. A team management feature may identify conflicting inputs from different members and present these conflicts to the members who introduced them for resolution. Alternatively or in addition, the conflicts may be presented to the team leader for resolution. The team management feature may identify missing input. The team management feature may also tag required input from specific members. For example, the sponsor may be tagged with the input for dosing of a drug.

The wizard may be capable of accepting input from an existing complete or incomplete protocol (paper or electronic) into a newly designed electronic protocol. For example, if a follow-on study is desired to match in number of subjects and frequency of dosing as a previous study, the wizard may accept the existing protocol, and, by matching aspects of the existing protocol to protocol elements (440) and protocol modules (420) in the electronic library (110) as shown in FIG. 4B, the wizard can guide the user into creating the new electronic protocol that may match the previous study in specified areas. Additionally, if a protocol has already been developed by the sponsor of the clinical trial, the wizard can identify the requirements of the existing protocol and match them to the best-match modules and/or elements within the eLibrary (110). The wizard can then suggest additional modules or elements as necessary for the performance and analysis of the clinical trial.

In one embodiment, the electronic protocol designed by the integrated system may now contain specifications regarding a plurality of additional aspects of the clinical trial including but not limited to the aforementioned elements and modules.

The details, instructions, guidance, requirements, outcomes, and recommendations for performing all of these areas of the clinical trial in accordance with the requirements set forth in the electronic protocol guide the execution and management of the clinical trial by the creation of documentation, in electronic or paper format, utilized in various stages of execution of the clinical trial. As shown in FIG. 4A, such documentation may contain sets of structured information configured for use by one or more units such as eSource, eCRF, eConsent, eCompliance, ePRO, eInventory, eStudy Product, eSponsor, eMonitor, eRegulatory, eFinance, eRecruitment, eData, eStatistics, eInvestigator, eLaboratory, eProcedure, ePatient, eDocument, eSafety, and eCTMS.

Figure 4G:
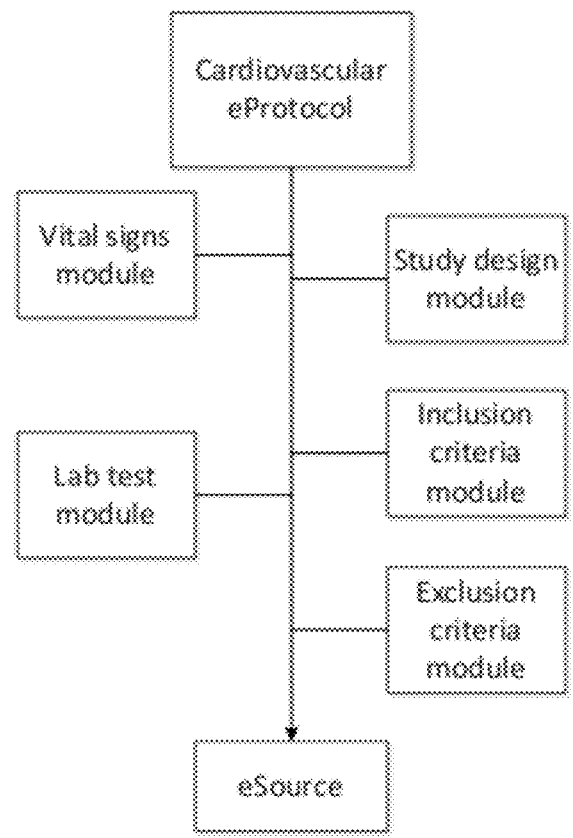

For example, the eSource can be an electronic data collection system that can be created by the electronic protocol to be used in a clinical trial visit to guide the collection of data. FIG. 4G shows as an example a cardiovascular eProtocol, where information from the vital signs module, the study design module, the inclusion criteria module, the exclusion criteria module, and the lab test module may be used to create an eSource data collection system.

As another example, the eConsent can be a consent form for the clinical trial, which can be presented, possibly in electronic format, to the subject during the first clinical trial visit for signature, then stored again, possibly in electronic format as well.

Example 3

FIG. 4B shows a diagram of an exemplary structure of an electronic library (110), or eLibrary, from which the integrated system for protocol design can be used to create a protocol. The electronic library (110) comprises protocols (460), which are based on protocol modules (420) of experimental design. The protocol modules (420) are, in turn, based on protocol elements (440) of previous protocols and clinical trials that have been executed successfully, based on published data from other previous clinical studies, or based on data from therapeutic experts. The protocol module (420) may contain best practice methods relating to a particular topic, such as diabetic studies; an experiment specification, such as the requirement to include pediatric subjects; or a data specification, such as the requirements for performing daily blood pressure measurements.

Each protocol element (440) of the electronic library (110) is based on a level of evidence that includes inputs from a large variety of sources. The weight and conflict resolution of the data from each of the input sources is constantly evolving and learning from outcomes of each use of the integrated system for protocol design.

Examples of input sources to the level of evidence for the elements (440), modules (420), and protocols (460) include but are not limited to medical publications, regulatory agency rules and advisories, past studies, past protocols, database websites for past studies, key opinion leaders (KOLs), investigators, doctors, patients, social media, and ongoing study feedback as shown in FIG. 4C. The level of evidence for each protocol element (440), such as an original document for the source or a summary of multiple documents with appropriate citations, can be readily accessible to aid in the selection of protocol elements (440) for the design of the electronic protocol.

In an embodiment of the present disclosure, the electronic library (eLibrary) (110) as shown in FIG. 1 is described, where the electronic library (110) comprises protocol modules stored in a database (130) of FIG. 1. These protocol modules may contain best-practice methods for the design, performance, or analysis of a clinical trial, including but not limited to modules of experimental designs, layout, questions, procedures, visit and/or procedure timing, resources required, the order in which steps are to be performed, subject inclusion and exclusion criteria, regulatory requirements, data requirements, and statistical analyses. Each protocol module may be based on one or more previous electronic protocol units (120) of FIG. 1, which have been executed successfully or based on data from one or more previous clinical studies or a combination thereof. The protocol modules can be accessed, for example, to be used to create or change an electronic protocol unit (120) during the design, performance, or evaluation of a clinical trial study.

The protocol modules (420 in FIG. 4B), protocol elements (440) and protocols (460) in the eLibrary (110) may originate within the system, from the user, or from a third party. Third-party modules may be provided by a third party, who may be a specialist in the field. Protocol modules may be accessible and/or purchased through an on-line store. The on-line store may have cataloging and searching functions so that the expertise of a specialist may be accessible to many users who would like to design a clinical study. The on-line store may also manage payment of compensation from the user to the system or from the user to a provider of the third party module through the system.

According to an embodiment, each module may be vertically integrated, in that it may contain proposed procedures for a study from the beginning of design to final report submission and may include procedures for source creation, data collection, statistical analysis, recruitment (e.g., provide criteria), compliance verification, consent verification, confirmation of attendance, verification, interim and final reporting format and frequency to various parties, and even billing milestones. For all of the procedure steps, editable and suggested electronic formats may be provided. In one, interactive applications, programs, and instructions may be provided for the procedures.

Example 4

In an embodiment of the present disclosure, an electronic sponsor unit is described. The electronic sponsor unit may be utilized by a sponsor of the clinical trial study to view interim reports of the study. The electronic sponsor unit may also be used to track progress and milestones, view visitation information of subjects to the study sites, review data monitoring results, review raw and calculated data for the study, and review or revise the electronic protocol. The electronic sponsor unit may comprise specified security features that block identifying information from access by the sponsor.

Example 5

Embodiments of the present disclosure relate to systems and methods for enhancing collection of data from medical or clinical research visits. During a clinical visit, such as in the context of a clinical trial, paper is still used as the primary means for the initial capture of data. This initial capture of data is also known as source data and the document on which this original data is captured is referred to as a source document. The method of data collection by paper is highly variable and generally involves transcription from paper into an electronic database in order to be used for data analysis. This method of data collection can lead to human errors, missing data, and invalid data as well as fraud since data may be intentionally falsified or modified to meet certain requirements of the study. Monitoring of medical or clinical data can be an expensive and time-consuming process and primarily involves checking the data in the paper records compared to the transcribed data.

The medical or clinical data can be data related to healthcare in general and, for example, clinical trials in particular. In addition, these considerations apply to many clinical interactions including but not limited to disease management and wellness management, many of which may rely upon a protocol, guideline, or pathway to determine the required steps, and which may benefit from the electronic medical source methods and systems of the present disclosure.

By way of example and not of limitation, one embodiment of the present disclosure shows a use of the electronic medical source methods and systems in a clinical trial setting. Other exemplary uses can include, but are not limited to, management of ambulatory care facilities such as medical offices, clinics and others, ambulatory surgery facilities, hemodialysis facilities, rehabilitation facilities, drug abuse treatment facilities, family planning centers, hospitals, home health agencies, hospices, clinical trials clinics, oncology clinics, pharmacies, adult day healthcare centers, assisted living facilities, nursing homes, residential health care facilities, disease management programs, and wellness management programs.

One skilled in the art will recognize that the subject of the clinical visit can be a patient and will also recognize that collection of data can be related to performance of a clinical trial study protocol (e.g., required activities in the protocol) within a specific timeframe. These study related activities include, but are not limited to, answering medical questions; performing a physical examination; dispensing and/or taking an investigational study product; filling out a diary, scale, or questionnaire; eating a specific study related food or beverage; measuring a body function such as temperature or blood pressure; measuring an anthropomorphic measurement such as weight; performing a test such as an EKG or stress test; and collecting a specimen such as urine, saliva, stool, semen, or blood.

Benefits associated with the methods and systems of the present disclosure can be an increase in reliability and validity of the data collected during a clinical trial and a reduction in the time associated with the data acquisition and in the time required to verify the validity of the data. This can improve clinical study statistics and may decrease cost by decreasing the number of required subjects for a study and/or the time required to complete the study.

The embodiments of the present disclosure describe the electronic medical source methods and systems that may be utilized to capture clinical data in a structured manner. The electronic medical source may be used to allow a first capture of data to be the only time that data is captured (e.g., no additional transcription or data entry is performed). The entire data capture process can be recorded on video and instantly quality checked for consistency and validity. Potentially invalid or inconsistent data can be identified and presented to the clinical staff for correction.

For clarity purposes, the terms "eSource" and "eSource unit" are used interchangeably with "electronic medical source" and describe the electronic medical source methods and systems of the present disclosure. By way of example, the eSource unit may be implemented in software executed locally with a hardware device such as the IPAD® tablet computer (personal computer). The hardware device may, for example, be the exemplary hardware system (200) as described in FIG. 2. The hardware device may comprise hardware for wireless communication, video capture, writing capture (such as a touch screen), memory for execution of applications, memory for storage of applications and data, display (such as a screen or a hologram), and input (such as a keypad or keyboard). The device may comprise hardware that performs more than one function, such as a touch screen, which can perform both display and input functions. The eSource unit can also be a software application running on a remote system that can be accessed by way of the Internet (or other network connection) using a hardware device, such as the exemplary hardware system (200) as described in FIG. 2.

The eSource unit may comprise additional health monitoring equipment such as a scale or a blood pressure measurement device, each with its own processor, memory and communication hardware, and each capable of communicating with the eSource unit.

Figure 5A:
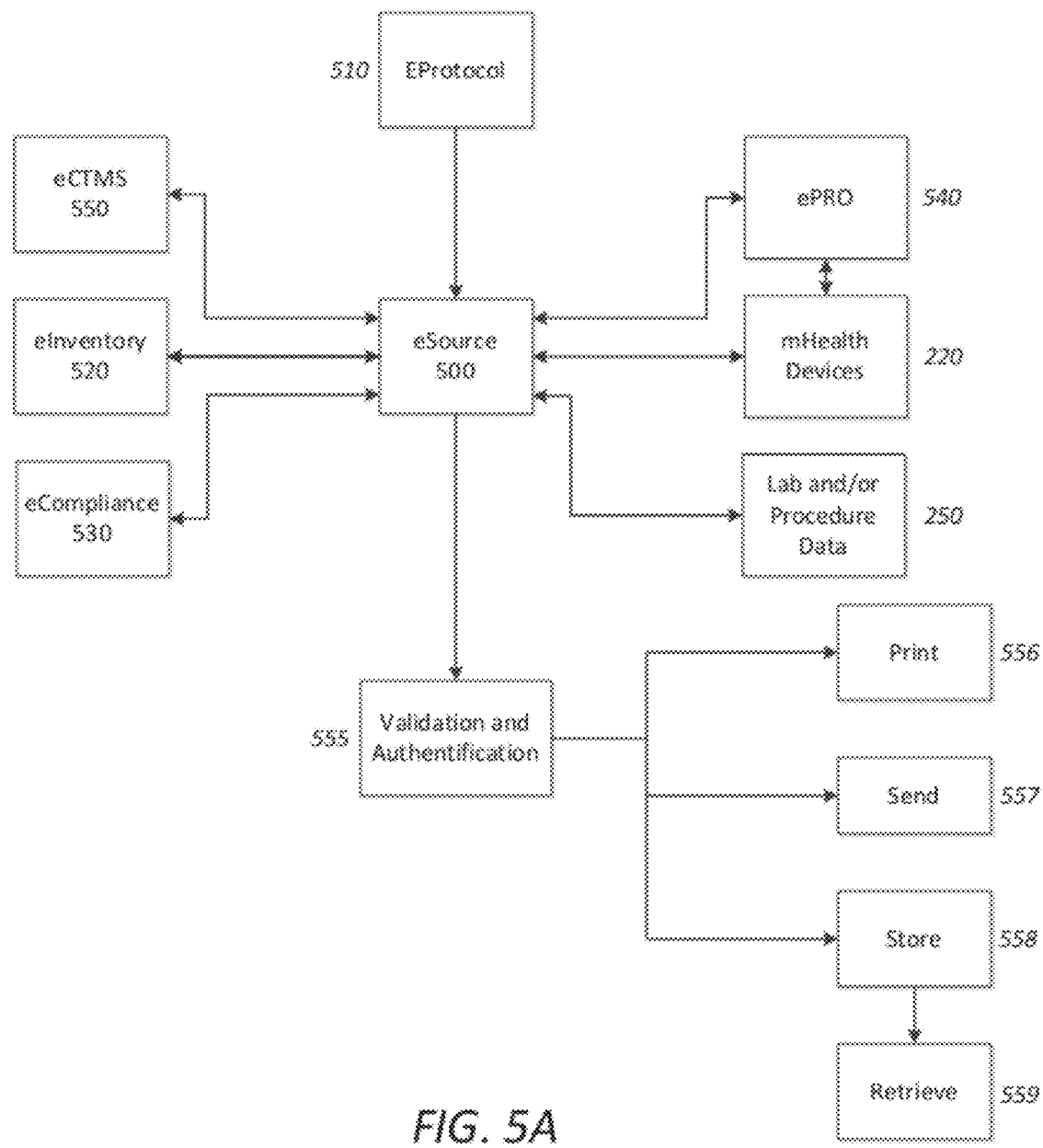
FIGS. 5A-5G show flow charts and displays of an exemplary electronic source unit of the present disclosure.
Figure 5B:
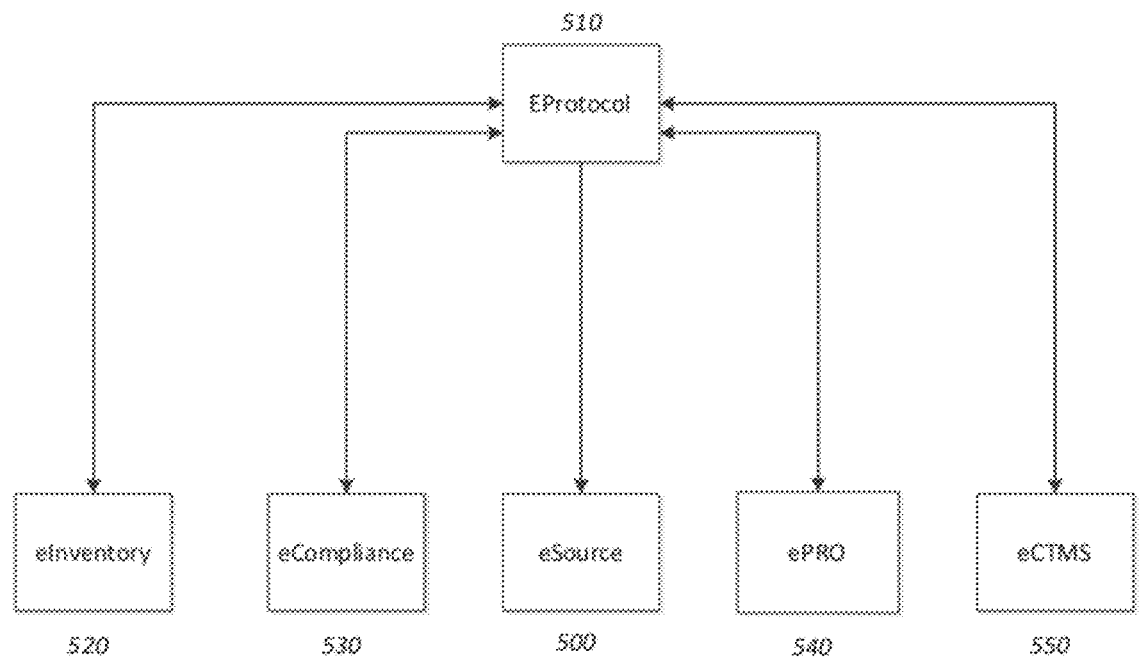

FIG. 5A shows an eSource unit (500) that comprises contents based on requirements of an eProtocol unit (510). The eSource unit (500) may connect with an eInventory unit (520), eCompliance unit (530), ePRO unit (540), and eCTMS unit (550). Each of these units (eInventory (520), eCompliance (530), ePRO (540), and eCTMS (550)) has a direct connection to the eProtocol unit (510) (see FIG. 5B), since the elements and modules of the eProtocol unit (510) may direct the requirements for each of these systems.

The eSource unit (500) can be provided to a clinical research staff for conducting a clinical study in a medical clinic. According to an embodiment of the present disclosure, the eSource unit (500) can be configured to collect data directly (via wired or wireless connection) from a variety of medical devices (220 in FIG. 2) (collectively known as mobile health or mHealth devices).

The results of the measurements of the mHealth devices (220 in FIG. 2) can be imported directly into the eSource unit (500 in FIG. 5A) and can be displayed on the electronic device for review by the research staff. Data values from these mHealth devices (220 in FIG. 2) that are out of the expected range can trigger alerts and prompts for the research staff including prompts for retesting, additional tests, or additional questions.

Alternatively or in addition to receiving data from mHealth devices (220 in FIG. 2), the eSource unit (500 in FIG. 5A) may be configured to collect data and/or reports directly from laboratory and medical procedural sources (250 in FIG. 2), where the sources (250 in FIG. 2) may be external analytical laboratories, medical specialties, or in-house lab instruments as previously discussed in to FIG. 2. For example, a device may transmit the glucose level in a urine sample or a scale may transmit the remaining test material brought back by a subject to the eSource unit (500 in FIG. 5A).

Figure 5C:
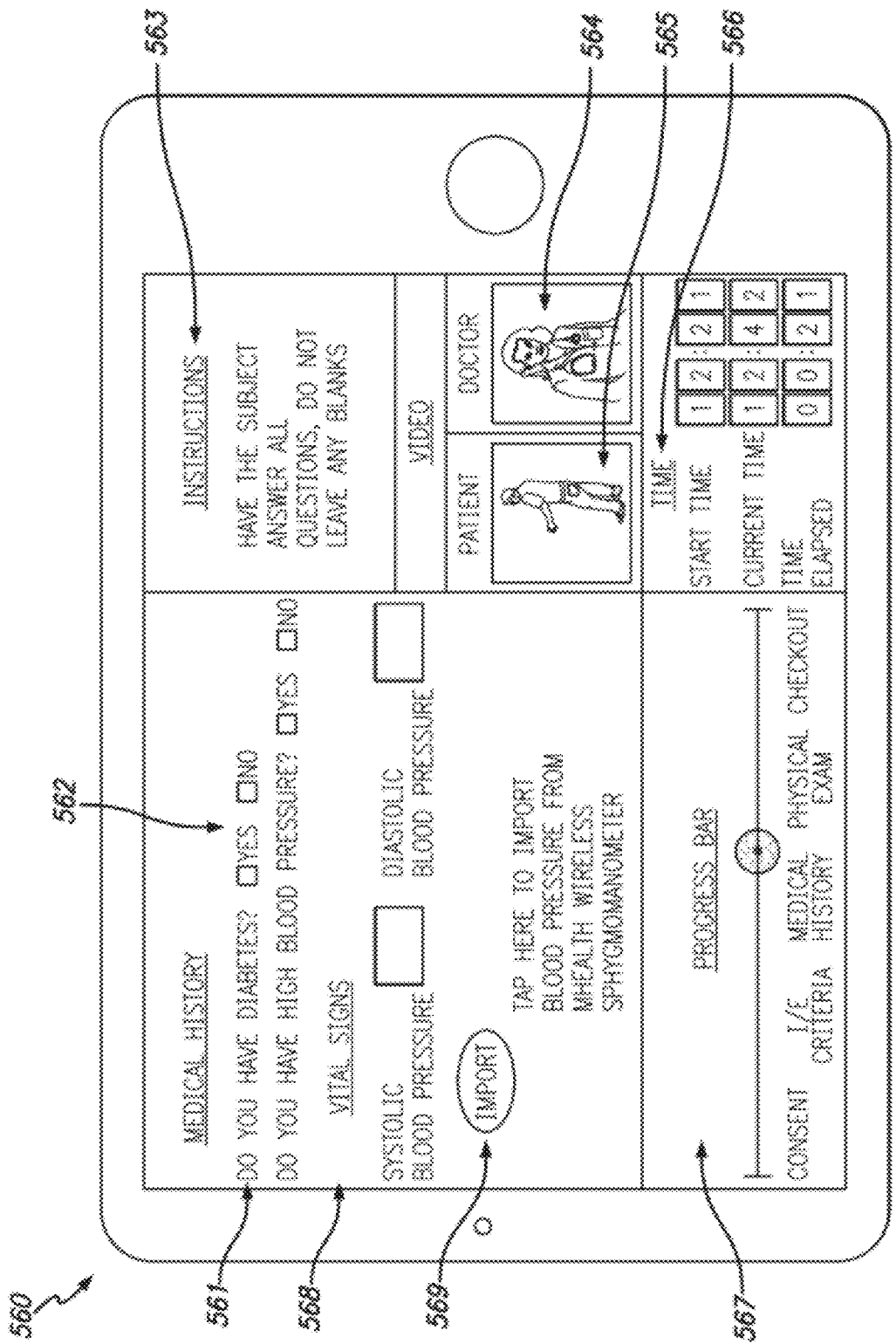

FIG. 5C shows an exemplary display (560) of a screen of the eSource unit (500) from FIG. 5A. The display (560) can be configured to provide a doctor with step by step instructions as to how to proceed with the clinical research study visit in order to comply with a research protocol. Compliance with a protocol includes, but is not limited to, compliance with the required steps of the protocol, following the correct sequence or timing of procedures, collecting data in the correct manner, compliance with Good Clinical Practice (GCP), compliance with Standard Operating Procedures (SOPs), and compliance with best practice methods for performing the required procedures. In an embodiment of the present disclosure, the display (560) can be configured to allow one or more sub-screens to be viewed simultaneously, with each sub-screen showing different information. Type and location of each sub-screen can be user configurable for optimal ease-of-use.

The display (560) can be configured for use by a clinician or doctor to have a plurality of sub-screens for simultaneous display of a plurality of clinical information. For example, the display (560) can have sub-screen showing the clinician or doctor the next step to be performed, which can be a required question (561) or a procedure according to a particular clinical study protocol. The sub-screens on display (560) can be configured to display separately or simultaneously the question to be asked (561), a range of acceptable answers to the question (562), and a set of guidelines or instructions pertaining to how to ask the question (563).

The display (560) may also include sub-screens comprising a video of the doctor asking the question (564); a video of the research subject answering the question (565); an elapsed time display (566) showing the start time of the patient visit, the current time, the elapsed time; and a progress bar (567) for the entire clinical visit showing how many steps have been completed and how many steps are remaining.

Additionally, the display (560) can include sub-screens configured to display the next required procedure (568). The display (560) can also comprise a data import button (569) with which the user may initiate the importation of the data directly from a mHealth device (220 in FIG. 2), such as that shown in FIG. 5A. The importation of data from the mHealth device (220 in FIG. 2) maybe via a wired or wireless method, and can be directly or through an Internet protocol or other methods as described in the Hardware and Software section.

Figure 5D:
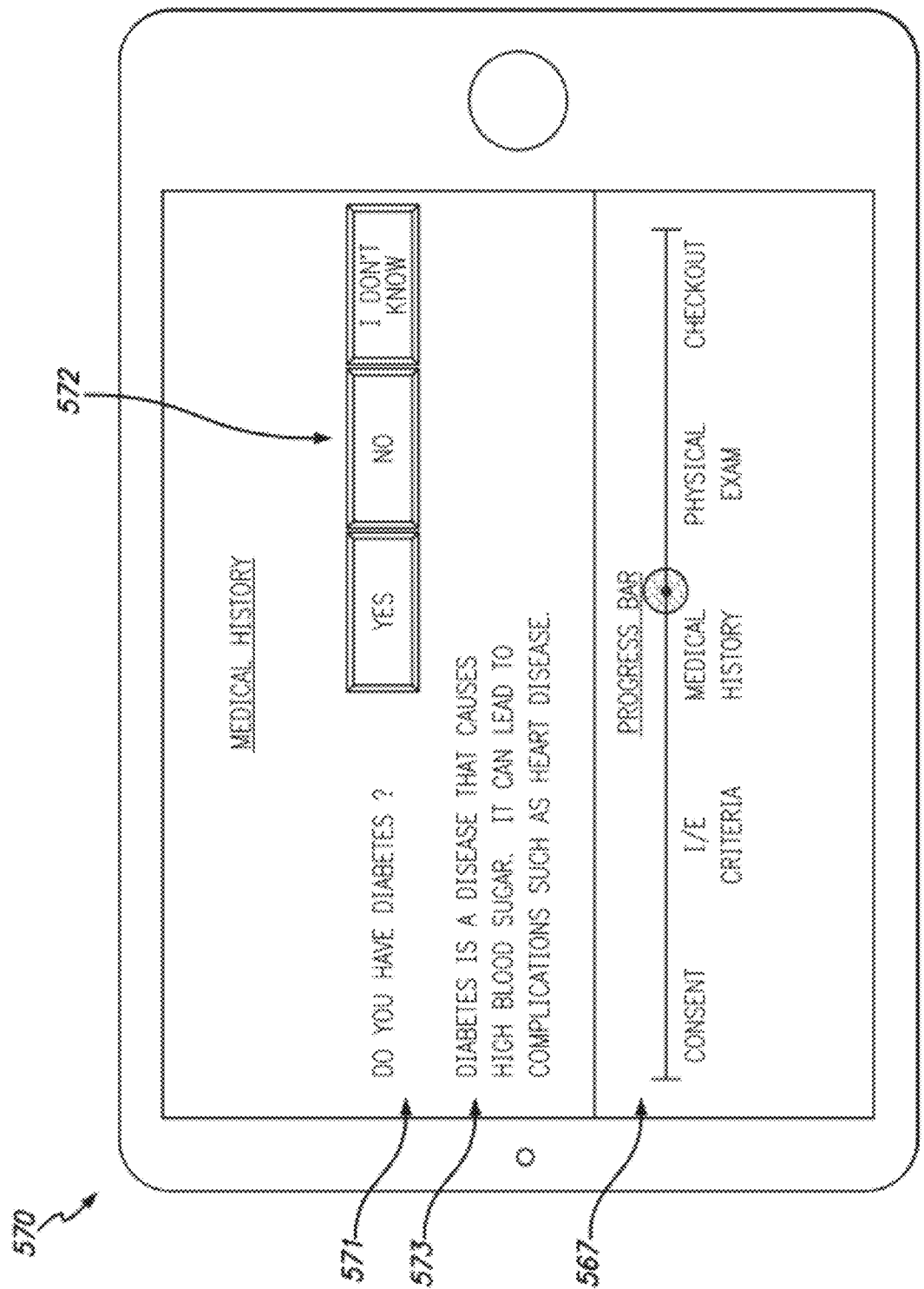

In another embodiment, the patient or subject may be provided with his or her own electronic device. FIG. 5D shows an exemplary display (570) of the screen of the patient's eSource unit (500) from FIG. 5A. The exemplary display (570) can be configured to provide a patient with step by step instructions as to how to proceed with the clinical research. The exemplary display (570) may provide information to help the patient comply with requirements of a particular research protocol and to enable the patient to have more control and information about the clinical visit. Study results have shown that educating the patient about their care leads to higher levels of compliance and success with medical treatments [see reference (4)].

The exemplary display (570) shown in FIG. 5D can show to the patient information about the next required question to be answered (571), the range of acceptable answers to the question (572), patient-friendly detailed background information (in either text, audio, video, or game format) about any medical terminology or jargon in the question (573), and a progress bar (567) showing how many steps of the visit have been completed and how many steps are remaining. The progress bar (567) can be helpful in providing a map of the visit to the patient so that he or she can review the procedures completed and those procedures coming up and ask questions accordingly.

It is noted that the required question to be answered (571) and the range of acceptable answers to the question (572) shown in FIG. 5D may be worded differently from the same question (561) and range of accepted answers (572) shown in the screen of the doctor's device as shown in FIG. 5C. The patient's version shown in FIG. 5D may be worded differently, such as with paraphrasing for medical jargons, to provide clarity to the patient.

Figure 5E:
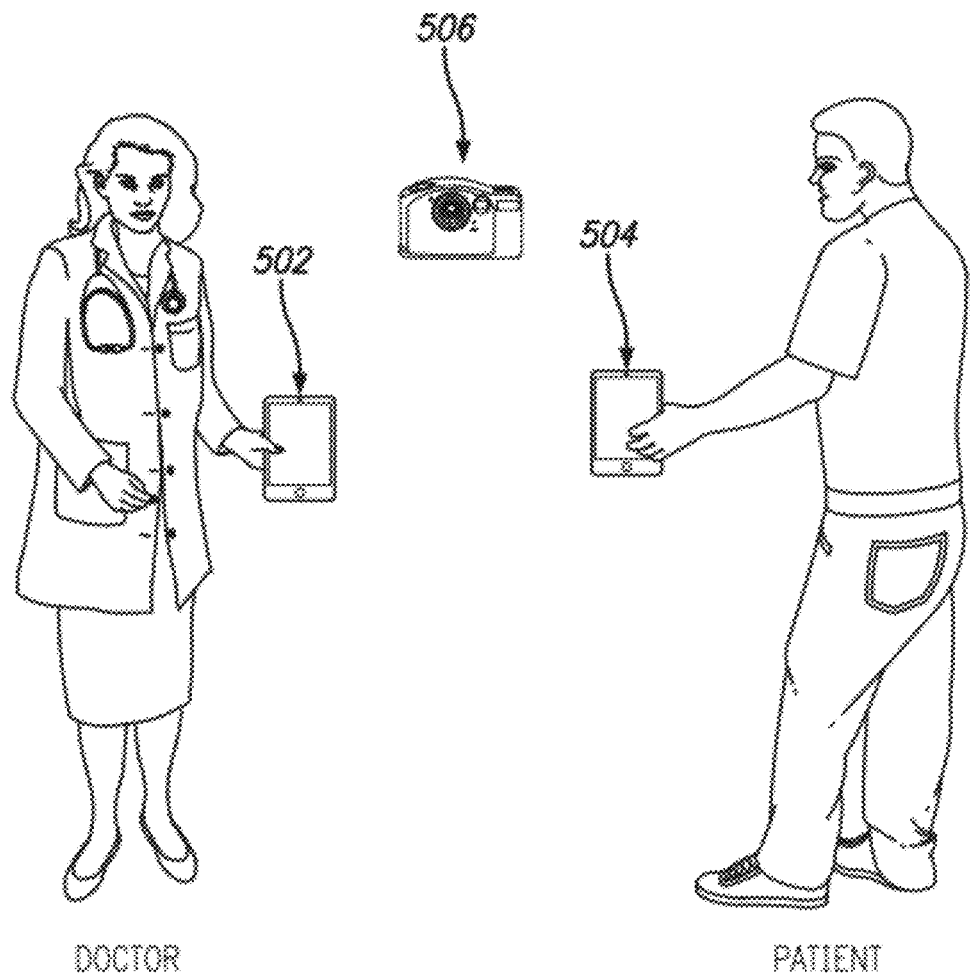
Figure 5F:
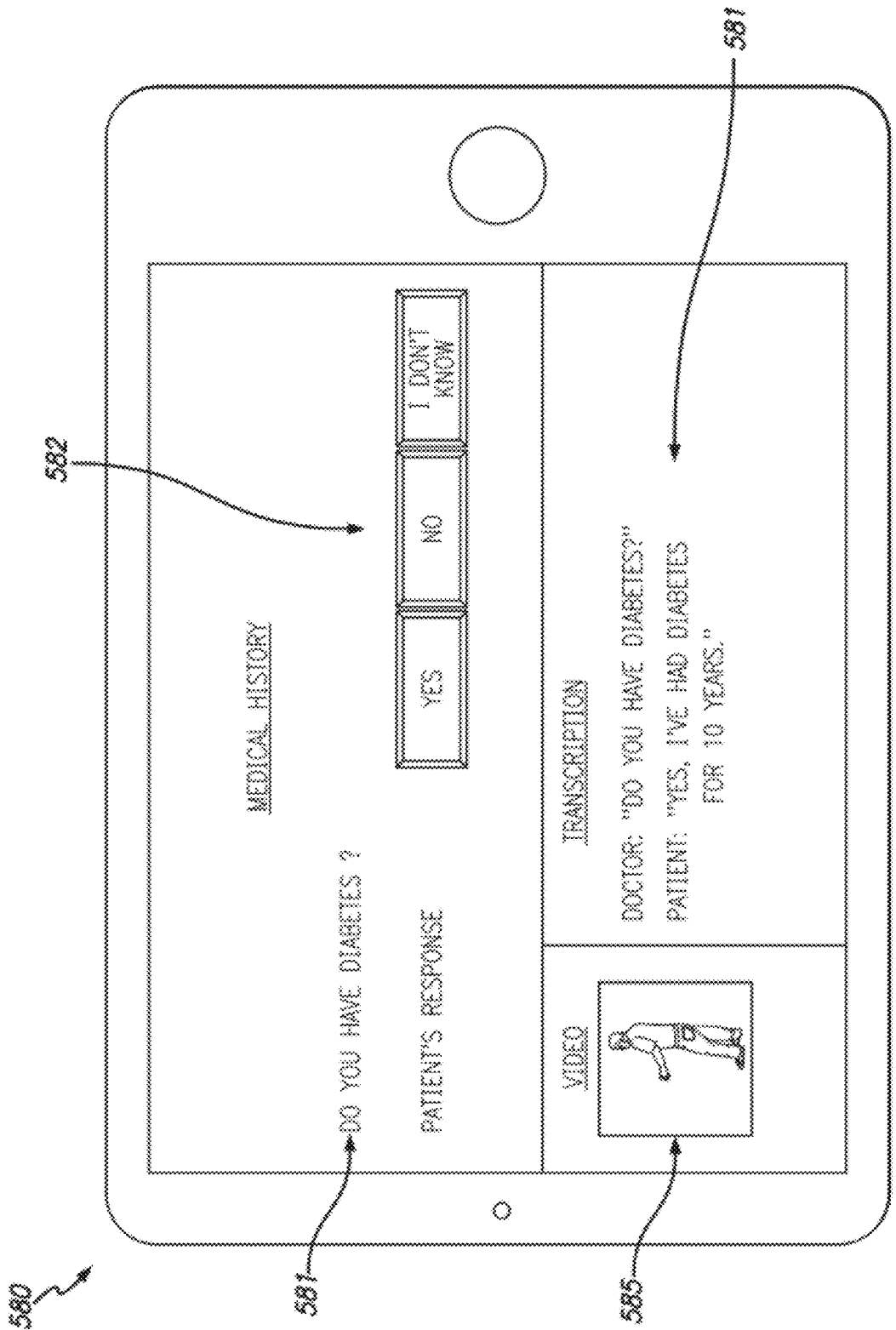

FIG. 5F shows another exemplary display (580) of the screen of the eSource unit (500) from FIG. 5A demonstrating another embodiment of the present disclosure. The exemplary display (580) can be configured to provide a doctor with the next required question (581) or procedure according to the clinical study protocol. The display (580) can be configured to display separately or simultaneously the question to be asked (581), the range of acceptable answers to the question (582), a video of the research subject answering the question (585), and a running transcription of the doctor's questions and the patient's answers (587).

The display of the required question(s) may be conducted in a manner similar to a teleprompter that guides the doctor as to what to say or do next. The video recording of the research subject (585) can be processed on the electronic device or on a remote device or server in real time or at a later time by using identity recognition algorithms (including but not limited to voice and facial recognition). The running transcription of the doctor's questions and the patient's answers (587) may be produced by a voice-to-text dictation application that can be a part of the eSource unit (500) or can be processed remotely on a separate device or server.

Figure 5G:
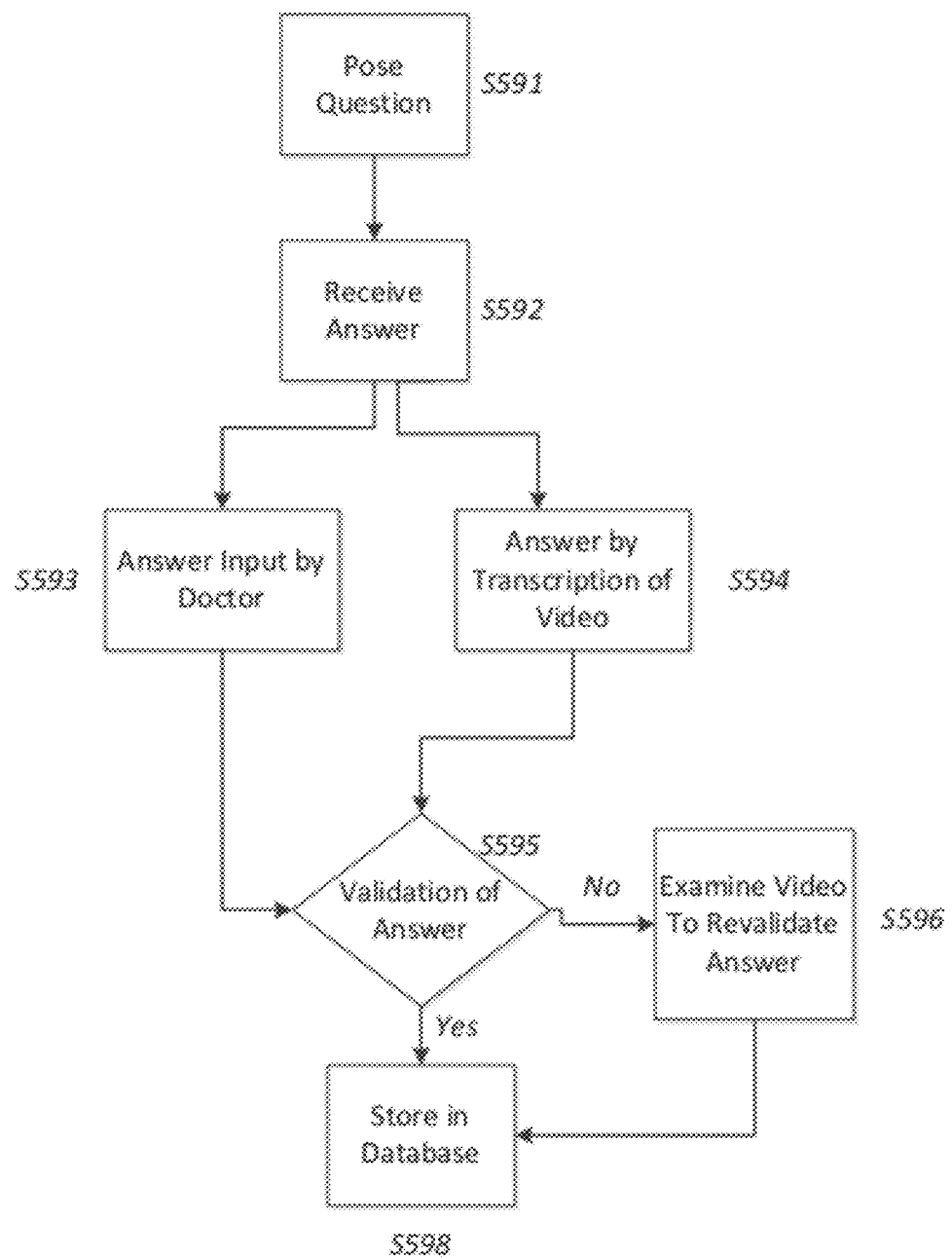

FIG. 5G shows a flow chart of a method of validation that may be applied to any question and answer exchange step between a clinician and a patient. A question may be asked by the doctor in a step (S591) and answered by the patient in a step (S592). The eSource unit (500) may provide the transcription of the answer in a step (S594) from the audio portion of the video recording.

The transcription can be compared in a step (S595) (in real time or at a later date/time) to the answer input by the doctor or the patient in a step (S593) during the clinical visit. The two answers to the question (the answer input into the device and the answer verbally spoken and then transcribed from speech to text) will be validated by the comparison in the step (S595). If there is a discrepancy between the two answers (input from step S593 and transcription from step S594), then the original video recording of the answer in step (S592) can be replayed and possibly retranscribed in a step (S596) to validate and confirm the correct response. Once the answer has been validated, it will be sent to the database in a step (S598).

In another embodiment, the doctor or research staff can utilize the electronic device by voice by repeating the answers that the subject provides into the microphone. The doctor or research staffs voice can be transcribed and complete the answers to the questions on the eSource unit (500) shown in FIG. 5A. In this embodiment, the eSource unit (500) provides an electronic scribe-like function similar to human scribe use in some medical offices. A doctor can narrate his exchange with a patient and the eSource unit (500) can transcribe the answers to the questions and answers as well as any additional unstructured comments that can be converted from speech to text.

Since the video and transcription may be running simultaneously with the list of questions to ask and the step by step instructions, the eSource unit (500) may automatically complete the data entry with the answers given by the clinician For example, the clinician may ask, "Do you have a family history of diabetes?", the patient may answer, "Yes, my father had diabetes", in which case the clinician will say, "Yes, the patient has a family history of diabetes" and the system can automatically fill out the "YES" box on the scrolling eSource. While completing a physical examination, the doctor or research staff can narrate the activities they are performing and/or the results of their examination (e.g., "The lungs were clear, the heart rate was normal") and the system can transcribe this information and attribute it to the appropriate location within the eSource record.

Provisions can be made for an authorized person (doctor, clinical trial sponsor's representative, or regulatory agency) to review the eSource record with respect to a particular data record or input. An authorized person with appropriate security to access the eSource record can be provided with provisions to advance to the page or section of the eSource record in question and instantly view the video recording of that portion of the clinic visit as the video recording will be tagged to associate the portion of the video recording with the data record or input.

According to another embodiment of the present disclosure, a video and audio recording of the entire encounter between the doctor(s), the nurse(s), the clinic research coordinator(s), research assistant(s), and the patient can be captured using a combination of electronic devices as shown in FIG. 5E. The eSource unit (500) of FIG. 5A may control a series of cameras that are either included in the individual devices (502, 504) implementing the eSource unit (500) used by the clinician and the patient respectively and/or remotely located cameras (506) connected and controlled by the eSource device (502) of the clinician. In combination with identity authentication, the video and audio recordings by multiple cameras for each exchange can be utilized in the validation method shown in FIG. 5G to provide multiple validations and can serve as an excellent audit trail for these activities.

In addition, the video recording of the encounter can be utilized as a source for the clinical trial. The FDA defines source as "all information in original records and certified copies of original records or clinical findings, observations, or other activities in a clinical trial necessary for the reconstruction and evaluation of the trial. Source data are contained in source documents (original records or certified copies)." According to an embodiment of the present disclosure, the video recording itself can serve as the source for the clinical trial [see reference (5)].

In the embodiment described in the paragraph above, the "original observations and other activities in a clinical trial necessary for the reconstruction and evaluation of the trial" are recorded on video. Therefore, the FDA or other regulatory agencies can truly reconstruct the trial should they wish because it is all recorded on video and tagged to the data that is entered in the database. If one wishes to conduct "Source Data Verification" or SDV, then one simply views the video which is tagged to the data field to truly determine that it meets the ALCOA (attributable, legible, contemporaneous, original, and accurate) standard for evidence required by the FDA [see reference (3)].

As a result, the video, audio, and still images can be reviewed by the sponsor of the research study via an eMonitor system to determine if the techniques are being performed correctly and if the research staff needs additional training or instruction. The video, audio, or still images can be used to monitor for accuracy and compliance with the requirements of the study protocol. In addition, a single data point or a single point in the encounter can be reviewed for any number of patients very easily as the video related to that particular question or procedure can be accessed from the database and reviewed remotely.

In another embodiment of the present disclosure and as shown in FIG. 5A, the data collected on and/or imported into the eSource unit (500) can be subjected to validation and authentication (555) by the physician investigator at the end of the visit. The questions and answers to each question can be available for review. Any automatically generated queries regarding inclusion criteria, exclusion criteria, out of range data, illogical data, blank data fields, etc. can be answered by the clinician and then the data can be signed/authenticated by the clinician. After the authentication, the data can be printed (556), sent electronically (557) by email or other electronic messaging system, and/or stored (558) for later retrieval (559).

In the present embodiment, the video recording of the medical staff and the doctors may include identification authentication including but not limited to facial recognition, fingerprints, retinal scans, voiceprints, iris scans, typing biometrics, hand and finger geometry, signature verification, ear geometry, olfactory biometrics, and behavioral biometrics. The identification authentication can serve as security protocol to provide data access only to authorized users.

The eSource system (500) may comprise further security and/or privacy features. For example, to satisfy FDA requirements for clinical trials, information that can identify the identity of each subject may be blocked from some users of the database [see reference (3)]. For example, tier 1 users, such as the data originator, and tier 2 users, such as the investigator, or clinical research coordinator on site may have access to information that can identify a subject's identity. However, tier 3 users such as the sponsor, would not have access to such identity information. The de-identification of subject data can be done, for example, by blocking access to identity information such as name and address and/or by obscuring or blurring facial images.

As another example, the eSource system (500) can be a paper form with data collection instructions and the data collection fields to be filled in with data collected. The paper form of the eSource system (500) may have an identifier, including but not limited to a bar code on each form, each page, or each data field, so that the form and/or data field can be tracked in its usage by verifying the identifier at each use.

Example 6

Now referring to FIGS. 6A-6E, an authentication and validation method is described in various embodiments of the present disclosure for electronically assuring compliance to guidance or requirements. According to an example implementation of the embodiment in a clinical trial application, the subject can have tasks that can be performed outside of the clinic (e.g., at home). By way of example and not of limitation, the subject can be required to consume pills, powder, liquid, food, or beverage; administer a self-injection; use an inhaler, or apply a cream or gel at a given frequency; measure blood pressure (608); and/or measure body temperature (606). However, subjects can easily forget to perform the required tasks and then fraudulently log such data by forging fictitious results at a later date and/or time. Furthermore, it is also possible for subjects to erroneously log incorrect data.

A portable electronic device (610) (e.g., computer, portable computer, tablet computer, smartphone, game console, e-book reader, holographic device, television screen, video screen) can be loaded with an electronic compliance application or remotely access an electronic compliance application that is configured to validate authenticity of the data that is recorded, and maintain proof that such tasks were, in fact performed, accurately logged, and date/time/location stamped. Such unit will be referred to herein as an "electronic compliance unit". The term "electronic compliance unit" can be used interchangeably with the term "eCompliance".

Figure 6A:
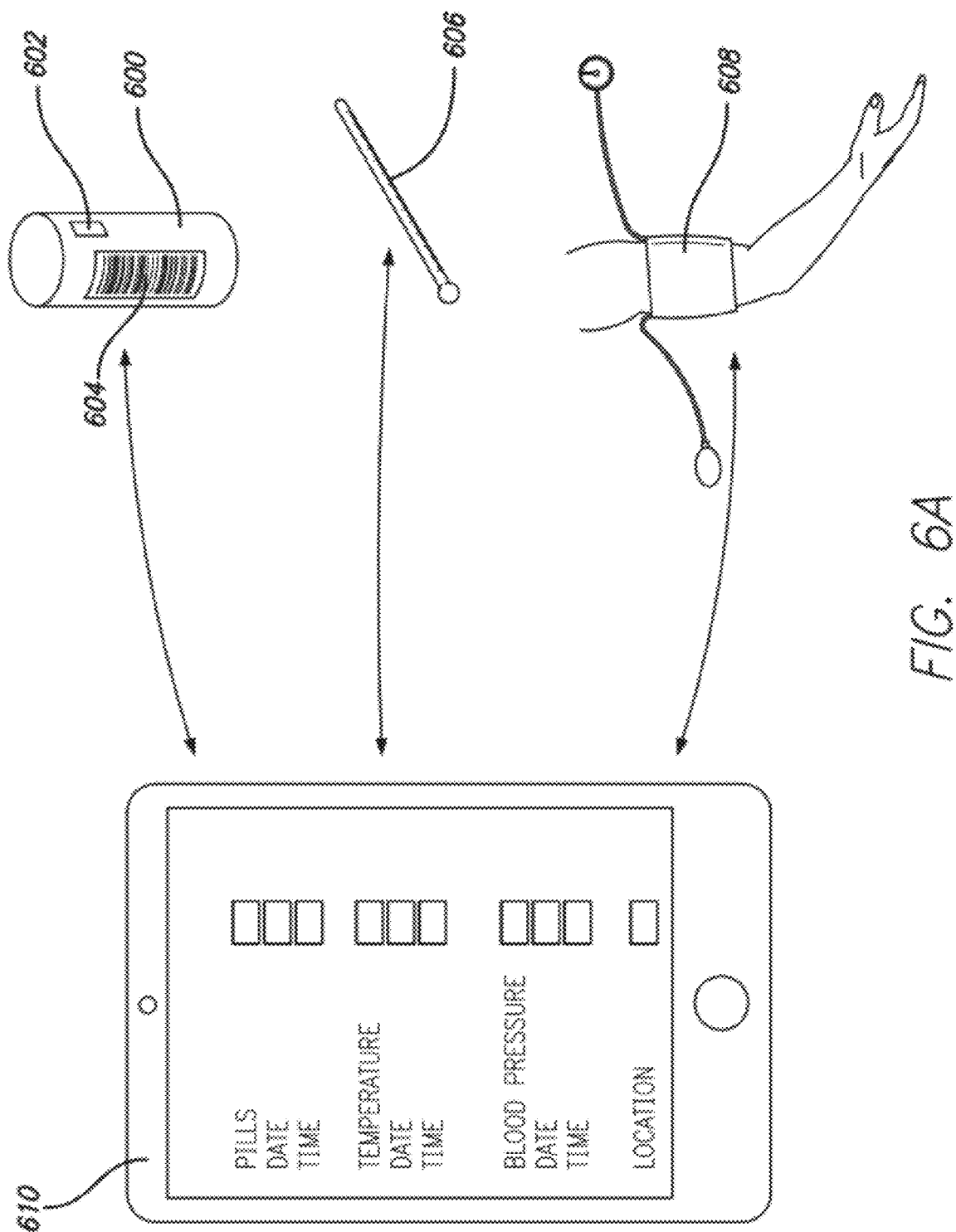
FIGS. 6A-6E show flow charts, diagrams, and displays of an exemplary electronic compliance unit of the present disclosure.
Figure 6B:
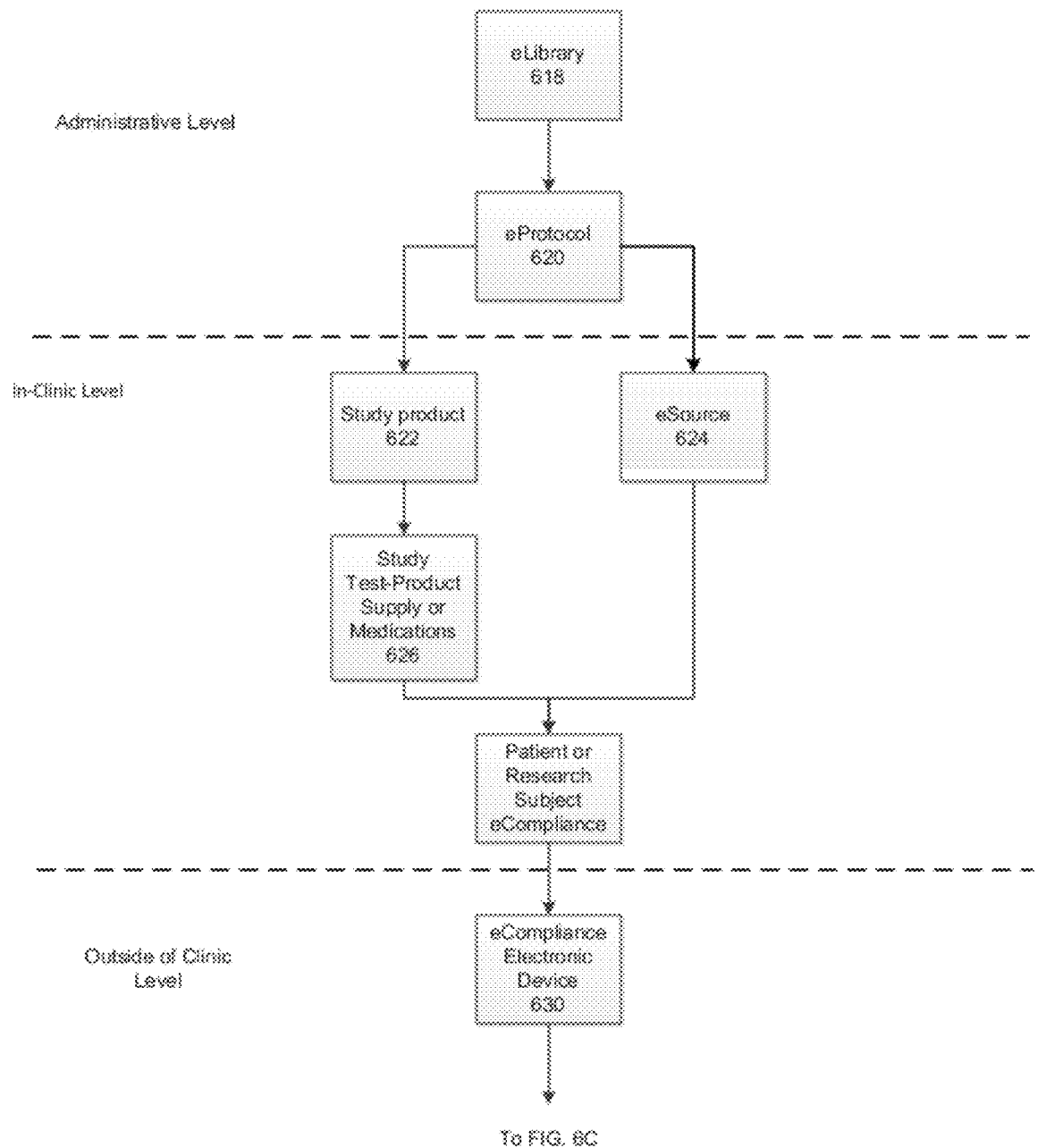

According to an embodiment of the present disclosure as shown in FIG. 6B, an electronic library database (618) can be used to create and/or store different sets of protocols. Protocols define various specifications of a clinical study or any protocol defined medical care program, which can be crucial for successful completion. Such electronic library database (618) can be used to retrieve or obtain elements and/or modules to create a set of protocols (620) that can be used, for example, in a clinical trial, disease management program, or wellness program.

According to another embodiment of the present disclosure, an electronic study product system (also referred to as "eStudy Product") (622) can be used to define a clinical study drug to be taken, packaging of the drug, location of the drug, and methods for identifying the drug itself (e.g., by shape, color, size, markings) and for identifying the packaging of the drug (e.g., barcode, RFID, and other location based services unique identifiers). The eStudy Product electronic inventory system (622) can be used with prescription and non-prescription medications, clinical study drugs, dietary supplements, medical foods, functional foods, foods, and cosmetics collectively referred to as "product".

An electronic source unit (624), as described in previous paragraphs, can be used to define instructions for taking specified drugs. Units and systems such as the electronic source unit (624) can be used together with the eProtocol (620), the electronic library database (618), the eStudy Product (622), and/or the electronic compliance unit (630). Any information from the electronic source unit (624) and the eStudy Product (622, 626) can be sent wirelessly to the electronic compliance unit (630).

The electronic compliance application can be a software application running on the electronic device (630) itself, or it can be a software application running on a remote system that can be accessed by way of the internet (or other network connection) using the electronic device. Both cases will be referred to as the electronic compliance unit (630) in the present disclosure. Such electronic device (630) can be configured with an embedded camera on the electronic device or a camera that is located external to the electronic device (630) and connected (wired or wireless) to the electronic device (630).

Figure 6C:
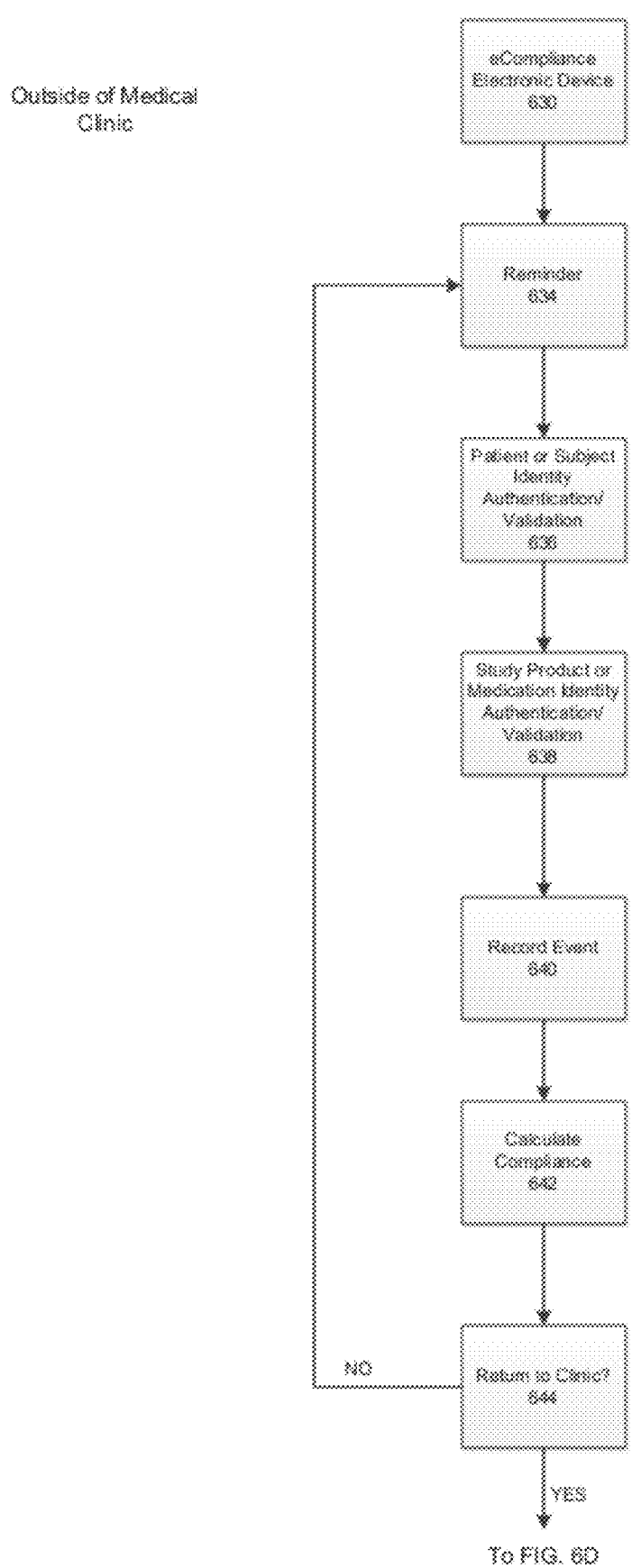
Figure 6D:
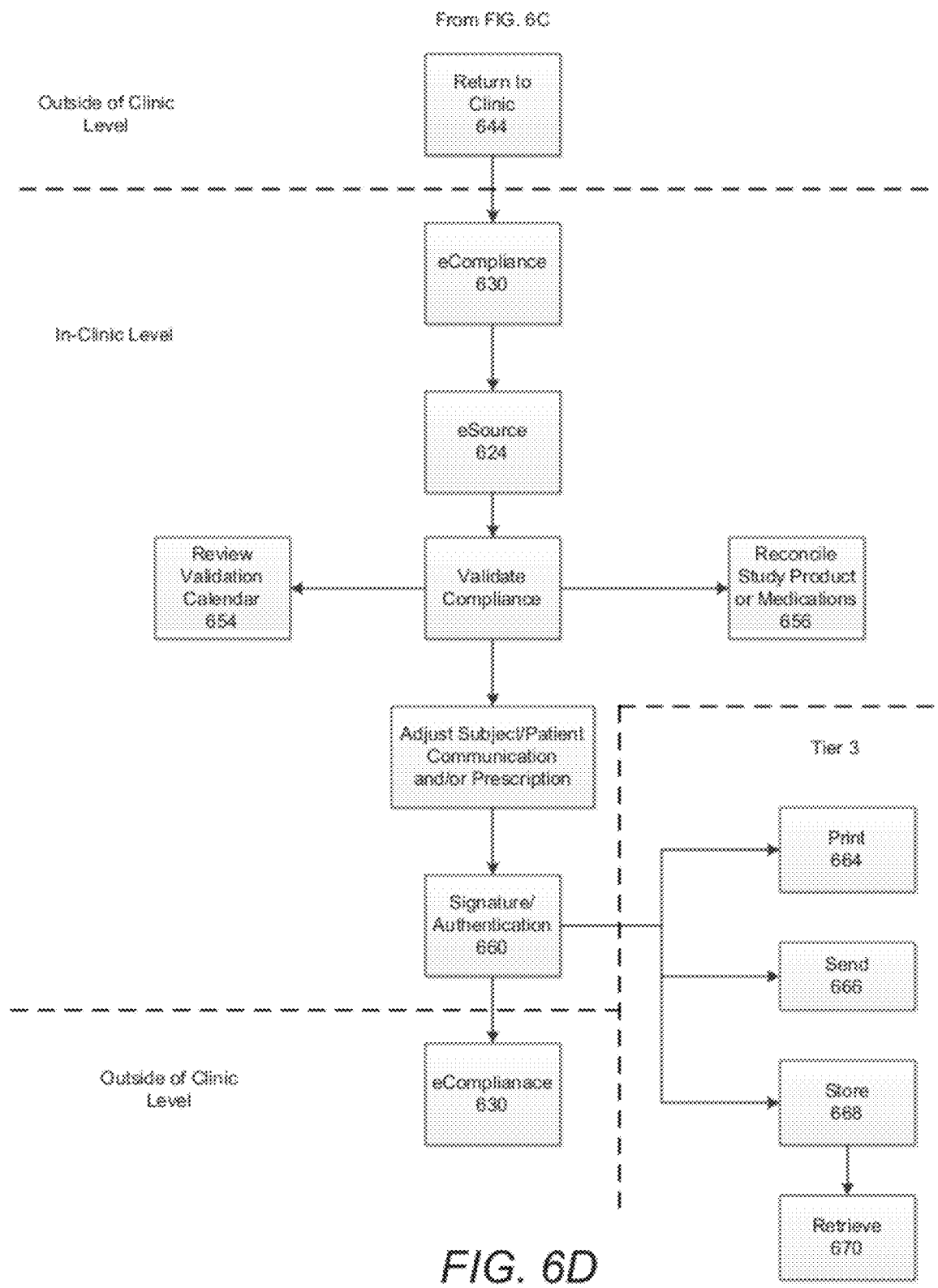
Figure 6E:
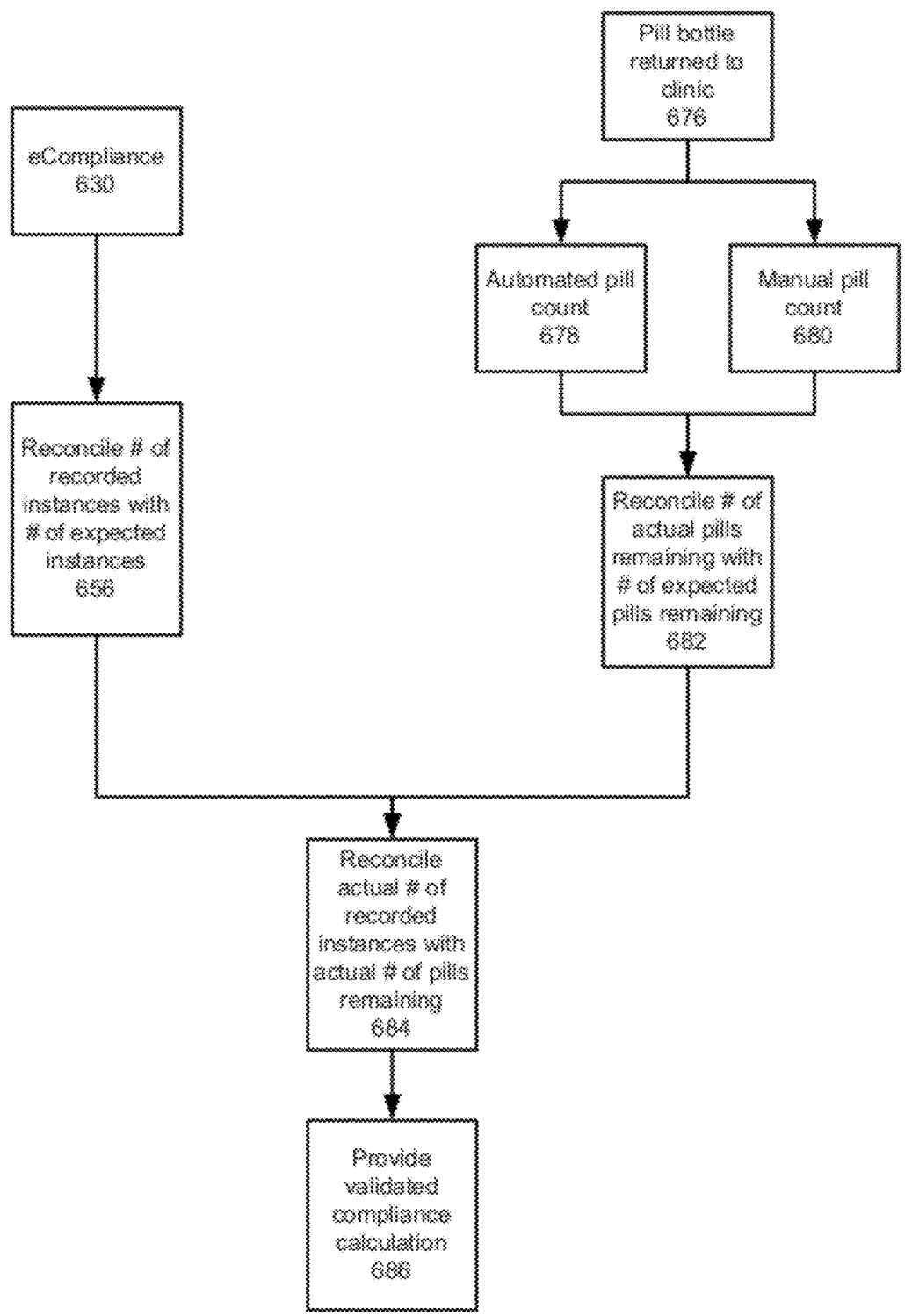

The electronic compliance unit (630) can be provided to a subject to take home for validating the subject's activities pertaining to the study or the program. According to an embodiment of the present disclosure as shown in FIG. 6C, the electronic compliance unit (630) can be configured to provide the subject with reminders (634) for activities (e.g., taking medication at a certain time, perform fingerstick blood draw, measure body temperature, complete a scale or questionnaire) to help the subject from forgetting. By way of example, if the subject is required to consume a pill at a certain time, the electronic compliance unit (630) will remind the subject that it is time to consume a pill. When the subject responds to the reminder, the electronic compliance unit (630) can be configured to authenticate that the subject, and not somebody else, is actually responding to the reminder. The electronic compliance unit (630) can identify the subject (636) by using a form of biometric identity authentication including but not limited to a camera and a facial recognition application to match the facial profile with an expected facial profile of the subject.

In an exemplary facial recognition application, the facial recognition application can access a localized database of facial recognition patterns rather than a centralized database. Specifically the electronic compliance unit (630) (or any of the other units described in this or the related patents) can identify the subject during an initial interaction with the unit. The information about the identity of the subject can be stored in a local database (in addition to a central database) so that when the subject accesses the unit again, the confirmation of identity can occur against the local database only. This can provide a much faster sequence of confirmation of identity as the electronic compliance unit (630) is not required to access a remote database and not required to search through thousands or millions of profiles in order to confirm the identity of the subject against the central database. By using the local database, there may only be one or a few identities on a single unit.

Alternatively, or in addition to the facial recognition, authentication can also occur by way of biometric authentication including but not limited to fingerprints, retina scan, voiceprint, iris scan, typing biometrics, hand and finger geometry, signature verification, ear geometry, olfactory biometrics, and behavioral biometrics.

As in the previous example where the subject is required to consume a pill, according to another embodiment as shown in FIG. 6A, a bar code (604) label can be affixed to the pill container (600) to identify the type of pill contained therein. Alternatively or in addition to the bar code (604), an RFID chip (602) can be imbedded into the pill container (600). A bar code reader or an RFID scanner can be connected to the electronic compliance unit (630) such that the subject can scan the bar code (604) or RFID chip (602), thereby ensuring the correct pill is being consumed. The date, time and location (e.g., by way of GPS coordinates) of that instance can also be recorded.

According to another embodiment, the electronic compliance unit (630) can be configured to capture a video or a still recording of the pill and then identify the pill (638) by its size, shape, color, pattern, and/or markings by way of size, shape, color, pattern, and/or markings recognition algorithms. As a result, the specific pill that the subject is about to consume can be identified and recorded, thereby minimizing the chance that an incorrect pill is consumed. Furthermore, if an incorrect pill were to be consumed, such record of consuming the incorrect pill can be stored as proof in the electronic compliance unit (630).

According to another embodiment, the electronic compliance unit (630) can be configured such that the subject can show the bottle (600), barcode (604), or pill to the camera and ask whether or not this is the correct pill (or bottle associated with the correct pill) to be consumed at that time. The electronic compliance unit (630) can also be configured to use the barcode (604); RFID chip (602); and/or size, shape, color, pattern, and/or marking recognition algorithms to confirm whether or not a bottle or pill is in fact the correct bottle or the correct pill.

Another embodiment is a compliance management component for the subject. The required schedule for compliance with the study protocol is programmed into the system and, at predetermined time points, an alert can be generated to inform the subject that it is time for him or her to perform a study related activity including, but not limited to, taking an investigational study product' filling out a diary, scale (e.g., survey question with a range of 1-10) or questionnaire; eating or drinking a specific study related food or beverage; measuring a body function (e.g., temperature, blood pressure, weight, blood sugar, etc.); and/or collecting a specimen (e.g., urine, saliva, stool, semen, blood).

Such compliance management component can also include ability to increase or decrease the frequency of reminders according to compliance rates. The alert can take the form of an audible alert, a tactile alert (e.g., vibration), a visual alert, an olfactory alert, or a gustatory alert. Exemplary methods of delivering alerts can include, but is not limited to, phone calls, emails, text messages, or any other communication methods. Such alerts can vary in timing, intensity, frequency and duration according to the current level of compliance. For example, subjects who are less compliant can receive more intense, more frequent, and longer alerts. When such less compliant subjects improve their level of compliance, the intensity, frequency, and duration of these alerts can be decreased.

According to yet another embodiment, the electronic compliance unit (630) can be configured such that, once the subject's identity is authenticated, the electronic compliance unit (630) can video record (640), via the camera, the subject performing various activity or activities such as, by way of example and not of limitation, consuming the study product, measuring a body function (e.g., body temperature, blood pressure, weight, blood sugar, etc), and/or collecting a specimen (e.g., urine, saliva, stool, semen, and/or blood).

As a result, an authenticated identification of the subject and a visual proof of the subject performing the activity (e.g., consuming the pill), with a date, time stamp, and location stamp (e.g., GPS coordinates) of the activity is recorded and stored in the electronic compliance unit (630) as evidence. The electronic compliance unit (630) can use computer vision algorithms to determine whether the recorded motion of the subject matches a general body movement of the expected activity being performed. For example, if the activity involves consuming a pill, a generally expected body movement can comprise the subject's a hand moving toward his or her mouth and inserting an object, followed by drinking of a beverage. Other examples of activities can be, consuming a powder, consuming a liquid, injecting a medication, drawing blood, measuring body functions, measuring body temperature, measuring blood pressure, measuring glucose, answering medical questions, performing a physical examination; dispensing an investigational study product, consuming an investigational study product, filling out a diary, scale, questionnaire, preparing food, consuming food, preparing a beverage, consuming a beverage, applying a cream, applying a gel, measuring weight, measuring height, measuring body size, performing an EKG, performing a stress test, collecting urine, collected saliva, collecting stool, collecting semen, and drawing blood.

In addition, any supplies that may be necessary for completion of the activity can be identified. The electronic compliance unit (630) can be configured to identify specimen containers by using barcode and/or RFID scan, or by their size, shape, color, pattern, and/or markings by way of size, shape, color, pattern, and/or markings recognition algorithms. As a result, a specific specimen container that the subject is attempting to use can be identified and recorded, thereby minimizing the chance that an incorrect specimen collection container is used.

A person skilled in the art will recognize that some clinical trial protocols specify the consumption of specific foods or beverages. The foods and beverages can be the test product of the study or they can be a special diet (e.g., low carbohydrate diet) specified by the protocol.

According to another embodiment, the electronic compliance unit (630) can be configured to capture a video or still recording of the food and then to identify the food by its size, shape, color, pattern, and/or markings by way of size, shape, color, pattern, and/or markings recognition algorithms.

Alternatively, the electronic compliance unit (630) can be configured to scan the barcode (604), RFID chip (602), or other near-field communication devices to identify the food, food package, or menu. As a result, the specific food that the subject is about to consume can be identified and recorded. Specific algorithms can inform the subject of the caloric value, macronutrient content (e.g., fat, carbohydrate, and protein) and micronutrient content (e.g., vitamins, minerals, etc.) of the food that the subject about to consume. Algorithms can also inform the subject of whether the caloric, macronutrient and micronutrient values will be in compliance with the subject's diet or outside the parameters of the subject's diet for a given time period (e.g., day, week, month, etc.). Alerts can be triggered that can recommend additional or alternative foods to be eaten instead of the current food. Furthermore, such record of consuming the food can be stored as proof in the electronic compliance unit (630).

According to another embodiment, a scale can be used to weigh the food before and after consumption. This scale can transmit a wireless or wired signal to the electronic compliance unit (630) and therefore import the weight of the remaining food. The actual food consumption can be calculated and the caloric, macronutrient, and micronutrient contents can be calculated and compared to the allowable values in the protocol.

According to another embodiment, the electronic compliance unit (630) can record information pertaining to an entire meal being consumed. By way of example and not of limitation, the recording can comprise information pertaining to the rate at which the food is being consumed, the amount of food being consumed, and the number of times food is being consumed per day. Such information can be combined with the information obtained from the compliance assessments described in previous paragraphs and can provide additional analysis on food intake.

According to another embodiment as shown in FIGS. 6C-6F, the electronic compliance unit (630) can be configured to keep track of the number of pills consumed (642) by the subject. Therefore, when the subject returns to the clinic for a follow up visit (644) and returns the bottle (600) to the clinic (676), the number of pills that are actually remaining in the bottle (600) can be counted by manually counting (680) or using an automated counting (678) device to compare (682) and can be verified against the number of pills expected to be remaining in the bottle (654, 682), thus reconciling (656) the activities logged in the electronic compliance unit (630).

According to another embodiment, adjustments to the subject's medical regimen can be made with the information about their level of compliance with the study requirements. This information can be transmitted from the electronic source unit (624) to the electronic compliance unit (630) and, after signature authentication by the clinic staff (660), can be printed (664), sent electronically (666) by email or other electronic messaging system, and/or stored (668) for later retrieval (670).

According to another embodiment, the electronic compliance unit (630) can be configured to present to the subject medical questions, scales, and questionnaires in the form of, for example, text, voice (audio), video, or hologram. In addition, the questions, scales, and questionnaires can be presented by way of a live video with a live human being or an avatar. The electronic compliance unit (630) can be further comprise an input device that can be configured for the subject to enter answers as touch screen input, text input, voice (audio), video, or holographic recording. Voice, video, or holographic recordings can be transcribed from voice to text. Voice recognition can be used as part of the identity verification process as well.

In addition, the electronic compliance unit (630) can comprise an alert system which can provide an instant connection to a person via audio, video, or hologram. Such alert system can be triggered if, for example, subjects report a significant new medical problem, technical problem, or reports thoughts of hurting themselves or others.

In addition, all recordings of the subject can be stored by the system for use as source documentation in accordance with the protocol and with regulatory requirements. All of the transcriptions of the subject's input by voice, video, or holography can also be stored for use as source documentation in accordance with the protocol and with regulatory requirements.

In another embodiment of the system, in addition to the subject being presented with medical questions, answer scales, and questionnaires, the electronic compliance unit (630) can also be configured to provide a running commentary on how the subject feels as well as anything else that the subject desires to mention. Such commentary can be in the form of a log or diary that can be recorded by touch input, text input, video, voice (audio), or holographic recording. The electronic compliance unit (630) can be configured to record the subjects' commentary for as long as the subject so desires. A transcription of the subject's voice can be provided and the transcription can then be analyzed for key words regarding how the subject feels. In addition, certain responses containing keywords and/or phrases such as "kill" or "suicide" from the subject can trigger an alert to the research facility or in extreme cases can trigger a call to emergency services such as 911.

The results of the measurements of mHealth devices can be imported directly into the electronic compliance unit (630) and can be displayed on the electronic device for review by the subject and/or research staff. Data values from these mHealth devices that are out of the expected range can trigger alerts and prompts for the research staff, including prompts for retesting, performing additional tests, or asking additional questions.

The display can be configured for use for a subject to have a plurality of sub-screens for simultaneous display of a plurality of information. For example, the display can have sub-screens showing a subject the next step to be performed, which can be a required question or a procedure according to a particular clinical study protocol. The sub-screens on display can be configured to display separately or simultaneously the question to be asked or the procedure to be performed as well as a set of guidelines or instructions pertaining to how to answer the question.

The display may also include sub-screens comprising an audio transmission, video and/or hologram of the doctor or avatar asking the question; an audio recording, video and/or holographic recording of the research subject answering the question; an elapsed time display showing the start time, the current time, the elapsed time; and a progress bar for the procedure(s) showing how many steps have been completed and how many steps are remaining. The audio, video, and/or hologram of the doctor may be a real-time stream transmitted over a wired or wireless connection and made to be viewed or heard on the electronic device.

Additionally, the display can also comprise a data import button with which the subject may initiate the importation of the data directly from an mHealth device. The importation of data from the mHealth device may be via a wired or wireless method and can be directly or through an internet protocol or other methods as described previously.

A method of validation that may be applied to any question and answer exchange step between a subject and the electronic device or between the subject and a doctor or other clinician is described. A question may be asked by the doctor (or by the electronic device) and answered verbally by the subject or input directly into the electronic device. The eCompliance unit (630) may provide the transcription of the answer from the audio portion of the audio, video, or holographic recording.

The transcription can be compared (in real time or at a later date/time) to the answer input by the subject. The two answers to the question (e.g., the answer input into the device and the answer verbally spoken and then transcribed from speech to text) will be validated by the comparison. If there is a discrepancy between the two answers (e.g., input and transcription), then the original video recording of the answer can be replayed and possibly retranscribed to validate and confirm the correct response. Once the answer has been validated, it will be sent to the database.

Provisions can be made for an authorized person (e.g., doctor, clinical trial sponsor's representative, or regulatory agency) to review the eCompliance record with respect to a particular data record or input. An authorized person with appropriate security to access the eCompliance record can be provided with provisions to advance to the page or section of the eCompliance record in question and instantly view the video recording of that portion of the clinic visit as the video recording will be tagged to associate the portion of the video recording with the data record or input.

In addition, the video recording of the encounter can be utilized as a source for the clinical trial. The FDA defines source as "all information in original records and certified copies of original records or clinical findings, observations, or other activities in a clinical trial necessary for the reconstruction and evaluation of the trial. Source data is contained in source documents (original records or certified copies)." According to an embodiment of the present disclosure, the video recording itself can serve as the source for the clinical trial [see reference (5)].

In the embodiment described in the paragraph above, the "original observations and other activities in a clinical trial necessary for the reconstruction and evaluation of the trial" are recorded on video. Therefore, the FDA or other regulatory agencies can truly reconstruct the trial should they wish because the trial is recorded on video and tagged to the data that is entered in the database. If one wishes to conduct "Source Data Verification" or SDV, then one simply views the video that is tagged to the data field to truly determine that the data meets the ALCOA (attributable, legible, contemporaneous, original, and accurate) standard for evidence required by the FDA [see reference (3)].

As a result, the video, holographic, audio, and still images can be reviewed by the sponsor of the research study via the eMonitor system to determine if the techniques are being performed correctly. The video, holographic, audio, or still images can be used to monitor for accuracy and compliance with the requirements of the study protocol. In addition, a single data point or a single point in the encounter can generally be readily reviewed for any number of subjects as the video related to that particular question or procedure can be accessed from the database and reviewed remotely.

When the subject returns to the clinic with the eCompliance system (630), the data collected on the system (630) can already have been transmitted to the doctor or clinical staff by methods described previously. Additionally, the data collected on the eCompliance system (630) can be transmitted directly to the eSource system via near-field communication, wired transmission, or wireless transmission as previously described. In addition, the doctor or clinical staff may view the data directly on the eCompliance system (630).

Once the doctor or other clinical staff has access to the data collected on the eCompliance system (630), the data, video, holographic, audio, and still images can be reviewed to determine whether or not the subject has been compliant with the requirements of the protocol.

The eCompliance system (630) may comprise further security and/or privacy features. For example, to satisfy FDA requirements for clinical trials, information that can identify the identity of each subject may be blocked from some users of the database [see reference (3)]. For example, tier 1 users, such as the originator, and tier 2 users, such as an investigator or clinical research coordinator on site may have access to information that can identify the subject's identity. However, tier 3 users such as a sponsor would not have access to such identity information. The de-identification of subject data can be done, for example, by blocking access to identity information, such as name and address, and by obscuring or blurring facial images.

Example 7

Identification of the subject can have several benefits in both the medical clinic setting and in various settings outside of the medical clinic. One skilled in the art will recognize that the majority of clinical trials takes place in medical facilities including but not limited to doctor's offices, health clinics, research clinics, hospitals, emergency departments, radiology facilities, and medical laboratories. One skilled in the art will also recognize that most research subjects will only visit these medical facilities for brief periods of time and will spend most of their time on the clinical trial outside of the medical clinic at their home, place of work, or other locations in the community. Therefore it is important for proper identification of subjects as they are about to perform study related activities both in the medical facilities and outside of these facilities. When subjects are in the research facility, they must appear within a protocol specified window of time (including both date and time) which may be specified for example in the eCTMS. When they do show up, their identity is verified. Such verification can provide a true audit trail of who interacted with the subject, who collected the data, and who performed the study procedures. Moreover, such audit trail will enable regulatory authorities to ensure that the individuals performing the study were properly trained, qualified, and employed to be performing such activities.

According to another embodiment of the present disclosure, the electronic device can be configured to further minimize fraud by recording, logging, verifying and authenticating the identity, attendance, and/or activity of a person. The electronic device loaded with such features will be referred to herein as an "electronic confirmation unit". The electronic device can further comprise a camera, which can be either a camera that is embedded on the electronic device itself or located externally to the electronic device.

In another embodiment, the electronic device can further comprise a biometric identity device including but not limited to facial recognition, fingerprints, retina scan, voiceprint, iris scan, typing biometrics, hand and finger geometry, signature verification, ear geometry, olfactory biometrics, and behavioral biometrics.

Figure 7:
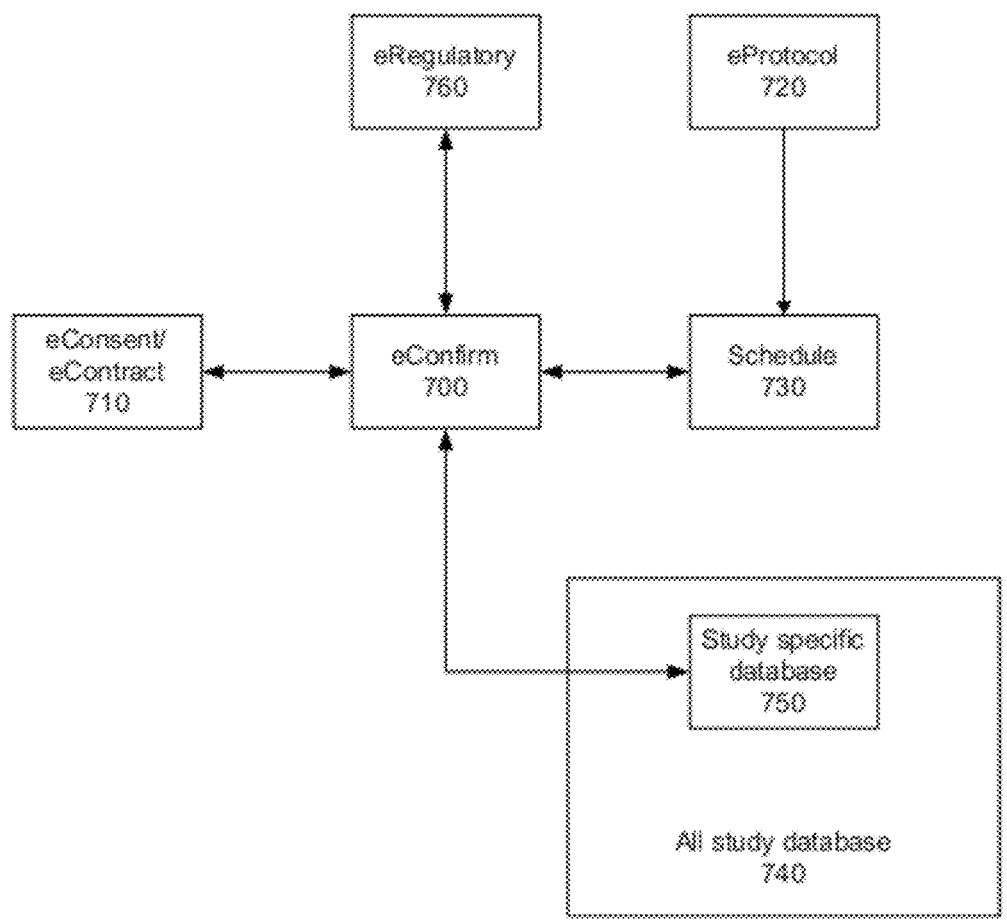
FIG. 7 shows a flow chart of an exemplary electronic confirmation unit of the present disclosure.

By way of example and not of limitation, FIG. 7 shows a system diagram where a subject that is participating in a clinical research study can visit a research clinic according to a predetermined schedule (730) set forth in a research protocol (720). When the subject arrives at the clinic for the first visit of the research protocol, the clinic staff (e.g., receptionist) can use the camera of electronic confirmation unit (700) to record a picture or video of the subject's face.

In some instances, a subject should not participate in more than one clinical research study. An example of such instance can be when guidelines (e.g., clinical trial protocols) prohibit a subject from participating in multiple studies at the same time. Yet, some subjects may either knowingly or unknowingly attempt to participate in multiple clinical research studies. In order to prevent a subject from participating in multiple clinical research studies, the electronic confirmation unit can further comprise a biometric identity confirmation application that can reference the patient's biometric identity characteristics against a master clinical studies database (750), comprising the biometric identity of other clinical studies participants, by way of example and not of limitation, a facial recognition application that can reference facial characteristics. Such comparison can ensure that the subject is not currently participating in any other studies which prohibits the subject from participating in the study for which the electronic confirmation unit is being used (740). The clinical studies database (750) can be located locally within the electronic confirmation unit (700) or remotely on a server such that the electronic confirmation unit references the database on the server either via a wired or wireless connection.

According to another embodiment, the electronic confirmation unit (700) can be implemented in clinics such that when a subject visits the research clinic for subsequent scheduled or unscheduled evaluations (730), the subject's identity can be authenticated by the clinic staff upon checking-in by using the biometric identity confirmation (e.g., facial recognition) application. In the exemplary case where facial recognition application is used, since the subject's face (picture or video) and facial characteristics were recorded during a prior visit, the facial recognition application is able to confirm that, in fact, this returning subject is the same subject from the initial visit. Furthermore, a video or still image of the subject visiting the clinic can be recorded with the camera, and the date, time, and location (e.g., coordinates obtained from a GPS) that the subject visited the clinic can be automatically logged by the electronic device to validate that subject's attendance at the clinic on that day. Alternatively, the entire visit of the subject in the clinic can be video recorded, providing further proof that the subject visited the clinic on a given date/time at a given location.

Through a connection (wired or wireless) to the previously described electronic consent unit (710), the electronic confirmation unit on the electronic device can be configured to verify if there are any outstanding or new, agreements and/or disclosures that need to be signed by the subject. If there are any outstanding or new agreements and/or disclosures that need to be signed by the subject, then the electronic device can display the agreement through the interactive process using the electronic consent unit, to have the subject sign the agreement.

In some cases, it is desired to authenticate that a particular research staff (e.g., clinical research coordinator, physician, research assistant, etc) authenticate their identity. According to another embodiment, the research staff conducting the visit (e.g., examination, evaluation, etc) with the subject can authenticate by using the facial recognition application of the electronic confirmation unit to authenticate that this research staff is authorized to conduct this visit based on their training and regulatory documentation (760) (e.g., credentials, authorizations, regulatory status). In addition, the date, time, and location that the research staff was in the clinic with the subject can be automatically logged in the electronic confirmation unit to validate the research staff's attendance at the clinic on that day.

Example 8

In another embodiment, an electronic device with a display can provide a progress bar and related information, also referred to here as an "eProgress Unit", for a plurality of usages including but not limited to providing patients information during a medical visit. Any service-business that has a relatively standardized sequence of processes required to complete a service or visit can use the eProgress unit to enhance customer service by providing their customer with real-time information about the sequence of events and the progress toward completion of that sequence of events. Customers may appreciate knowing all of the steps that will occur, the order in which they will occur, and the estimated time that they will be finished. This information can make them less anxious about the procedures and less anxious about when they will be done, and that may increase their satisfaction with the service.

Figure 8A:
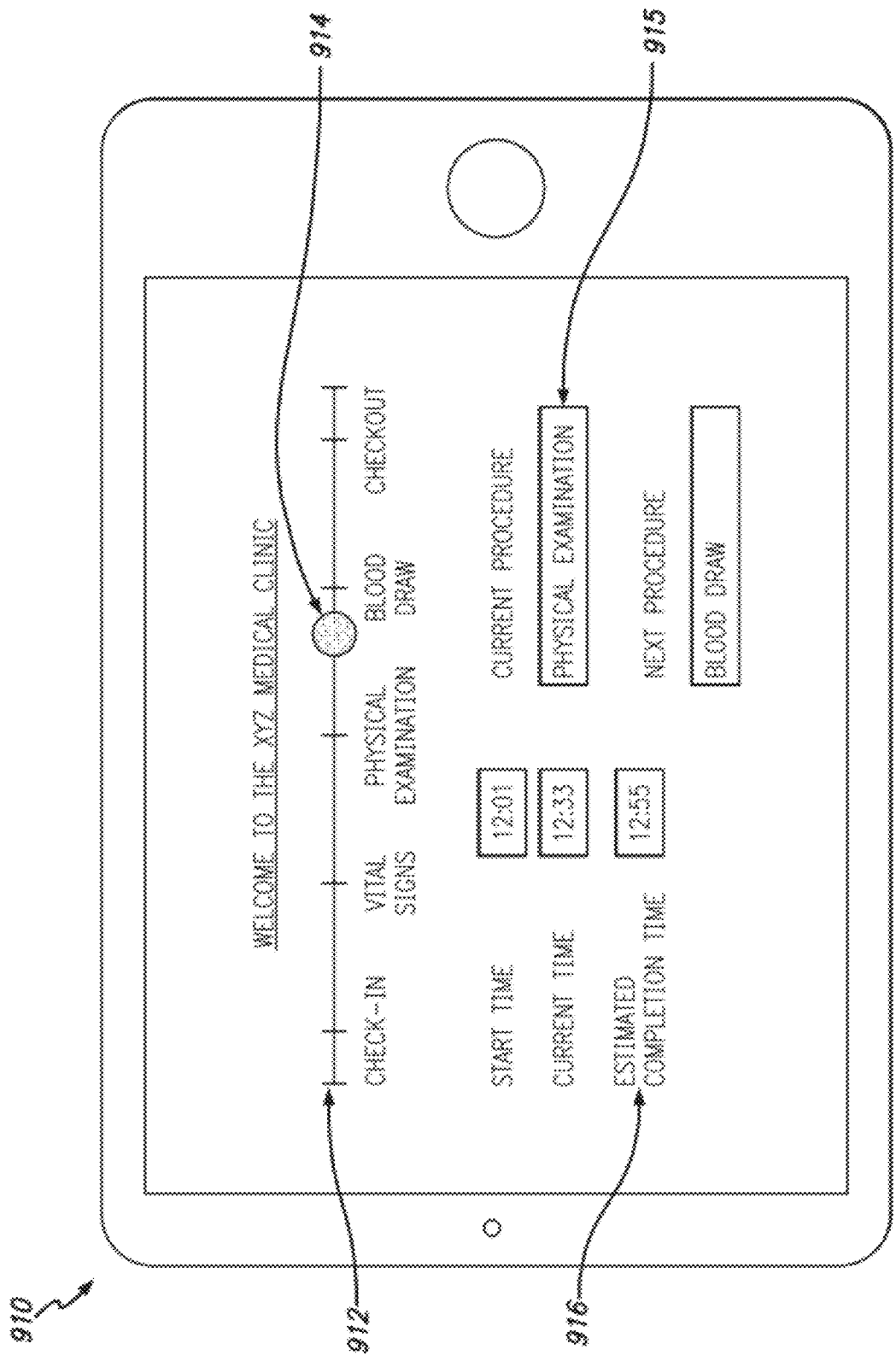

Referring now to FIG. 8A, shown here in is a exemplary display (910) of an eProgress unit for use in a clinical trials clinic. A research subject can be provided with an eProgress unit which displays the sequence of procedures which will be performed and the estimated time at which these procedures will be completed. The sequence of procedures can be displayed in a bar format (912) with the current procedure highlighted by a symbol (914). The current and next procedures can also be displayed in other formats such as text (915), pictoral, or other. If there is a delay in the actual performance of any of these procedures, the estimated time (916) can be automatically recalculated.

In another example as shown in the exemplary display (920) seen in FIG. 8B, in a medical clinic, patients can be provided an eProgress unit which not only displays the sequence of procedures which will be performed as shown in FIG. 8A (e.g. being taken back to the exam room, having their vital signs taken, being examined by the doctor, giving a urine sample), but the eProgress unit can be capable of displaying an automatically updated estimated time (922) of completion of the visit. In this example, if there is a delay in one of the steps (e.g. the doctor is delayed because of a medical emergency at the hospital), the eProgress unit can automatically update the estimated time and can display an alert (924) explaining why the estimated time has been updated.

Other exemplary uses of the eProgress unit can include businesses such as automobile repair and/or oil change centers, eye-care centers, financial services, hair salons, veterinary services, restaurants, repair services, construction services, cleaning services, and travel services.

The examples set forth above are provided to give those of ordinary skill in the art a complete disclosure and description of how to make and use the embodiments of the present disclosure, and are not intended to limit the scope of what the inventors regard as their disclosure. Modifications of the above-described modes for carrying out the disclosure may be used by persons of skill in the art, and are intended to be within the scope of the following claims. All patents and publications mentioned in the specification may be indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. For example, the person skilled in the art will understand that the number steps or components shown is only indicative and that the method can occur in more or fewer steps and that the system may contain more or less components according to the various embodiments. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

A number of embodiments of the disclosure have been described. Nevertheless, it will be understood that various modifications may be made without departing from the spirit and scope of the present disclosure. Accordingly, other embodiments are within the scope of the following claims.

REFERENCES

1. Clinical Research & Clinical Trials. *National Institute of Health*. [Online] [Cited: Jun. 15, 2011.] http://www.nichd.nih.gov/health/clinicalresearch/.
2. Wellness Council of America. Wellness Council of America. *Wellness Council of America*. [Online] [Cited: Jun. 15, 2011.] www.welcoa.org.
3. U.S. Food and Drug Administration. *Draft Guidance for Industry Electronic Source Documentation in Clinical Investigations*. December 2010.
4. World Health Organization. World Health Organization 2003. Adherence to long-term therapies. evidence for action. *World Health Organization*. [Online] 2003. [Cited: Jun. 15, 2011.] http://www.who.int/chp/knowledge/publications/adherence_introduction.pdf.
5. International Council on Harmonization. ICH E6 document, section 1.51-*FDA Guidance for Industry E6 Good Clinical Practice: Consolidated Guidance*. s.l.: http://www.fda.gov/downloads/Drugs/GuidanceComplianceRegulatoryInformation/Guidances/u cm073122.pdf.

The invention claimed is:

1. A method of measuring compliance to a protocol procedure, the protocol procedure including guidance steps intended to achieve, by one or more activities, a result related to care of a subject, comprising:
   providing an electronic device loaded with a software application and/or accessing a remote application, and by the electronic device:
   i) providing instruction to the subject, a clinical practitioner, or a professional involved in the protocol procedure to perform an activity according to the protocol procedure;
   ii) validating identity of the subject, clinical practitioner, or the professional accessing the electronic device and performing the activity;
   iii) recording said identity to keep evidence that the activity is being performed by the subject, clinical practitioner, or the professional;
   iv) recording movement or action of the subject, clinical practitioner, or the professional when the subject, clinical practitioner, or the professional performs the activity according to the protocol procedure;
   v) processing the recorded movement or action of the subject to produce recorded movement or action data;
   vi) determining whether the recorded movement or action data of the subject, clinical practitioner, or the professional are within a range of expected movement or action data processed from movements or actions expected for subjects, clinical practitioners, or professionals performing said activity, wherein, when the recorded movement or action data are within the range of the expected movement or action data, the electronic device determines compliance with the protocol procedure.

2. The method according to claim 1, further comprising presenting questions to the subject, clinical practitioner, or the professional on the electronic device, wherein the questions are in a form selected from the group consisting of: displayed text, video, audio, and hologram.

3. The method according to claim 2, further comprising responding to the questions on the electronic device, wherein the responding is performed from a method selected from the group consisting of: touch screen input, text input, audio recording, video recording, holographic recording, transcribed audio recording, transcribed video recording, and transcribed holographic recording.

4. The method according to claim 1, further comprising providing a computer database with a library of protocols, wherein the protocol procedure is obtained from at least one protocol in the library of protocols.

5. The method according to claim 1, further comprising providing a camera or a biometric device, wherein the camera or the biometric device is embedded in the electronic device or external to the electronic device.

6. The method according to claim 5, wherein the recording of the subject, clinical practitioner, or the professional performing the activity is an audio, video, and/or holographic recording obtained from the camera and wherein processing the recorded movement or action of the subject, clinical practitioner, or the professional to produce recorded movement or action data is performed by computer vision tracking algorithms executed by the electronic device, the computer vision tracking algorithms extracting information from images corresponding to the recorded movement or action.

7. The method according to claim 6, wherein the audio is converted to text.

8. The method according to claim 6, wherein the reviewing is performed locally from the electronic device or remotely from a different electronic device.

9. The method according to claim 6, wherein the audio, video, and/or holographic recording comprises identification blocking features configured to obscure said identity from reviewers that are unauthorized to know the identity.

10. The method according to claim 1, wherein the protocol procedure is selected from the group consisting of: consuming a pill, consuming a powder, consuming a liquid, injecting a medication, drawing blood, measuring body functions, measuring body temperature, measuring blood pressure, measuring glucose, answering medical questions, performing a physical examination; dispensing an investigational product, consuming an investigational study product, filling out a diary, scale, questionnaire, preparing food, consuming food, preparing a beverage, consuming a beverage, applying a cream, applying a gel, measuring weight, measuring height, measuring body size, performing an EKG, performing a stress test, collecting urine, collected saliva, collecting stool, collecting semen, and drawing blood answering medical questions; performing a physical examination; dispensing and/or taking an investigational study product; filling out a diary, scale (e.g., survey question with a range of 1-10), or questionnaire; eating a specific study related food or beverage; measuring a body function such as temperature, blood pressure, and blood sugar; measuring an anthropomorphic measurement such as weight; performing a test such as an EKG or stress test; collecting a specimen such as urine, saliva, stool, semen, or blood; determining, measuring, or diagnosing a patient condition or parameter; analytic laboratories, surgeries, pathology procedures, dermatology procedures, gastroenterology procedures, cardiology procedures, obstetrics procedures, gynecology procedures, oncology procedures, orthopedics procedures, pediatrics procedures, internal medicine procedures, sleep medicine procedures, rehabilitation procedures, radiology procedures, and/or urology procedures.

11. The method according to claim 1, further comprising importing results obtained from the protocol procedure into the electronic device.

12. The method according to claim 1, wherein the validating said identity is performed by a method selected from the group consisting of: facial recognition, fingerprints, retina scan, voiceprint, iris scan, typing biometrics, hand and finger geometry, signature verification, ear geometry, olfactory biometrics, and behavioral biometrics.

13. The method according to claim 12, wherein the validating said identity by way of biometric recognition further comprises comparing biometric characteristics of the subject, clinical practitioner, or the professional with the biometric characteristics of other subjects, clinical practitioners, or professionals, wherein the biometric characteristics of the other subjects, clinical practitioners, or professionals are stored in a biometric characteristics database.

14. The method according to claim 13, wherein the biometric characteristics database is a locally located database within the electronic device.

15. The method according to claim 1, the method further including verifying by the electronic device identity of products used by the subject, clinical practitioner, or the professional to perform the activity, wherein said verifying provides evidence that the subject, clinical practitioner, or the professional uses the correct product.

16. The method according to claim 15, further comprising prior to using the product, verifying, by way of the electronic device or by way of further electronic devices, the identity of a container of the product by scanning a bar code affixed to the container with a bar code scanner configured to operate with the electronic device.

17. The method according to claim 15, further comprising prior to using the product, verifying, by way of the electronic device or by way of further electronic devices the identity of a container of the product by scanning an RFID chip embedded into the container with an RFID scanner configured to operate with the electronic device.

18. The method according to claim 15, further comprising prior to using the product, verifying, by way of the electronic device or by way of further electronic devices, the identity of the product according to physical characteristics of the product by showing the product to a camera connected to the electronic device, wherein the electronic device is configured to compare observed physical characteristics of the product with a library of physical characteristics of a plurality of products.

19. The method according to claim 18, wherein the physical characteristics comprises one or more of: a shape, a size, a color, a pattern, and a marking.

20. The method according to claim 15, further comprising tracking number of the products used and a number of products expected to be remaining.

21. The method according to claim 15, further comprising:
providing an automated product counter, the product counter configured to count a number of products actually remaining; and
comparing the number of products actually remaining with a number of products expected to be remaining, wherein the number of products expected to be remaining is obtained from the software application on the electronic device.

22. The method according to claim 1, wherein the subject, clinical practitioner, or the professional is reminded, by way of the electronic device or by way of further electronic devices, at a predetermined amount of time of an upcoming activity according to the protocol procedure to be performed.

23. A device for determining compliance to a protocol procedure, the protocol procedure including guidance steps intended to achieve, by one or more activities, a result related to care of a subject, the device comprising:

an electronic device loaded with a software application and/or accessing a remote application;
a validating device configured to identify identity of a subject, a clinical practitioner, or professional involved in the protocol procedure;
a recording device configured to record movement or action carried out by the subject, clinical practitioner, or the professional when the subject, clinical practitioner, or the professional performs the protocol procedure; and
a memory for use with the electronic device configured to record said identity and the movement or action when the subject, clinical practitioner, or professional performs the protocol procedure,
wherein the electronic device is configured to process the recorded movement or action to produce movement or action data and to determine whether said recorded movement or action data are within a range of expected movement or action data processed from movements or actions expected for subjects, clinical practitioners, or professionals performing said activity, wherein, when the recorded movement or action data are within the range of the expected movement or action data, the electronic device determines compliance with the protocol procedure.

24. The device according to claim 23, wherein the validating device comprises a camera or a biometric device, the camera or the biometric device being embedded in the electronic device or external to the electronic device.

25. The electronic device according to claim 23, the device further including a verifying device configured to verify identity of a product used by the subject, clinical practitioner, or by the professional to perform the activity, wherein the verifying device provides evidence that the subject, clinical practitioner, or the professional uses the correct product.

26. The device according to claim 25, wherein the verifying device comprises a camera embedded in the electronic device or external to the electronic device.

27. The device according to claim 25, wherein the verifying device is a bar code scanner or an RFID scanner configured to operate with the electronic device for verifying identity of a container of the product.

28. The device according to claim 25, further comprising a product counter configured to operate with the electronic device for authenticating presence of a number of the product.

29. The device according to claim 25, wherein the verifying device is configured to identify physical characteristics of a product, and wherein the physical characteristics comprises one or more of: a shape, a size, a color, a pattern, and a marking.

30. The device of claim 23, further comprising:
a biometric characteristics capturing device;
an application configured to perform biometric recognition; and
a database locally connected with the electronic device,
wherein the biometric recognition is performed by comparing a set of biometric characteristics against a library of biometric characteristics, and wherein the library of biometric characteristics is located in the database.

31. The device according to claim 30, wherein the biometric recognition is selected from the group consisting of: fingerprint recognition, retina scan, voiceprint, iris scan, typing biometrics, hand and finger geometry, signature verification, ear geometry, olfactory biometrics, and behavioral biometrics.

* * * * *